United States Patent
McMahon et al.

(10) Patent No.: US 12,262,878 B2
(45) Date of Patent: *Apr. 1, 2025

(54) VAGINAL SPECULUM APPARATUS

(71) Applicant: Welch Allyn, Inc., Skaneateles Falls, NY (US)

(72) Inventors: Michael T. McMahon, Syracuse, NY (US); Allan I. Krauter, Skaneateles Falls, NY (US); Robert L. Vivenzio, Skaneateles Falls, NY (US); Dale C. Saddlemire, Skaneateles Falls, NY (US); Dominick Danna, Skaneateles Falls, NY (US); Stephen W. Burnett, Skaneateles Falls, NY (US); Daniel C. Briggs, Skaneateles Falls, NY (US); Scott G. Spanfelner, Skaneateles Falls, NY (US); Jon R. Salvati, Skaneateles Falls, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 357 days.

This patent is subject to a terminal disclaimer.

(21) Appl. No.: 17/701,800

(22) Filed: Mar. 23, 2022

(65) Prior Publication Data

US 2022/0211262 A1 Jul. 7, 2022

Related U.S. Application Data

(63) Continuation of application No. 16/537,726, filed on Aug. 12, 2019, now Pat. No. 11,291,359, which is a
(Continued)

(51) Int. Cl.
*A61B 1/303* (2006.01)
*A61B 1/00* (2006.01)
(Continued)

(52) U.S. Cl.
CPC ............ *A61B 1/32* (2013.01); *A61B 1/00105* (2013.01); *A61B 1/00114* (2013.01); *A61B 1/06* (2013.01);
(Continued)

(58) Field of Classification Search
CPC .. A61B 1/06; A61B 1/0655; A61B 1/303–307
See application file for complete search history.

(56) References Cited

U.S. PATENT DOCUMENTS

| 220,762 A | 10/1879 | Huffman | A61B 1/32 |
| | | | 600/223 |
| 339,754 A | 4/1886 | Foote | A61B 1/24 |
| | | | 600/241 |

(Continued)

FOREIGN PATENT DOCUMENTS

| CN | 2156814 Y | 2/1994 |
| CN | 239235 Y | 11/1996 |

(Continued)

OTHER PUBLICATIONS

Welch Allyn Inc.'s Responsive Claim Construction Brief—*Welch Allyn, Inc. v. OBP Corporation and OBP Medical Inc.*—Mar. 21, 2017.
(Continued)

*Primary Examiner* — Eduardo C Robert
*Assistant Examiner* — Michelle C Green
(74) *Attorney, Agent, or Firm* — Barclay Damon LLP

(57) ABSTRACT

A vaginal speculum apparatus includes a portable illumination assembly that is releasably attached to one of the upper blade and lower blade of a disposable vaginal speculum. The portable illumination assembly is defined by a housing that retains at least one LED and a portable power supply. The
(Continued)

portable illumination assembly can be energized by an externally accessible member after the illuminator has been attached to the speculum.

20 Claims, 25 Drawing Sheets

Related U.S. Application Data continuation of application No. 15/888,248, filed on Feb. 5, 2018, now Pat. No. 10,376,138, which is a continuation of application No. 15/453,436, filed on Mar. 8, 2017, now Pat. No. 9,949,633, which is a continuation of application No. 15/149,747, filed on May 9, 2016, now Pat. No. 9,883,792, which is a continuation of application No. 14/169,850, filed on Jan. 31, 2014, now Pat. No. 9,332,898, which is a continuation of application No. 11/910,387, filed as application No. PCT/US2006/012116 on Apr. 3, 2006, now Pat. No. 8,821,395.

(60) Provisional application No. 60/735,576, filed on Nov. 10, 2005, provisional application No. 60/667,505, filed on Apr. 1, 2005.

(51) Int. Cl.
 *A61B 1/06* (2006.01)
 *A61B 1/32* (2006.01)

(52) U.S. Cl.
 CPC .......... *A61B 1/0669* (2013.01); *A61B 1/0684* (2013.01); *A61B 1/303* (2013.01); *Y10T 29/49826* (2015.01)

(56) References Cited

U.S. PATENT DOCUMENTS

| | | | |
|---|---|---|---|
| 458,708 A | 9/1891 | Daily | A61B 1/32 600/223 |
| 471,990 A | 3/1892 | Daily | A61B 1/32 600/223 |
| 553,728 A | 1/1896 | Campbell | |
| 559,122 A | 4/1896 | Daily | A61B 1/32 600/223 |
| 596,399 A | 12/1897 | Fox | A61B 1/32 600/205 |
| 696,399 A | 12/1897 | Fox | 600/205 |
| 605,652 A | 6/1898 | Pitt | A61B 1/32 600/223 |
| 624,392 A | 5/1899 | Smith | A61B 1/06 246/1 C |
| 688,935 A | 12/1901 | Crane | A61B 1/32 600/223 |
| 872,343 A | 12/1907 | Griswold | A61B 1/32 600/101 |
| 872,344 A | 12/1907 | Griswold | A61B 1/32 600/223 |
| 936,499 A | 10/1909 | Werner | A61B 1/06 315/291 |
| 949,236 A | 2/1910 | Kaplan | A61B 1/32 600/223 |
| 1,222,478 A | 4/1917 | Sheaff | A61B 1/32 600/220 |
| 1,339,711 A | 5/1920 | Park | A61B 1/24 600/241 |
| 1,510,304 A | 9/1924 | Cameron | A61B 1/24 600/241 |
| 2,017,137 A | 10/1935 | Frederick | A61B 1/0676 600/249 |
| 2,289,226 A | 7/1942 | Richard | A61B 1/267 362/119 |
| 2,296,793 A | 9/1942 | Kirschbaum | A61B 1/0676 600/210 |
| 2,320,709 A | 6/1943 | Arnesen | A61B 1/32 600/221 |
| 2,545,201 A | 3/1951 | Gilbert | A61B 1/32 600/205 |
| 2,592,190 A | 4/1952 | Rubens | A61B 1/32 600/223 |
| 2,678,041 A | 5/1954 | Thorburn | A61B 3/1208 439/483 |
| 2,690,745 A | 10/1954 | Govan | A61B 1/24 600/241 |
| 3,162,376 A | 12/1964 | Furuya | |
| 3,324,850 A | 6/1967 | Emmett | A61B 1/32 600/223 |
| 3,332,414 A | 7/1967 | Gasper | |
| 3,373,737 A | 3/1968 | Moore et al. | |
| 3,532,088 A * | 10/1970 | Fiore | A61B 1/32 600/222 |
| 3,592,199 A | 7/1971 | Ostensen | A61B 1/267 362/197 |
| 3,595,222 A | 7/1971 | Vellacott | A61B 1/267 362/205 |
| 3,675,641 A | 7/1972 | Fiore | |
| 3,716,047 A * | 2/1973 | Moore | A61B 1/32 600/222 |
| 3,718,047 A | 2/1973 | Moore et al. | 600/212 |
| 3,744,481 A | 7/1973 | McDonald | A61B 1/32 600/213 |
| 3,762,400 A | 10/1973 | McDonald | A61B 1/00142 600/212 |
| 3,769,968 A | 11/1973 | Blount | A61B 1/32 600/223 |
| 3,789,835 A | 2/1974 | Whitman | A61B 1/0669 600/221 |
| 3,796,214 A | 3/1974 | Davis | A61B 1/32 600/201 |
| 3,815,565 A | 6/1974 | Flore | 600/222 |
| 3,815,585 A | 6/1974 | Fiore | A61B 1/32 600/222 |
| 3,841,318 A | 10/1974 | Olson | |
| 3,851,642 A | 12/1974 | McDonald | A61B 1/00142 600/205 |
| 3,885,211 A | 5/1975 | Gutai | |
| 3,916,881 A | 11/1975 | Heine | A61B 1/0669 600/212 |
| 3,934,578 A | 1/1976 | Heine | |
| 3,945,371 A | 3/1976 | Adelman | |
| 3,978,850 A * | 9/1976 | Moore | A61B 1/227 600/249 |
| 3,985,125 A | 10/1976 | Rose | 600/220 |
| D245,515 S | 8/1977 | Troutner et al. | |
| 4,067,323 A | 1/1978 | Troutner | A61B 1/0669 362/109 |
| 4,156,424 A | 5/1979 | Burgin | A61B 1/32 600/212 |
| 4,210,133 A | 7/1980 | Castaneda | |
| 4,220,985 A | 9/1980 | Hukuba | |
| 4,227,537 A | 10/1980 | Suciu et al. | |
| 4,263,898 A | 4/1981 | Wannag | A61B 1/32 600/220 |
| 4,263,899 A | 4/1981 | Burgin | |
| 4,300,541 A | 11/1981 | Burgin | A61B 1/32 600/213 |
| 4,337,763 A | 7/1982 | Petrassevich | A61B 1/32 600/210 |
| 4,385,626 A | 5/1983 | Danz | A61B 1/32 600/220 |
| 4,432,351 A | 2/1984 | Hoary | |
| D274,356 S | 6/1984 | Riedell | 600/222 |
| 4,492,220 A | 1/1985 | Hayes | |
| 4,502,468 A | 3/1985 | Burgin | A61B 1/24 600/184 |
| 4,517,628 A | 5/1985 | McDermott | |
| 4,517,702 A | 5/1985 | Jackson | |
| 4,546,761 A | 10/1985 | McCullough | A61B 1/0669 362/109 |

(56) References Cited

U.S. PATENT DOCUMENTS

| | | | |
|---|---|---|---|
| 4,562,832 A | 1/1986 | Wilder | A61B 1/32 138/DIG. 8 |
| 4,566,439 A | 1/1986 | Burgin | A61B 1/267 600/212 |
| 4,597,383 A | 7/1986 | VanDerBel | A61B 1/07 600/223 |
| 4,607,623 A | 8/1986 | Bauman | |
| 4,615,334 A | 10/1986 | Jaeger | A61B 1/00142 600/187 |
| 4,619,248 A | 10/1986 | Walsh | A61B 1/32 362/109 |
| 4,638,792 A | 1/1987 | Burgin | A61B 1/24 600/184 |
| 4,646,722 A | 3/1987 | Silverstein et al. | |
| 4,741,326 A | 5/1988 | Sidall et al. | |
| 4,763,678 A | 8/1988 | Ott | |
| 4,766,887 A | 8/1988 | Cecil, Jr. et al. | |
| 4,790,751 A | 12/1988 | Reinhardt et al. | |
| D299,532 S | 1/1989 | Cecil, Jr. et al. | |
| 4,807,600 A | 2/1989 | Hayes | |
| 4,811,937 A | 3/1989 | Rothman | |
| 4,825,850 A | 5/1989 | Opie et al. | |
| 4,869,238 A | 9/1989 | Opie et al. | |
| 4,872,837 A | 10/1989 | Issalene et al. | |
| 4,884,559 A | 12/1989 | Collins | A61B 1/32 600/205 |
| 4,905,670 A | 3/1990 | Adair | A61B 1/043 348/376 |
| 4,971,036 A | 11/1990 | Collins | A61B 1/32 600/202 |
| 4,979,498 A | 12/1990 | Oneda et al. | |
| 4,981,086 A | 1/1991 | Barca | |
| 5,005,966 A | 4/1991 | Handler | A61B 3/11 351/221 |
| 5,018,507 A | 5/1991 | Montaldi | |
| 5,026,368 A | 6/1991 | Adair | A61B 1/043 606/15 |
| 5,054,906 A | 10/1991 | Lyons, Jr. | |
| 5,063,908 A | 11/1991 | Collins | |
| 5,067,491 A | 11/1991 | Taylor, II et al. | |
| 5,143,054 A | 9/1992 | Adair | A61B 1/00147 600/104 |
| RE34,110 E | 10/1992 | Ople | |
| 5,165,387 A | 11/1992 | Woodson | A61B 1/0669 206/438 |
| 5,174,278 A | 12/1992 | Babkow | |
| 5,179,937 A | 1/1993 | Lee | |
| 5,179,938 A | 1/1993 | Lonky | A61B 1/31 600/222 |
| 5,201,908 A | 4/1993 | Jones | |
| 5,222,271 A | 6/1993 | Eganhouse | |
| 5,231,973 A | 8/1993 | Dickie | A61B 1/32 600/222 |
| 5,250,065 A | 10/1993 | Clement et al. | |
| 5,284,474 A | 2/1994 | Adair | |
| 5,306,237 A | 4/1994 | Clement et al. | |
| 5,329,938 A | 7/1994 | Lonky | |
| 5,337,734 A | 8/1994 | Saab | |
| 5,338,292 A | 8/1994 | Clement et al. | |
| 5,349,941 A | 9/1994 | Hori | |
| 5,374,244 A | 12/1994 | Clement et al. | |
| 5,386,817 A | 2/1995 | Jones | |
| 5,394,863 A | 3/1995 | Sanford et al. | |
| 5,458,122 A | 10/1995 | Yabe et al. | |
| 5,465,709 A | 11/1995 | Dickie | A61B 1/32 600/223 |
| 5,491,834 A | 2/1996 | Chia | |
| 5,499,964 A | 3/1996 | Beck | A61B 1/0669 600/205 |
| 5,545,122 A | 8/1996 | Spruill | A61B 1/015 600/186 |
| 5,595,344 A | 1/1997 | Starnes | |
| 5,639,238 A | 6/1997 | Fishburne, Jr. | |
| 5,656,014 A | 8/1997 | Rooney et al. | |
| 5,695,492 A | 12/1997 | Brown | |
| 5,711,921 A | 1/1998 | Langford | |
| 5,716,329 A | 2/1998 | Dieter | |
| 5,743,625 A | 4/1998 | Tanner | |
| 5,746,694 A | 5/1998 | Wilk | |
| 5,785,648 A | 7/1998 | Min | |
| 5,772,435 A | 8/1998 | Dorman | |
| 5,836,764 A | 11/1998 | Buchanan | |
| 5,840,013 A | 11/1998 | Lee | A61B 1/303 600/114 |
| 5,848,249 A | 12/1998 | Thompson | |
| 5,865,729 A | 2/1999 | Meehan et al. | |
| 5,868,668 A | 2/1999 | Weiss | A61B 1/32 600/221 |
| 5,873,818 A | 2/1999 | Rothfets | |
| 5,873,820 A | 2/1999 | Norell | A61B 1/32 600/220 |
| 5,888,195 A | 3/1999 | Schneider | |
| 5,899,854 A | 5/1999 | Slishman | |
| 5,906,802 A | 5/1999 | Langford | |
| 5,916,150 A | 6/1999 | Sillman | |
| 5,916,151 A | 6/1999 | Charters | |
| 5,921,777 A | 7/1999 | Dorman | |
| 5,934,904 A | 8/1999 | Elrod et al. | |
| 5,941,834 A | 8/1999 | Skladnev et al. | |
| 5,961,937 A | 10/1999 | Gobbato | |
| 6,004,265 A | 12/1999 | Hsu | A61B 1/32 600/220 |
| 6,030,210 A | 2/2000 | Bianchetti | |
| 6,036,638 A | 3/2000 | Nwawka | |
| 6,048,308 A | 4/2000 | Strong | A61B 1/303 600/205 |
| 6,083,151 A | 7/2000 | Renner | A61B 1/00135 600/112 |
| 6,102,851 A | 8/2000 | Mellin | 600/199 |
| 6,106,457 A | 8/2000 | Perkins | A61B 1/00041 396/312 |
| 6,106,467 A | 8/2000 | Perkins et al. | 600/175 |
| 6,176,824 B1 | 1/2001 | Davis | A61B 1/24 600/178 |
| 6,213,937 B1 | 4/2001 | Vivenzio | A61B 1/267 600/193 |
| 6,254,247 B1 | 7/2001 | Carson | |
| 6,379,296 B1 * | 4/2002 | Baggett | A61B 1/303 600/179 |
| 6,416,467 B1 | 7/2002 | McMillin | A61B 1/32 600/220 |
| 6,428,180 B1 | 8/2002 | Karram | A61B 5/0059 362/109 |
| 6,432,045 B2 | 8/2002 | Lemperle et al. | 600/135 |
| 6,432,049 B1 | 8/2002 | Banta | A61B 1/32 600/223 |
| 6,436,033 B2 | 8/2002 | Tan | A61B 1/32 600/224 |
| 6,589,168 B2 | 7/2003 | Thompson | A61B 1/32 600/220 |
| 6,589,188 B1 | 7/2003 | Thompson | 600/221 |
| 6,712,761 B2 | 3/2004 | Borodulin | A61B 1/32 600/184 |
| 6,830,547 B2 | 12/2004 | Weiss | A61B 1/32 600/221 |
| 6,991,604 B2 | 1/2006 | Cantrell | A61B 1/00094 600/185 |
| 7,029,439 B2 | 4/2006 | Roberts et al. | |
| 7,150,714 B2 | 12/2006 | Myles | A61B 17/0293 600/205 |
| 7,311,663 B2 | 12/2007 | Marcotte | A61B 1/32 600/220 |
| D562,762 S | 2/2008 | Saddlemire et al. | |
| D584,689 S | 1/2009 | Slawson et al. | |
| 7,631,981 B2 | 12/2009 | Miller et al. | 362/119 |
| 7,658,712 B2 | 2/2010 | Klaassen | A61B 1/32 600/220 |
| 7,668,712 B2 | 2/2010 | Klaassen et al. | 600/220 |
| 7,758,203 B2 | 7/2010 | McMahon | A61B 1/303 362/183 |

(56) References Cited

U.S. PATENT DOCUMENTS

| | | | |
|---|---|---|---|
| 7,909,759 B2 | 3/2011 | Pecherer | A61B 1/267 600/193 |
| 8,096,945 B2 | 1/2012 | Buchok et al. | |
| 8,130,520 B2 | 3/2012 | Wawro et al. | 320/114 |
| 8,142,352 B2 | 3/2012 | Vivenzio et al. | 600/199 |
| 8,157,728 B2 | 4/2012 | Danna et al. | |
| 8,317,693 B2 | 11/2012 | Grey | A61B 1/267 600/199 |
| 8,376,942 B2 | 2/2013 | Krauter et al. | |
| 8,388,523 B2 | 3/2013 | Vivenzio | A61B 1/00105 362/574 |
| 8,435,175 B2 | 5/2013 | McMahon et al. | |
| 8,512,237 B2 | 8/2013 | Bastia | A61B 1/00108 600/212 |
| 8,690,872 B2 | 4/2014 | Jayaraj | A61B 18/1402 600/249 |
| D710,500 S | 8/2014 | Roeloffs | D24/135 |
| 8,821,395 B2 | 9/2014 | McMahon et al. | |
| 8,876,709 B2 | 11/2014 | Vayser | A61B 1/32 600/205 |
| 9,883,792 B2 * | 2/2018 | McMahon | A61B 1/00105 |
| 10,376,138 B2 * | 8/2019 | McMahon | A61B 1/303 |
| 2002/0022771 A1 | 2/2002 | Diokno | A61B 1/32 600/220 |
| 2002/0055670 A1 | 5/2002 | Weiss | A61B 1/32 600/220 |
| 2002/0115910 A1 | 8/2002 | Diokno | A61B 1/32 600/220 |
| 2002/0156350 A1 | 10/2002 | Nieto | A61B 1/0676 600/223 |
| 2002/0165435 A1 | 11/2002 | Weiss | 600/205 |
| 2002/0169363 A1 | 11/2002 | Herold | A61B 1/32 600/220 |
| 2002/0183595 A1 | 12/2002 | Rioux | A61B 1/0669 600/223 |
| 2003/0095781 A1 | 5/2003 | Williams | A61B 17/02 385/146 |
| 2003/0105387 A1 | 6/2003 | Frumovitz | A61B 1/32 600/220 |
| 2003/0120131 A1 | 6/2003 | Pecherer | A61B 1/267 600/199 |
| 2003/0139673 A1 | 7/2003 | Vivenzio et al. | |
| 2003/0176772 A1 | 9/2003 | Yang | A61B 1/0669 600/220 |
| 2004/0054260 A1 | 3/2004 | Klaassen et al. | |
| 2004/0133073 A1 | 7/2004 | Berci | A61B 1/00188 600/112 |
| 2004/0183482 A1 | 9/2004 | Roberts | A61B 1/227 315/363 |
| 2004/0184288 A1 * | 9/2004 | Bettis | A61B 1/0661 362/572 |
| 2004/0186352 A1 | 9/2004 | Roberts | G02B 6/0006 600/200 |
| 2004/0186355 A1 * | 9/2004 | Strong | A61B 1/00142 600/220 |
| 2005/0085699 A1 | 4/2005 | Weiss | A61B 1/303 600/221 |
| 2005/0015975 A1 | 7/2005 | Walker et al. | 606/80 |
| 2005/0159649 A1 | 7/2005 | Patel | A61B 1/00103 600/194 |
| 2005/0159752 A1 | 7/2005 | Walker | A61B 17/142 606/80 |
| 2005/0234305 A1 | 10/2005 | Licciardi | A61B 1/32 600/221 |
| 2005/0277811 A1 | 12/2005 | Richards | A61B 1/303 600/184 |
| 2006/0155169 A1 | 7/2006 | Bastia | A61B 1/00105 600/199 |
| 2007/0060795 A1 | 3/2007 | Vayser | A61B 1/32 600/245 |
| 2007/0135687 A1 | 6/2007 | Balas | A61B 1/303 600/221 |
| 2007/0156022 A1 | 7/2007 | Patel | A61B 1/267 600/199 |
| 2007/0230164 A1 | 10/2007 | Vivenzio | A61B 1/303 362/109 |
| 2007/0230167 A1 | 10/2007 | McMahon et al. | |
| 2007/0255110 A1 | 11/2007 | Wax | A61B 1/303 600/223 |
| 2007/0287888 A1 | 12/2007 | Lovell | A61B 1/00094 600/187 |
| 2008/0004498 A1 | 1/2008 | Pecherer | 600/193 |
| 2008/0228038 A1 | 9/2008 | McMahon | A61B 1/00105 600/223 |
| 2008/0249370 A1 | 10/2008 | Birnkrant | A61B 1/00105 600/188 |
| 2008/0269565 A1 | 10/2008 | McMahon et al. | |
| 2008/0306345 A1 | 12/2008 | Balas | A61B 1/303 600/214 |
| 2009/0069634 A1 | 3/2009 | Larkin | A61B 1/303 600/222 |
| 2009/0076334 A1 | 3/2009 | Chen | A61B 1/303 600/223 |
| 2009/0097236 A1 | 4/2009 | Miller | A61B 1/00103 362/119 |
| 2009/0099421 A1 | 4/2009 | Shalman | A61B 1/00103 600/197 |
| 2009/0099422 A1 | 4/2009 | George | A61B 1/32 600/214 |
| 2009/0177044 A1 | 7/2009 | Cohen | A61B 1/303 600/220 |
| 2009/0198108 A1 | 8/2009 | Chen | A61B 1/00103 600/220 |
| 2009/0203968 A1 | 8/2009 | Winslow | A61B 1/32 600/220 |
| 2009/0216088 A1 | 8/2009 | Danna et al. | |
| 2009/0275803 A1 | 11/2009 | Krauter | A61B 1/303 600/222 |
| 2009/0287192 A1 | 11/2009 | Vivenzio et al. | |
| 2009/0312610 A1 | 12/2009 | Buchok | A61B 1/00137 600/205 |
| 2010/0030033 A1 | 2/2010 | Farley | A61B 1/07 600/249 |
| 2010/0094092 A1 | 4/2010 | Barker | A61B 1/00103 600/182 |
| 2010/0094167 A1 | 4/2010 | Linuma | A61B 1/00154 600/567 |
| 2010/0125172 A1 | 5/2010 | Jayaraj | A61B 1/06 600/249 |
| 2010/0191067 A1 | 7/2010 | Chen | A61B 1/00052 600/245 |
| 2010/0305406 A1 | 12/2010 | Braun | H01C 7/006 600/202 |
| 2011/0004068 A1 | 1/2011 | Bruto Da Costa | A61B 90/36 600/249 |
| 2011/0160540 A1 | 6/2011 | Smith | A61B 1/32 600/222 |
| 2011/0196209 A1 | 8/2011 | Shipp | A61B 1/32 600/215 |
| 2011/0237902 A1 | 9/2011 | Rosen | A61B 1/303 600/224 |
| 2011/0301424 A1 | 12/2011 | Steigerwald | A61B 1/303 600/235 |
| 2012/0078060 A1 | 3/2012 | Swift | A61B 1/32 600/220 |
| 2012/0108907 A1 | 5/2012 | Fitipaldi | A61B 1/32 600/223 |
| 2012/0209079 A1 | 8/2012 | McMahon et al. | |
| 2012/0232352 A1 | 9/2012 | Lin | A61B 1/32 600/220 |
| 2012/0265023 A1 | 10/2012 | Berci | A61B 90/361 600/249 |
| 2012/0330103 A1 | 12/2012 | Tenger | A61B 1/043 600/188 |
| 2013/0041232 A1 | 2/2013 | Li | A61B 17/3403 600/221 |
| 2013/0190568 A1 | 7/2013 | Hakanen | A61B 1/06 600/186 |

(56) References Cited

U.S. PATENT DOCUMENTS

| | | | |
|---|---|---|---|
| 2013/0197313 A1 | 8/2013 | Wan | A61B 1/32 600/202 |
| 2013/0197317 A1 | 8/2013 | Daniel | A61B 1/0684 600/249 |
| 2014/0039266 A1 | 2/2014 | Porat | A61B 1/32 600/205 |
| 2014/0148653 A1 | 5/2014 | McMahon et al. | |
| 2014/0275790 A1 | 9/2014 | Vivenzio | A61B 1/303 600/197 |
| 2014/0309499 A1 | 10/2014 | Swift | A61B 1/32 600/214 |
| 2014/0323811 A1 | 10/2014 | DeSantis | A61B 1/06 600/213 |

FOREIGN PATENT DOCUMENTS

| | | |
|---|---|---|
| CN | 2518109 Y | 10/2002 |
| CN | 2518526 Y | 10/2002 |
| CN | 2849898 Y | 5/2003 |
| CN | 2629738 Y | 8/2004 |
| CN | 1565664 Y | 1/2005 |
| CN | 2668152 Y | 1/2005 |
| EP | 0 190 014 B1 | 3/1994 |
| FR | 2490478 A1 | 3/1982 |
| WO | WO 98/25512 | 6/1998 |
| WO | WO 02/07632 A1 | 1/2002 |
| WO | WO 03/075979 A2 | 9/2003 |
| WO | WO 03/082123 A2 | 10/2003 |
| WO | WO 2006/107877 A2 | 10/2006 |
| WO | WO 2006/107878 A2 | 10/2006 |
| WO | WO 2006/121530 a2 | 11/2006 |
| WO | WO 2006/122031 A2 | 11/2006 |
| WO | WO 2008/080033 A2 | 7/2008 |
| WO | WO 2008/080040 A1 | 7/2008 |
| WO | WO 2009/149232 A2 | 12/2009 |

OTHER PUBLICATIONS

Defendant's Response Brief on Claim Construction for the '898 Patent—*Welch Allyn, Inc. v. OBP Corporation and OBP Medical Inc.*—Mar. 21, 2017.
Defendant's Opening Brief on Claim Construction for the '898 Patent—*Welch Allyn, Inc. v. OBP Corporation and OBP Medical Inc.*—Feb. 28, 2017.
Welch Allyn, Inc.'s Opening Claim Construction Brief—*Welch Allyn, Inc. v. OBP Corporation and OBP Medical Inc.*—Feb. 28, 2017.
Letter (Jensen to Nash) with enclosure: Defendant's Non-Infringement, Patient Invalidity, and Patent Unenforceability Contentions Pursuant to Local Patent Rule 3.3 with documents labeled OBP0046016 through OBP0047678—*Welch Allyn, Inc. v. OBP Corporation and OBP Medical Inc.*—Aug. 19, 2016.
Reply to Counterclaims—*Welch Allyn, Inc. v. OBP Corporation and OBP Medical Inc.*—Aug. 1, 2016.
Answer and Counterclaims—*Welch Allyn, Inc. v. OBP Corporation and OBP Medical Inc.*—Jul. 11, 2016.
Plaintiff's Disclosure of Asserted Claims and Preliminary Infringement Contentions—*Welch Allyn, Inc. v. OBP Corporation and OBP Medical Inc.*—Jul. 11, 2016.
OBP Medical ER Spec Product Brochure found at https://obpmedical.com/wp-content/uploads/2016/06/OBP-Medical-ER-SPEC-Product-Brochure-6-26-16.pdf—*Welch Allyn, Inc. v. OBP Corporation and OBP Medical Inc.*—Jan. 11, 2016.
Decision and Order—*Welch Allyn, Inc. v. OBP Corporation and OBP Medical Inc.*—Jun. 17, 2016.
Complaint (Jury Trial Demanded) with Exhibit A—U.S. Pat. No. 9,332,898 and Attachment: Civil Court Cover Sheet—*Welch Allyn, Inc. v. OBP Corporation and OBP Medical Inc.*—May 10, 2016.
Defendant's Response to Plaintiff's Objection to Judge Peebles' Report and Recommendation on Claim Construction—*Welch Allyn, Inc. v. OBP Corporation and OBP Medical Inc.*—May 9, 2016.
Welch Allyn's Response to OBP's Objections to the Report and Recommendation Concerning Claim Construction—*Welch Allyn, Inc. v. OBP Corporation and OBP Medical Inc.*—May 9, 2016.
Defendant's Objections to the Report and Recommendation on Claim Construction—*Welch Allyn, Inc. v. OBP Corporation and OBP Medical Inc.*—Apr. 18, 2016—*Welch Allyn, Inc. v. OBP Corporation and OBP Medical Inc.*—Apr. 18, 2016.
Welch Allyn's Objection to Judge Peebles' Report and Recommendation Concerning Claim Construction—*Welch Allyn, Inc. v. OBP Corporation and OBP Medical Inc.*—Apr. 18, 2016.
Amended Report and Recommendation—*Welch Allyn, Inc. v. OBP Corporation and OBP Medical Inc.*—Mar. 31, 2016.
Report and Recommendation—*Welch Allyn, Inc. v. OBP Corporation and OBP Medical Inc.*—Mar. 25, 2016.
U.S. Appl. No. 60/667,505, filed Apr. 1, 2005 entitled "Illuminated Vaginal Speculum Assembly".
Chinese Office Action and Search Report for CN 201210247067.6; dated Mar. 31, 2014; 6 pages.
Complaint—*Welch Allyn, Inc., v. OBP Corporation and OBP Medical Inc.*,—Sep. 12, 2014.
Answer and Counterclaims—*Welch Allyn, Inc., v. OBP Corporation and OBP Medical Inc.*, —Nov. 21, 2014.
Joint Claim Construction Statement—*Welch Allyn, Inc., v. OBP Corporation and OBP Medical Inc.*,—Apr. 9, 2015.
Defendant's Opening Brief on Claim Construction—*Welch Allyn, Inc., v. OBP Corporation and OBP Medical Inc.*,—May 28, 2015.
Welch Allyn's Opening Claim Construction Brief—*Welch Allyn Inc., v. OBP Corporation and OBP Medical, Inc.*,—May 28, 2015.
Defendant's Responsive Brief on Claim Construction—*Welch Allyn, Inc., v. OBP Corporation and OBP Medical Inc.*,—Jun. 25, 2015.
Welch Allyn's Responsive Claim Construction Brief—*Welch Allyn, Inc., v. OBP Corporation and OBP Medical, Inc*,—Jun. 25, 2015.
Welch Allyn, Inc.'s Memorandum of Law in Opposition to OBP's Motion to Strike the Bennett and Spantelner's Declarations—*Welch Allyn, Inc., v. OBP Corporation and OBP Medical Inc.*,—Jun. 9, 2018.
Defendant's Memorandum of Law in Opposition to Plaintiff's Objections to the Expert Declaration of Karl R. Leinsing and in Support of Defendant's Motion to Strike the Supplemental Declaration of Scott G. Spanfeiner—*Welch Allyn, Inc., v. OBP Corporation and OBP Medical Inc.*,—Jul. 9, 2015.
Letter (Nash to Peebles)—*Welch Allyn, Inc., v. OBP Corporation and OBP Medical Inc.*,—Sep. 2, 2015.
Letter (Jensen to Peebles)—*Welch Allyn, Inc., v. OBP Corporation and OBP Medical Inc.*,—Sep. 3, 2015.
Transcript—Markman Hearing—Aug. 19, 2015—*Welch Allyn, Inc., v. OBP Corporation and OBP Medical Inc.*
Expert Report of Karl R. Leinsing, MSME, PE on Defendant's Proposed Claim Construction—*Wellch Allyn, Inc., v. OBP Corporation and OBP Medical Inc.*,—Apr. 6, 2015.
Defendant's Non-Infringement, Patent Invalidity and Patent Unenforceability Contentions Pursuant to Local Patent Rule 3.3—*Welch Allyn, Inc., v. OBP Corporation and OBP Medical Inc.*,—Feb. 5, 2018.
Delendanit's Slides in Support of Claim Construction—Markman—*Welch Allyn, Inc v. OBP Corporation and OBP Medical Inc.*, —Aug. 20, 2015.
Defendant's Preliminary Proposed Claim Construction Under Local Patent Rule 4.3—*Welch Allyn, Inc., v. OBP Corporation and OBP Medical Inc.*,—Apr. 6, 2015.
Defendant's Responses to Plaintiff's First Set of Interrogatories—*Welch Allynm Inc., v. OBP Corporation and OBP Medical Inc.*,—Jan. 20, 2015.
Plaintiff's Disclosure of Asserted Claims and Preliminary Infringement Contentions—*Welch Allyn, Inc., v. OBP Corporation and OBP Medical Inc.*,—Jan. 8, 2015.
Plaintiff's Objections and Answers to Defendant's First Set of Interrogations—*Welch Allyn, Inc., v. OBP Corporation and OBP Medical Inc.*,—Jan. 26, 2015.
Welch Allyn Inc's Local Patent rule 4.3 Disclosure—*Welch Allyn, Inc., v. OBP Corporation and OBP Medical Inc.*,—Apr. 6, 2015.

(56) References Cited

OTHER PUBLICATIONS

Slides—Welch Allyn—*Welch Allyn* v. *OBR Medical*—Claim Construction Hearing—Aug. 19, 2015.

\* cited by examiner

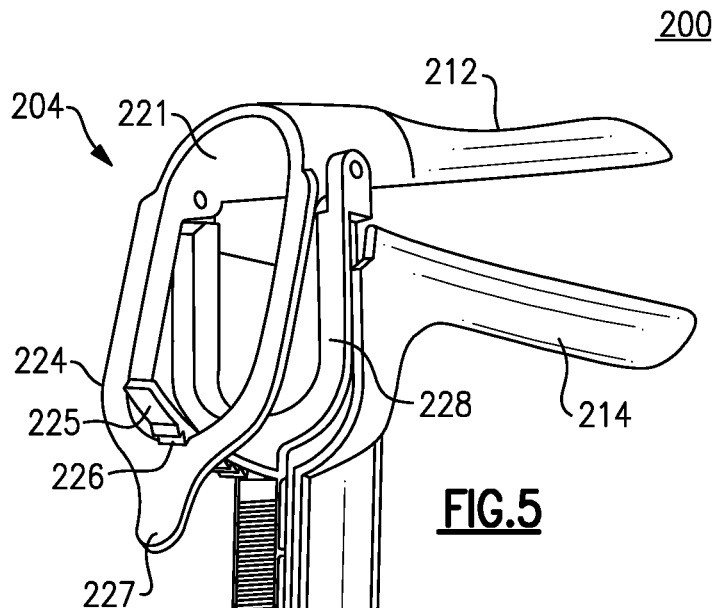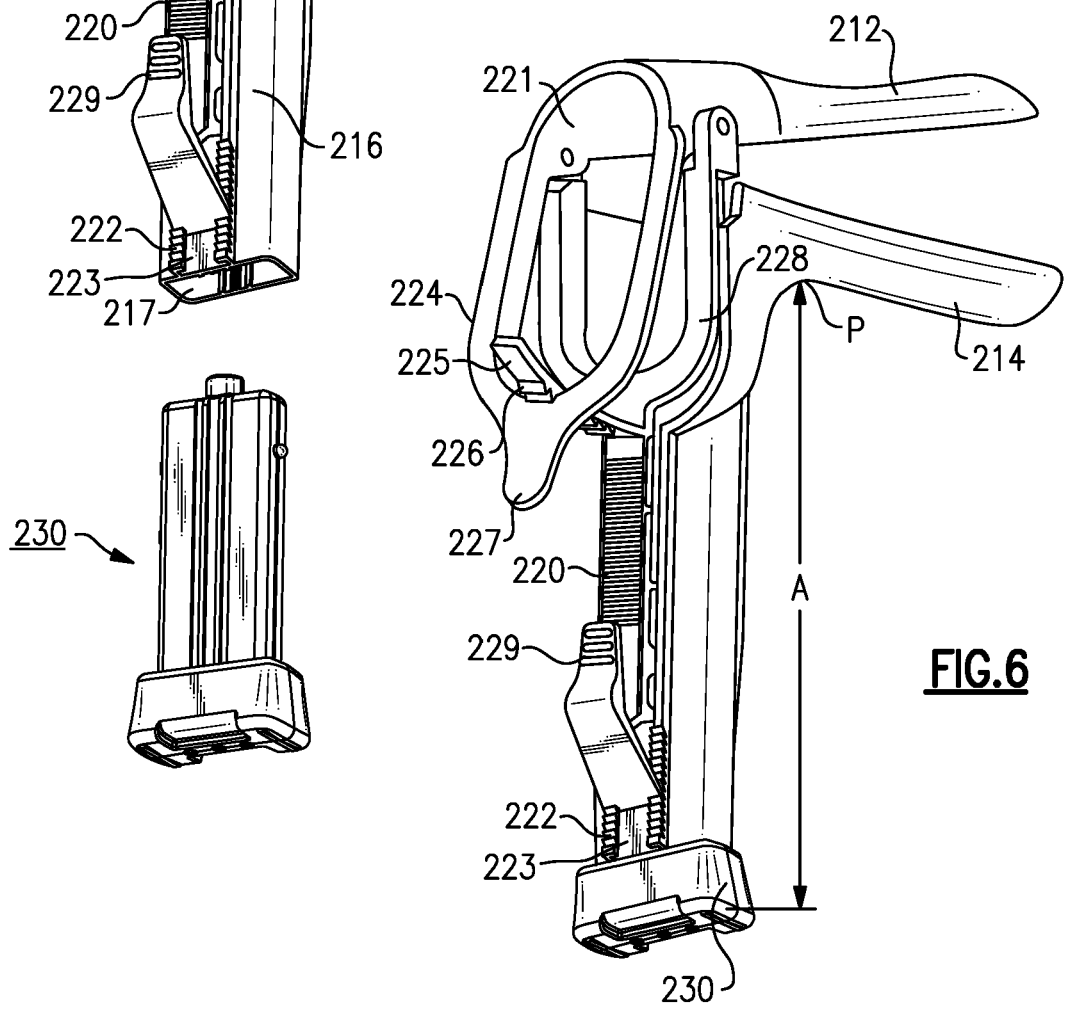

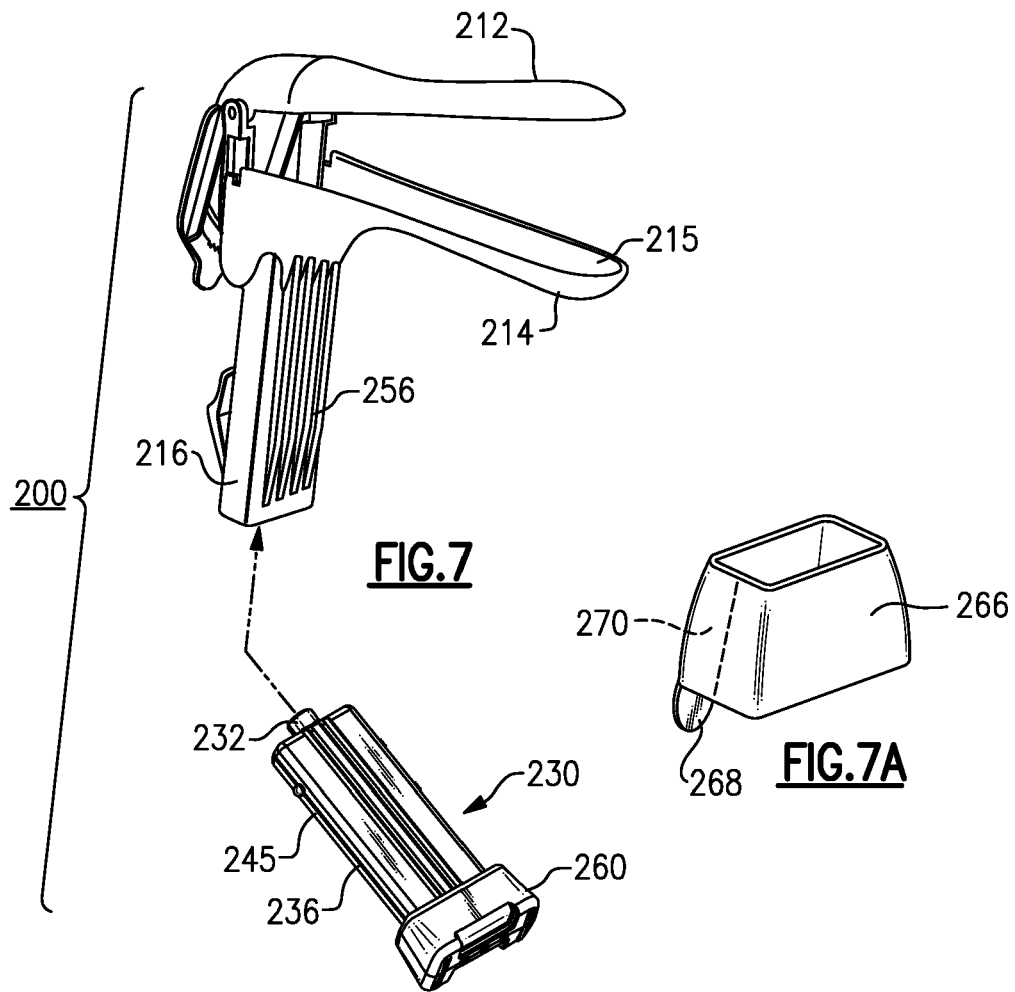
FIG.7
FIG.7A
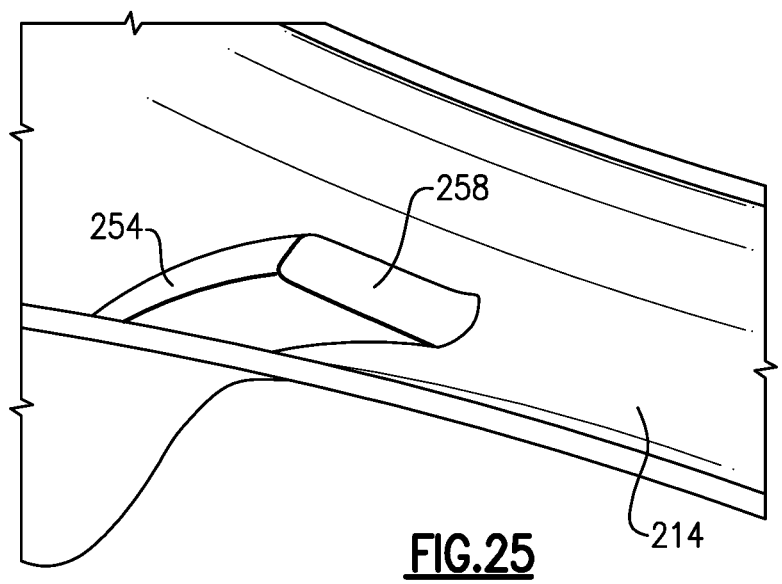
FIG.25

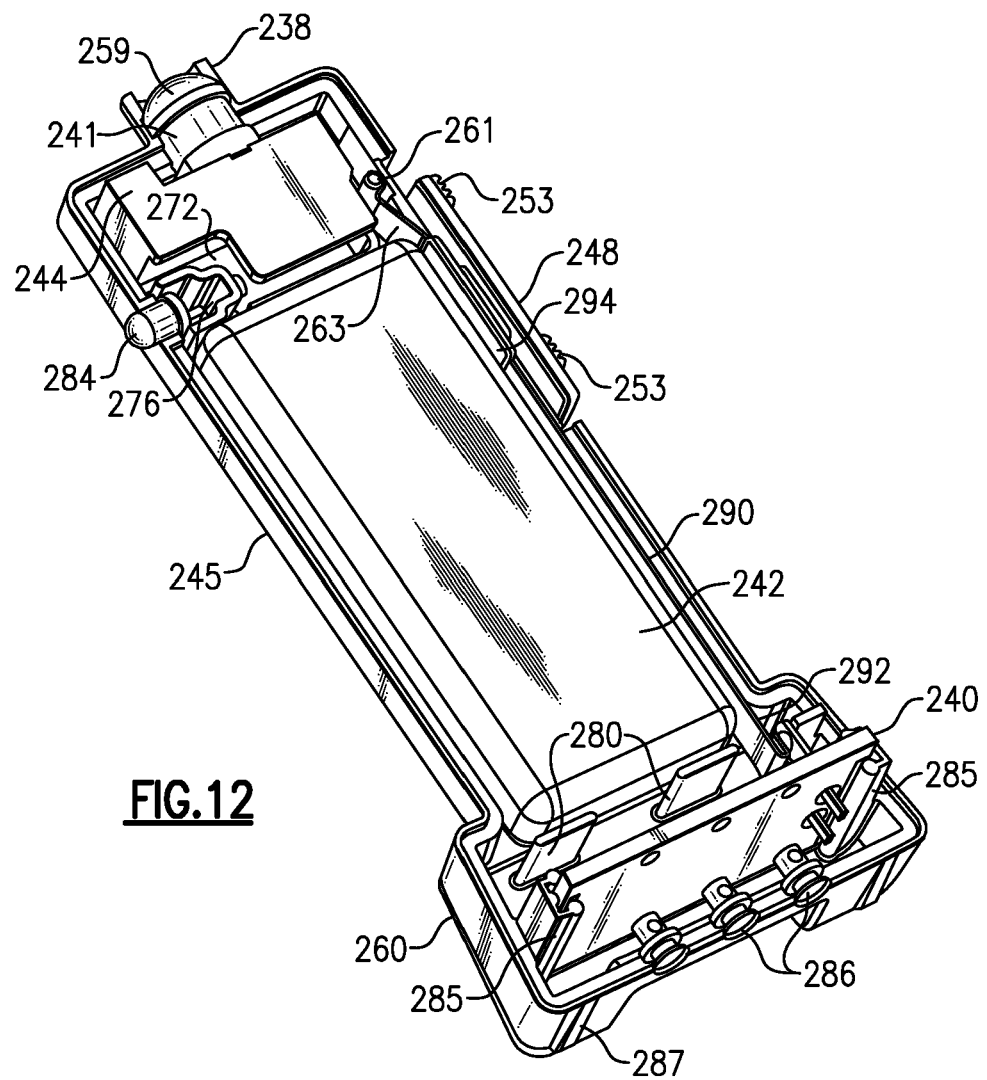

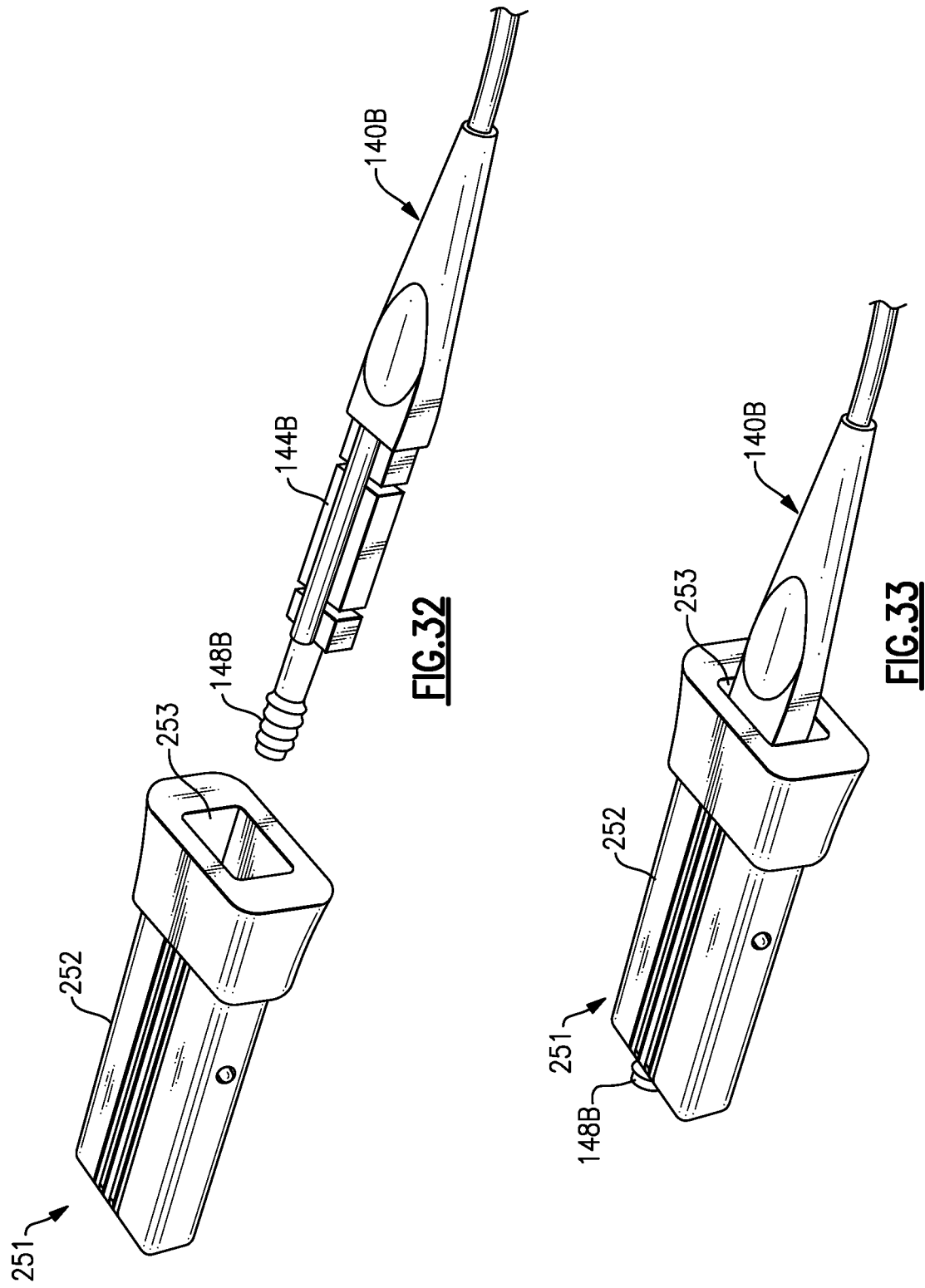

VAGINAL SPECULUM APPARATUS

CROSS REFERENCE TO RELATED APPLICATIONS

This application is a continuation patent of U.S. Ser. No. 16/537,726 filed on Aug. 12, 2019, which is a continuation of U.S. Ser. No. 15/888,248 filed on Feb. 5, 2018 (now U.S. Pat. No. 10,376,138), which is a continuation of U.S. Ser. No. 15/453,436 (now U.S. Pat. No. 9,949,633), issued on Apr. 24, 2018, which is a continuation of U.S. Ser. No. 15/149,747 (now U.S. Pat. No. 9,883,792), issued on Feb. 6, 2018, which is a continuation of U.S. Ser. No. 14/169,850 (now U.S. Pat. No. 9,332,898), issued May 10, 2016, which is a continuation of U.S. Ser. No. 11/910,387 (now U.S. Pat. No. 8,821,395), issued on Sep. 2, 2014, which is a national stage application of PCT/US2006/012116, filed on Apr. 3, 2006. The prior PCT application is further based upon the following two (2) provisional patent applications, claiming priority based on 35 USC § 119(e): U.S. Ser. No. 60/667,505, filed Apr. 1, 2005, entitled: ILLUMINATED VAGINAL SPECULUM ASSEMBLY; and U.S. Ser. No. 60/735,576, filed Nov. 10, 2005, entitled: ILLUMINATED VAGINAL SPECULUM ASSEMBLY. The entire contents of each above-noted application is herein incorporated by reference in their entirety.

FIELD OF THE DISCLOSURE

This application generally relates to the field of hand-held medical diagnostic instruments, and more particularly to a vaginal speculum apparatus including a single-use or single patient speculum that distributes illumination from at least one illumination assembly attached to the speculum.

BACKGROUND OF THE DISCLOSURE

Vaginal specula are commonly known apparatus presently used in the field of diagnostic medicine for purposes of examining the cervix of a female patient. A typical vaginal speculum includes an upper blade member and a lower blade member that are operated upon to open and close by means of an articulation mechanism in order to dilate the vaginal cavity of the patient. According to one version of a vaginal speculum apparatus that is manufactured and sold by Welch Allyn, Inc. of Skaneateles Falls, New York, a corded illumination assembly is received within a hollow handle portion of a disposable speculum made from a molded plastic material. The illumination assembly includes a miniature light source, such as a halogen or other miniature incandescent lamp, which is contained within an assembly housing and is tethered by cabling to a dedicated (e.g., AC) power source. The light source is coupled, when received by the hollow handle portion, with the proximal end of a curved light pipe disposed within the lower blade member, the light pipe being formed from a light transmissive material. Light is transmitted from the light source by means of internal reflection along the light pipe to a distal end, the light pipe extending along the interior of the lower blade member. Light is projected from the distal end of the light pipe toward the distal end of the lower blade member to the target (i.e., the cervix), thereby permitting a practitioner to conduct an effective patient examination.

One problem with the herein-described light pipe is that a so-called "hot" spot is developed at the distal light emitting end. The distal light emitting end further produces back reflection of light to the eye of the user along a viewing aperture of the speculum that is formed between the upper and lower blade members at the proximal ends thereof. This back reflection produces considerable amounts of glare, thereby impairing the effectiveness of an examination. In addition, the configuration of the distal end of the current light pipe provides non-uniform light distribution at the target (e.g., the cervix).

Another problem is that the body of the light pipe extends into the lower field of view of the user (e.g., the physician), creating obstruction of the target. In addition, shadowing of external illumination is caused by the distal light pipe end.

A further concern is the amount of plastic material that is used in the lower blade member of the molded disposable speculum, including the material taken up by the light pipe and the hollow handle portion. Excessive plastic material results in extra cost of manufacture. The molding of the lower blade member is further affected in that a stress concentration is created at the distal end of the light pipe, based on its squared discontinuous end, resulting in weak location and potential breakage. Moreover, there is difficulty in molding due to the abrupt change in cross section near the gate.

Yet another problem is that body fluids expelled from examination are often trapped by the distal end of the light pipe, producing a contamination issue as well as impairing the efficiency of examination given the effect on light transmission of a buildup of fluids against the light-emitting surface of the light pipe.

Yet another problem is that the industry has become content with the concept of utilizing a tethered illumination assembly. Though effective and highly useful, there are occasions in which such assemblies make examination impractical to perform such as, for example, instances in which the patient is bed-ridden. In these situations, the corded portion of the speculum apparatus can become an impediment to examining a patient. In addition, the use of corded illumination assemblies requires a non-portable (e.g., AC) power supply to be present in the examination area, making field examinations difficult. Still further, corded assemblies can become tangled or become a source of dirt or other contamination, requiring frequent cleaning between examinations.

Yet still further, the advent of alternative light sources, such as LEDs, provide a means for providing efficient illumination with a longer service life than that of incandescent lamps. Heretofore, the incorporation of such light sources in portable illumination systems for vaginal specula has been discouraged in the field due to inefficiencies in power conversion and illumination output. Provision of these light sources, at least in certain instances is desirable, but presently unavailable for use in such apparatus.

SUMMARY OF THE DISCLOSURE

According to one aspect of the present application, there is provided a vaginal speculum apparatus, said apparatus comprising a portable illumination assembly defined by a housing that retains a portable power supply and at least one LED, and a speculum comprising an upper blade and a lower blade, said lower blade including a handle portion sized to receive at least a portion of said portable illumination assembly and wherein the at least one LED contained within said housing is coupled to a light pipe extending into the lower blade of the speculum.

The portable illumination assembly can be releasably attached to the speculum. According to one version, the illumination assembly can be attached to the lower blade of the speculum and positioned therein so as to be optically coupled to the light pipe.

According to at least one version, the portable illumination assembly can include means for energizing the at least one LED contained within the housing.

The LED energizing means can be disposed on the exterior of the housing of the portable illumination assembly. According to one version, a switch mechanism can include a mechanical switch member, having a portion that is provided on the exterior of the housing, in which the switch member is biased in an off position. Engagement of the illumination assembly with the receiving cavity of the speculum causes a feature within the speculum to act upon the biased switch member. The feature can include at least one protrusion, rib, or groove, for example, that is formed within the receiving cavity. For example and according to a preferred version, a set of rails is provided to retain the assembly and to permit automatic energization of the contained light source.

According to another version, the speculum can include at least one opening that permits access to the LED energizing means of the portable illumination assembly.

At least one of the illumination assemblies can be powered by at least one battery, either retained directly within an assembly housing or alternatively by way of a connected component, such as by means of an attached power adapter. The power adapter can be tethered to the housing or alternatively can include a body that is mechanically and electrically linked or engaged with the housing. The power adapter can contain either a primary or auxiliary power supply, depending on the application. For example, one power adapter provides auxiliary power in the event that battery power is low or depleted. The auxiliary power supply in this power adapter can be at least one battery or a non-compact (e.g., AC) power supply.

In a preferred version, the at least one battery is rechargeable wherein an illumination assembly containing same can be placed in a docking or recharging station. The illumination assembly can include a low-battery power indicator to notify the user that recharging may be necessary. The docking station can permit, according to one version, simultaneous recharging of a plurality of illumination assemblies. In another version and as noted, the illumination assembly can be separately attached to a backup or auxiliary power supply, such as an AC power supply or at least one other battery.

In at least one version, the light pipe is releasably attached to the speculum. In another version, the light pipe can be integral to the lower blade of the speculum.

In one version, the speculum is disposable and the portable illumination assembly is reusable. Alternatively, the entire apparatus can be disposable.

According to another aspect claimed herein, there is described a vaginal speculum apparatus, said apparatus comprising a portable illumination assembly comprising a portable power source and at least one LED contained within a common housing, and a speculum having an upper blade, a lower blade and a mechanism enabling relative movement between said upper and lower blades to enable dilation of a patient, said portable illumination assembly being releasably attachable to one of said upper and said lower blades of said speculum.

In one version, the portable illumination assembly is axially received within a portion of the lower blade of the speculum. The illumination assembly can be coupled to a proximal end of a light pipe, the light pipe having a distal light emitting end. The portable illumination assembly can be releasably or otherwise coupled to the light pipe. In one version, the speculum includes a cavity disposed in a handle portion of the lower blade, the cavity being configured to receive at least a portion of the illumination assembly housing.

According to one version, the portable illumination assembly housing includes externally accessible means for energizing the at least one LED. For example, the illumination assembly can include a switch mechanism to energize the contained light source automatically when placed at least a predetermined distance into the receiving cavity. Additionally, removal of the illumination assembly, according to this version, automatically causes the light source contained therein to be de-energized.

In one version, the LED energizing means can include an exterior switch member that is acted upon by a corresponding feature of the speculum to cause automatic energization/de-energization of the contained light source. For example, the speculum can include at least one protrusion, tab, groove or other suitable engagement feature for acting upon the exterior switch member or can act upon a close contacting fit with the interior of the receiving cavity.

In another version, the LED energizing means is configured for manual operation, thereby enabling the illumination assembly to also act as an examination light without the speculum, as needed. The speculum can include at least one feature, such as at least one opening, enabling user access to the LED energizing means, even while the illumination assembly is inserted within the speculum, enabling the illumination assembly to be selectively de-energized without requiring removal. According to one version, the switch member is biased in an Off position. The switch member can be manually located into a "locked" position with the contained light source being initially energized prior to insertion into the receiving cavity of the light source. In the "locked" position, the automatic energization features of the speculum/assembly would not be active and the bias feature is overridden until the user moves the switch member out of this "locked" position.

The illumination assembly can be retained by at least one engagement/retention feature provided within the receiving cavity, such as grooves, channels, ribs and the like, wherein the at least one engagement/retention feature can also co-act to permit specific alignment of the illumination assembly relative to the receiving cavity.

According to one version, the illumination assembly can utilize the alignment/retention features, but the assembly can be disposed in one or more rotational orientations within the receiving cavity about a primary axis of the illumination assembly, while also permitting automatic operation of the switch mechanism.

According to one version, the speculum is disposable, Alternatively, the entire apparatus, including the illumination assembly, is disposable.

According to yet another aspect claimed herein, there is provided a method of assembling a vaginal speculum apparatus, said apparatus comprising a vaginal speculum having upper and lower blades, said method comprising the steps of releasably attaching a portable illumination assembly to one of said upper blade and said lower blade and configuring said illumination assembly with exterior accessible means to enable energization of a contained LED. The illumination assembly can be tethered or otherwise connected to a dedicated (e.g., AC) power supply or can include means for receiving at least one battery for powering the at least one LED, such as a white LED.

The illumination assembly includes a power supply and a mechanism for selectively energizing the at least one contained LED, either automatically upon attachment to the speculum, and/or manually by the user. At least one opening can be provided in the speculum to enable a user to access the exterior accessible means for energizing the contained LED.

According to one version, a receiving cavity of the speculum includes features to permit the illumination assembly to be retained by the speculum, such as ribs, protrusions or grooves. The retaining features can also serve to align the illumination assembly with respect to the receiving cavity and with features that would enable automatic energization/de-energization of the at least one LED.

The apparatus can include means for dissipating heat generated by the illumination assembly. In one instance, the handle portion is sized to channel heat from the illumination assembly. In another instance, at least one air gap is formed in the receiving cavity.

In one version, the illumination assembly can be coupled with a light pipe upon attachment of the illumination assembly to the speculum. The light pipe can be releasably attached to the speculum or integral therewith. In one version, the speculum is disposable. In an alternative version, the entire apparatus is disposable.

In addition, the portable illumination assembly can be attached without modification to the speculum.

The speculum apparatus further permits existing illumination assemblies to be adaptively attached to the handle portion of a speculum.

These and other objects, features and advantages will be readily apparent from the following Detailed Description which should be read in conjunction with the accompanying drawings.

BRIEF DESCRIPTION OF THE DRAWINGS

FIG. 5 is a partially unassembled rear perspective view of a vaginal speculum apparatus that is made in accordance with a first embodiment;

FIG. 6 is a rear perspective view of the vaginal speculum apparatus of FIG. 5, as assembled;

FIG. 7 is a front perspective view, partially unassembled, of the vaginal speculum apparatus of FIGS. 5 and 6;

FIG. 7A is a perspective view of a disposable sheath member used to cover a portion of the illumination assembly of the vaginal speculum apparatus of FIG. 7;

FIG. 12 is a perspective view of the illumination assembly of FIGS. 8 and 11, with the cover removed;

FIG. 25 is a perspective view of the distal end of the light pipe of the vaginal speculum that is depicted in FIGS. 5-7;

FIGS. 32 and 33 are perspective views of a speculum adapter as used with a corded illumination assembly in an unassembled and partially assembled condition;

DETAILED DESCRIPTION

Figure 1:
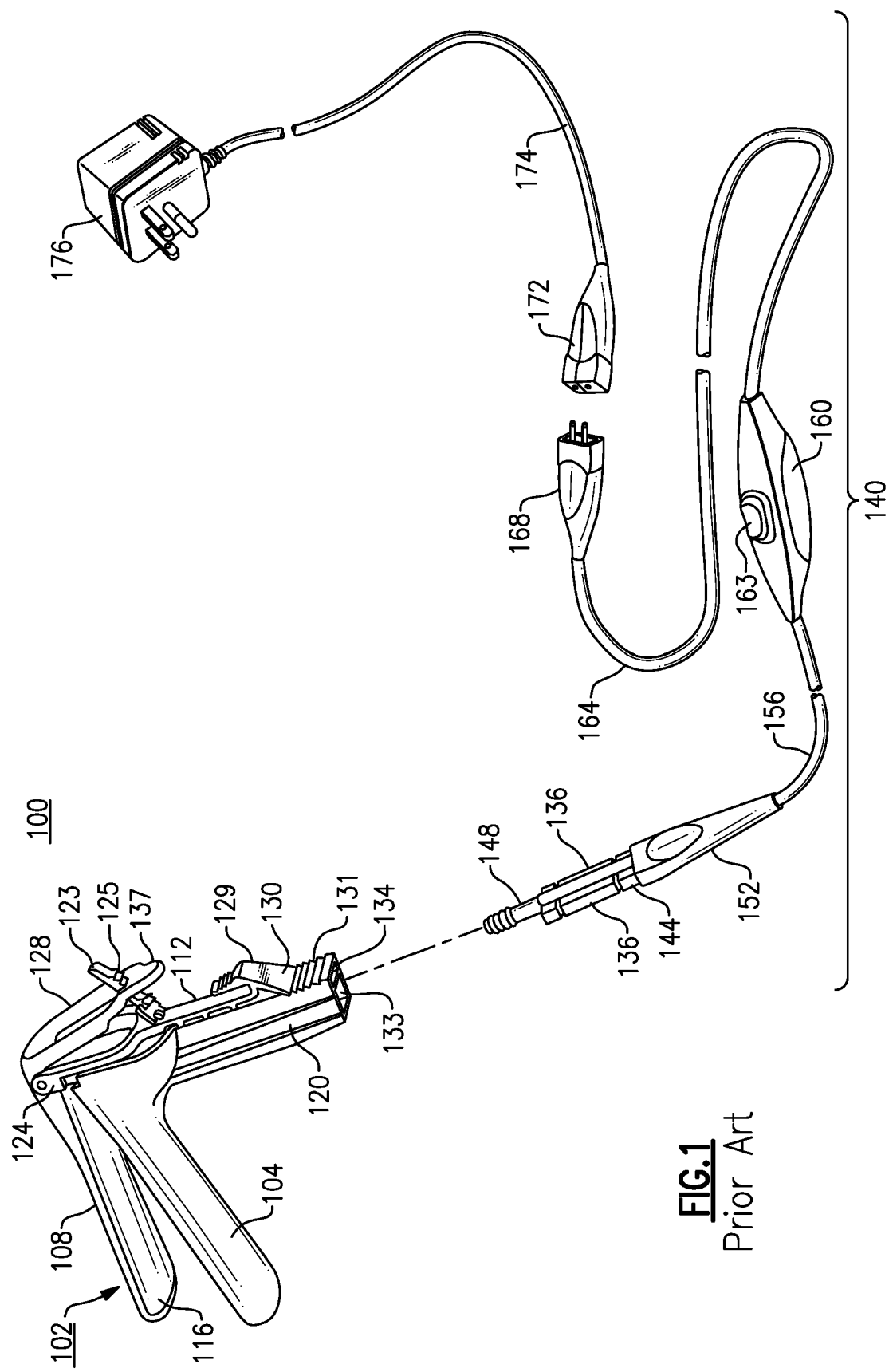
FIG. 1 is a perspective view of a vaginal speculum apparatus made in accordance with the prior art.

The following relates to an illuminated vaginal speculum apparatus as well as certain aspects of the apparatus that are herein described and based on various embodiments in accordance with this application. It should be readily apparent from the discussion that follows, however, that there are many variations and modifications that will be apparent to one of sufficient skill in the field, and that are intended to be within the scope of the inventive concepts. In addition, certain terms are used throughout the discussion, such as "top", "upper", "bottom", "lower", "above", "below", "proximal" and "distal", each of which are provided in order to provide a suitable frame of reference with regard to the accompanying drawings. These terms, however, are not intended to be overlimiting, except where so specifically indicated.

Referring first to FIGS. 1-4, there is shown a prior art vaginal speculum apparatus 100 that includes a disposable speculum 102 and a reusable illumination assembly 140. The disposable speculum 102 includes three (3) interconnected components; namely, a lower or bottom blade member 104, an upper or top blade member 108, and a slide member 112. Each of the two blade members 104, 108 is preferably made from a clear, durable plastic material, such as acrylic or polystyrene, wherein each of the lower blade member 104 and upper blade member 108 include a trough-shaped distal blade 116. A handle portion 120 extends vertically downward from the proximal or rear end of the lower blade member 104, wherein the handle portion is integrally molded as part of the lower blade member.

An intermediate portion of the slide member 112 is fitted within a guide slot (not shown) that is provided on a rearward facing side of the handle portion 120, the slide member further having a forked upper end or yoke 124 that receives the upper blade member 108, which is pivotally attached thereto, including a downwardly extending lever portion 128 extending from the proximal end of the blade member.

Figure 3:
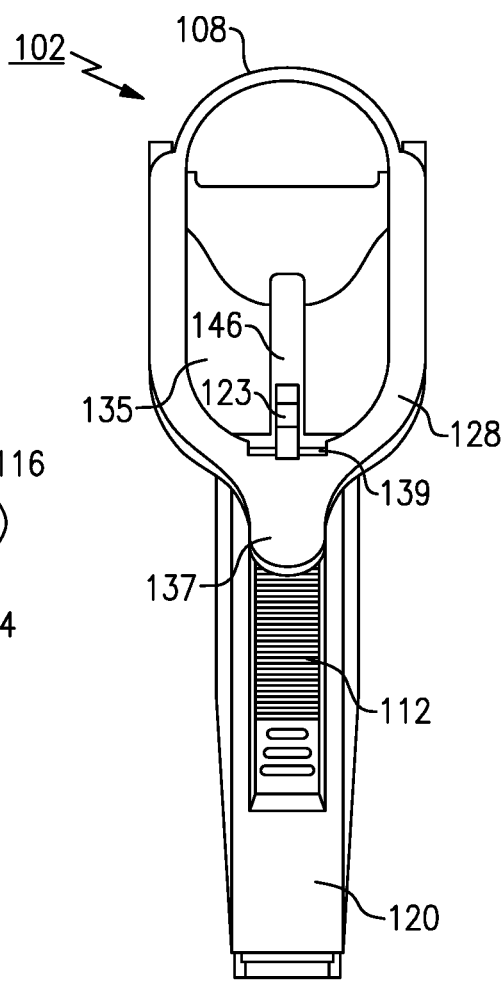
FIG. 3 is a rear view of the prior art disposable vaginal speculum of FIG. 2.

The lever portion 128 further includes an opening 135, shown only in FIG. 3, defining a user aperture between the yoke 124 and the lower and upper blade members 104, 108. The lever portion 128 terminates in a tab 137, the latter having an interior slot 139. The interior slot 139 is engageable with a flexible rear extending projection 123 of the slide member 112 provided beneath the yoke 124, and more particularly with a axially disposed set of ratchet teeth 125 that are provided on a lower facing surface of the projection. The ratchet teeth 125 of the flexible projection 123 are biased into the interior slot 139 of the lever portion 128 of the upper blade member 108. Angular articulation between the lower and upper blade members 104, 108 is initiated by applying finger pressure inwardly against the tab 137, causing the lever portion 128 to move along the set of ratchet teeth 125, and providing positive engagement therewith.

In addition, the slide member 112 further includes a lower tongue 129 having a single ratchet tooth 130 that engages with a set of corresponding teeth 131 that are provided on the rear exterior side of the handle portion 120 in order to provide relative vertical adjustment between the lower and upper blade members 104, 108, as needed. Additional details relating to the disposable speculum 100 depicted herein, including the adjustment of the upper and lower blade members 104, 108, can be found in U.S. Pat. No. 3,716,047, the entire contents of which are herein incorporated by reference.

Referring to FIG. 1, the handle portion 120 of the disposable speculum 100 includes a receiving cavity 133 that is sized for receiving a housing 144 of the reusable illumination assembly 140. The housing 144 retains a miniature incandescent lamp, such as a halogen bulb, which is sealingly retained within a distal portion 148 thereof. A proximal portion of the housing 144 extending from the receiving cavity 133, when assembled to the speculum 100, includes a strain relief 152 extending to an electrical cable 156 that further extends to a switch assembly 160. As shown in FIG. 1, an electrical cable 164 extends from the switch assembly 160 to a pronged plug 168 that engages a corresponding female plug 172, the latter being tethered by a corresponding cable 174 extending to a power supply transformer 176. The switch assembly 160 is defined by an elastomeric housing, having a depressible button 163 that is used to selectively energize the miniature incandescent lamp (not shown) contained within the distal portion 148 of the illuminator housing 144. Specific details relating to the illumination assembly 140 can be found in commonly assigned and co-pending U.S. Patent Application Publication No. 2004/0184288 A1, entitled: ILLUMINATION ASSEMBLY HAVING FLUID-TIGHT SEAL, the entire contents of which are herein incorporated by reference.

Figure 2:
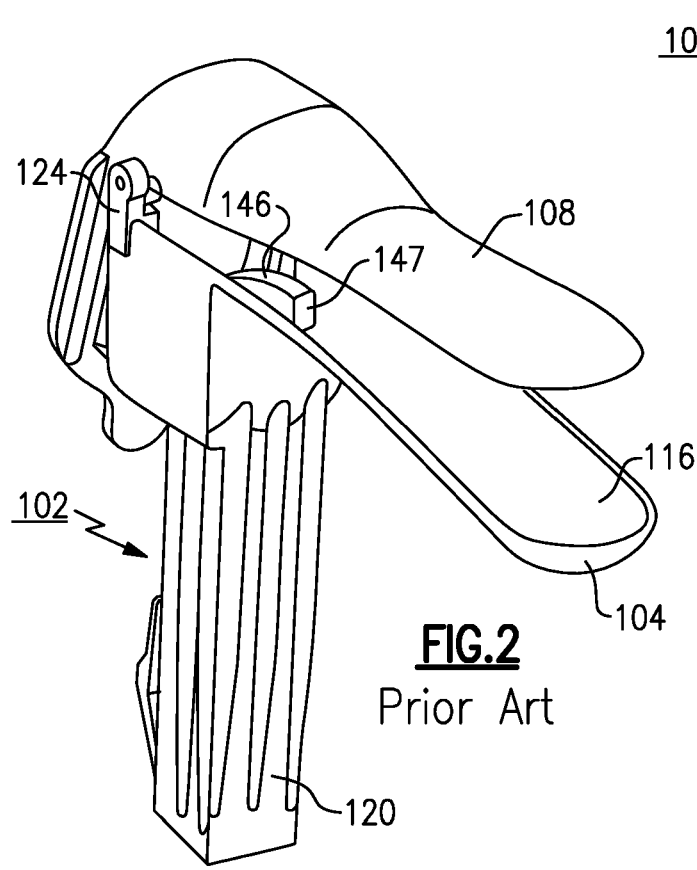
FIG. 2 is a front perspective view of a prior art disposable vaginal speculum used in the apparatus of FIG. 1.
Figure 27:
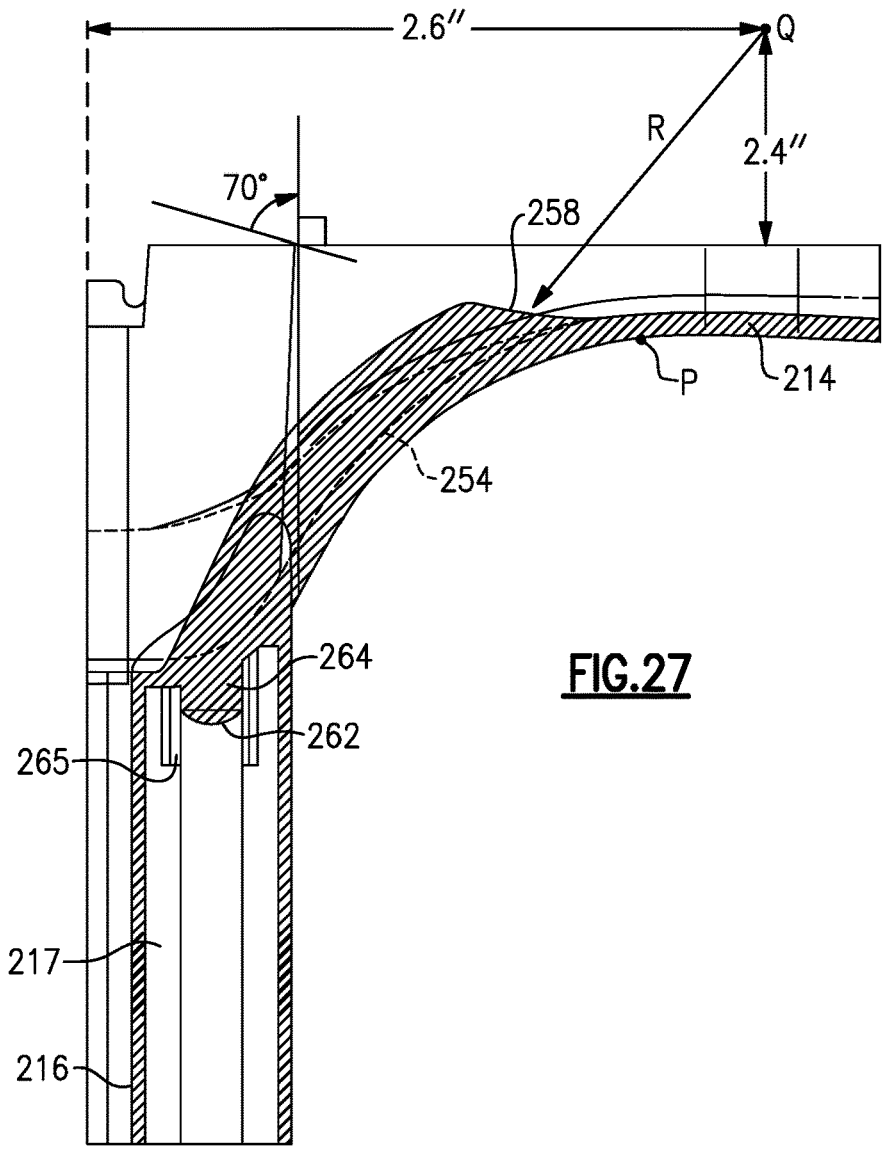
FIG. 27 is a side cross sectional view of the light pipe of the vaginal speculum of FIGS. 5-7.
Figure 28:
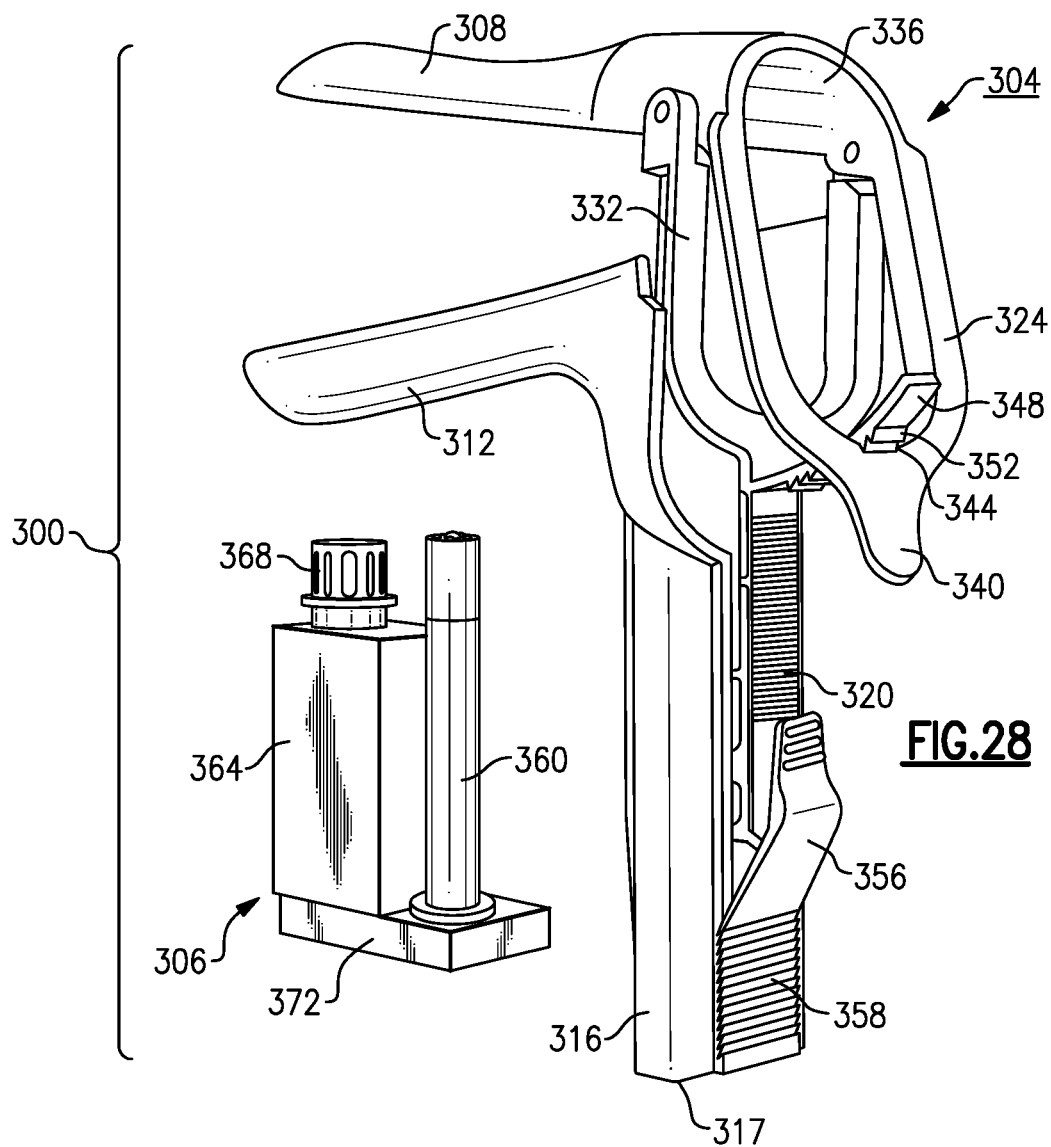
FIG. 28 is a partially unassembled view of a vaginal speculum apparatus manufactured in accordance with another embodiment.
Figure 29:
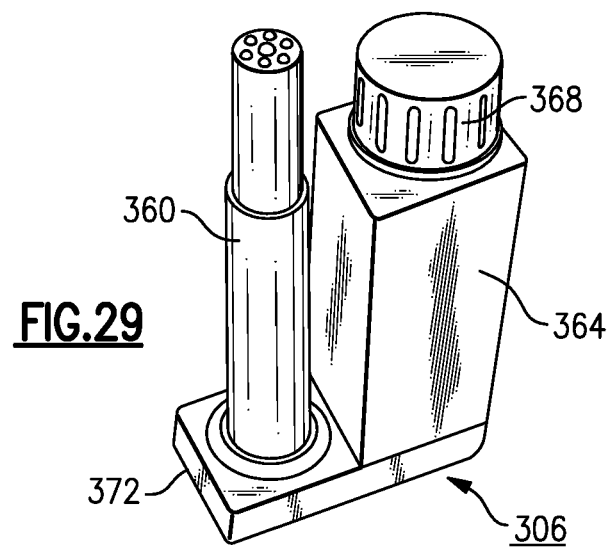
FIG. 29 is a top perspective view of an illumination assembly used in the vaginal speculum assembly of FIG. 28.

Referring to FIGS. 1-4, and in order to direct light from the illumination assembly 140 to the target of interest, a curved light tube or pipe 146 is provided, the light pipe having a proximal end disposed in the upper end of the handle portion 120 of the lower blade member 104, FIG. 2. When the housing 144 is inserted into the receiving cavity 133 of the handle portion 120 of the speculum 100, the contained miniature incandescent lamp is optically coupled to the proximal end of the light pipe 146. Emitted light is then directed by means of internal reflection through the length of the light pipe 146 to a flat distal light-emitting end 147 wherein the light is then distributed substantially along a longitudinal axis of the lower blade member 104 towards the target. The light pipe 146 is preferably molded directly into the lower blade member 104, wherein the proximal end of the pipe, as noted, is provided in the upper end of the receiving cavity 133 of the handle portion 120. In operation, light from the coupled incandescent lamp is collected by means of a plastic lens (not shown in these figures, but one of which is depicted in FIG. 27) that is also preferably directly molded into the proximal end of the light pipe 146. The lens has an appropriate curvature to collect the light from the lamp of the illumination assembly 140 and conduct same through the transmissive light pipe 146.

Though the light pipe 146 provides a coupling means for directing illumination from the contained miniature incandescent lamp of the illumination assembly 140, there are a number of issues relating to the instrument design of FIGS. 1-4. First, the design of the light pipe 146, as clearly shown in FIGS. 2 and 3, produces an obstruction for the user when viewed through the defined proximal opening 135 of the disposable speculum 100. More particularly, the reflective nature of the light pipe 146 produces glare from light that is reflected proximally towards the user from the distal end 147 of the pipe, wherein losses in efficient light transfer detract from illumination of the target. Additional inefficiencies are created in that the light pipe 146 produces a shadow when external illumination is used. In addition the distal end 147 of the light pipe 146, being flat and perpendicular to the centerline of the light pipe, produces a fluid-collection region that also blocks light from the target. A distal end 147 of the light pipe 146 as provided herein also produces difficulties in injection molding.

Referring to FIGS. 5-7, there is shown a vaginal speculum apparatus 200 that is made in accordance with a first embodiment. The vaginal speculum apparatus 200 includes a disposable speculum 204 and a illumination assembly 230 that is releasably attached to the handle portion 216 of the speculum. In this embodiment, the handle portion 216 is hollow, including an open bottom end extending into an otherwise enclosed receiving cavity 217. The handle portion 216, including the receiving cavity 217, is defined by a substantially rectangular cross section, the significance of which is detailed below.

Like the preceding, the disposable speculum 204 according to this embodiment is generally defined by an upper or top blade member 212, a lower or bottom blade member 214 (which integrally includes the handle portion 216), and a slide member 220. Each of the upper blade member 212 and lower blade member 214 are similarly constructed as described with regard to FIGS. 1-4, wherein each member is preferably formed from a durable clear plastic material, such as acrylic or polystyrene, and in which each blade member is further defined by a trough-shaped elongate section or blade 215, FIG. 7. The upper blade member 212 further includes a lever portion 224 extending downwardly at its proximal end thereof. The slide member 220, also preferably being made from a durable plastic material, though not necessarily clear, further includes a forked upper portion or yoke 228 that pivotally receives the upper blade member 212, as well as a flexible projection 225 that is disposed immediately beneath the yoke 228 and that extends rearward; that is, away from the handle portion 216. The flexible projection 225 is upwardly curved in a convex configuration (as depicted in FIG. 5), and includes a set of ratchet teeth 226 that are disposed along a bottom surface thereof.

The lever portion 224 is defined by a frame-like structure that includes an opening 221, defining an aperture through which the user can examine the patient through the upper and lower blade members 212, 214, as well as a bottom tab 227. Finger pressure on the bottom tab 227 allows the user to angularly articulate the speculum 200, in a manner similar to that described previously. According to this embodiment, an intermediate portion of the slide member 220 is movably (axially) disposed within a guide slot 223 extending over the entirety of the length of the rear side of the handle portion 216. Finger pressure on the lower tongue 229 of the slide member 220 permits engagement between a single tooth provided on the slide member 220 and a set of external teeth 222 provided on the proximal or rear side of the handle portion 216 and enables selective vertical articulation (spacing) of the lower blade member 214 with respect to the upper blade member 212 through selective movement of the slide member 220 and yoke 228. The guide slot 223 extends axially through the set of external teeth 222, improving moldability as opposed to the version shown in FIG. 1.

As described in greater detail below, the receiving cavity 217 of the herein described disposable speculum 204 is sized to interchangeably and releasably accommodate at least two illumination assemblies. As will be described in greater detail below, the illumination assemblies that can be interchangeably accommodated by the speculum can vary based on at least one structural and/or functional aspect, including size, type of power supply, and type of light source. In one variation, the receiving cavity 217 of the speculum 204 can interchangeably receive either a corded illumination assembly 140, FIG. 1, and similarly constructed assemblies utilizing a non-portable power supply (e.g., an AC power supply) or a portable illumination assembly such as, for example, the exemplary assembly 230 more completely shown in FIGS. 8, 11 and 12. Details relating to this exemplary version are now provided.

For purposes of reference, the cordless or portable illumination assembly 230 according to this embodiment is at least partially depicted in each of FIGS. 5-8, 11 and 12. In brief, this illumination assembly 230 is defined by a housing 236 having a substantially hollow interior that is sized to retain a number of components, as described below.

More specifically, the housing 236 is defined by a lower base portion 260 and a narrower extending upper portion 245. According to the present embodiment, the two portions 245, 260 are integrally formed by molding the housing, the housing being made from a durable plastic material. The narrower extending upper portion 245 is sized to fit entirely within the receiving cavity 217 of the handle portion 216 and includes a short tubular open-ended extending portion 238 projecting from a top surface 235 thereof.

Figure 8:
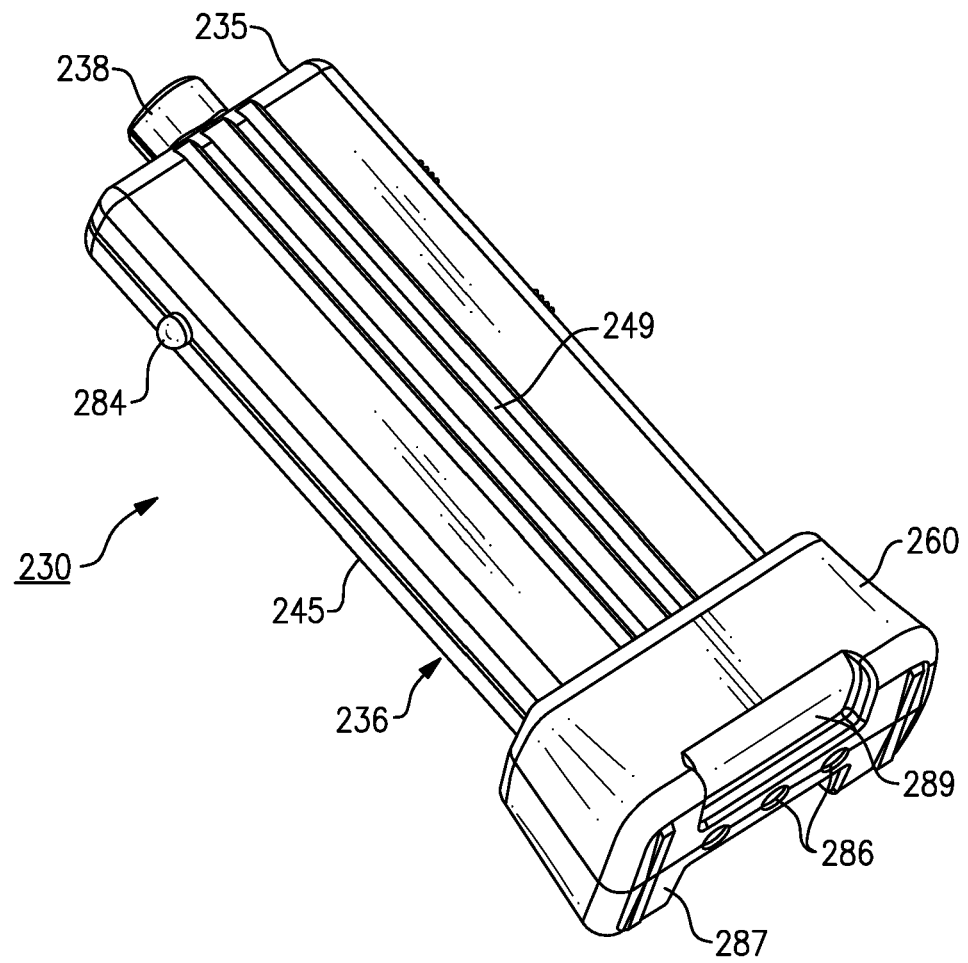
FIG. 8 is a side perspective view of an illumination assembly used in the vaginal speculum apparatus of FIGS. 5-7.

The upper portion 245 of the housing 236, as more clearly shown in FIGS. 8 and 11, also includes a set of parallel guide rails 249 (only one of which is shown in each of FIGS. 8 and 11) disposed along opposite sides of the housing that are used to align the assembly 230 with respect to the receiving cavity 217 of the speculum 204, permitting the assembly to be fitted within the cavity in two rotational orientations, 180 degrees spaced from one another, as described in greater detail below.

As noted, the substantially hollow interior of the housing 236 is sized to retain a number of components. More specifically and referring to FIG. 12, the tubular open-ended projecting portion 238 includes a spacer tube 241. A lens 259 is fitted to a distal end of the spacer tube 241. The lens 259, according to this embodiment, has a piano-convex configuration and is recessed within the tubular extending portion 238. This lens 259 is used to more efficiently direct illumination from a coupled light source to a light pipe 254, FIG. 27, described in greater detail in a later section.

An upper portion of the light source is also retained within the spacer tube 241. According to this embodiment, the light source is a miniature white LED 232, shown schematically in FIG. 22, such as a Model LXHL-PW01 white LED manufactured by Lumileds, Inc. The LED 232 includes a domed transparent envelope (not shown) at its upper end that is aligned with the lens 259 to provide optical coupling therewith. Moreover, the interior of the spacer tube 241 provides a surface that acts to direct stray light emitted from the envelope of the LED 232 and directs this light toward the lens 259. Alternatively, the light source can be a miniature incandescent lamp, such as, for example, a halogen bulb, arc lamp, or other suitable form of light source. In addition and though a single light source is depicted herein, multiple sources could be disposed within the housing 236, such as, for example, an array of LEDs having different colors (e.g., blue, green, white) to provide the cumulative effect of a "red" free filter.

A lower portion of the LED 232 is retained within a heat sink 244 made from a heat conductive material, such as, for example, aluminum, into which the lower end of the spacer tube 241 extends, as well as the extending electrical contact wires (not shown) from the LED 232. The heat sink 244 extends substantially across the width of the extending upper portion 245 of the housing 236, with the exception of a recessed portion 272 that accommodates an inner walled cavity 276.

Still referring to FIG. 12, the illumination assembly further retains at least one battery 242, in this instance, a single rechargeable lithium ion battery, such as a Model UF 812248P JFH battery, manufactured by Sanyo Corp, the battery being disposed in a compartment defined by a pair of tabs 280 for retaining the lower end of the battery. The upper end of the battery 242 is retained, according to this embodiment, against a portion of an inner wall defining the inner walled cavity 276, the latter being defined to receive a spring loaded plunger 284 beneath the heat sink 244, the plunger being aligned for movement in a direction that is perpendicular to the primary axis of the illumination assembly 230.

A printed circuit board 240 that includes components and circuitry for powering the LED 232 is disposed within the base portion 260 of the assembly housing 236 according to this embodiment. The circuit board 240 includes circuits for controlling the current required by the LED 232. According to this embodiment, the circuit board 240 includes a buck-boost constant current LED driver 251, such as a Model LTC3453EUF, used for this purpose. According to this embodiment, the circuit board 240 is retained and aligned within the housing 236 using a set of guide rails 285, though other suitable retaining means can be used. A set of charging contacts 286 are disposed immediately beneath the circuit board 240, each projecting through a bottom surface 287 of the housing 236. According to this embodiment, three (3) such contacts are provided, each of the contacts being equally spaced from one another, the purposes of which are detailed below. The wires extending from the lower portion of the LED 232 and extending through the heat sink are passed behind the battery 242 to the circuit board 240 and are connected therewith in a conventional manner, while wires extend from the circuit board 240 to the negative terminal of the battery 242.

According to one version as described below, the battery 242 is rechargeable wherein the housing 236 is sized and configured to permit recharging by attachment to a docking station. Details relating to the attachment of a housing of an illumination assembly is described in a subsequent embodiment, but for purposes of this discussion and referring back to FIGS. 11 and 12, the charging contacts 286 are engaged when the base portion 260 of the housing 236 is placed within a port of the docking station, the port being configured to retain same. The contacts 286 are engaged with the lower surface of the circuit board 240 to permit recharging of the contained battery 242, the latter being electrically connected to the circuit board. In the present instance, the three charging contacts 286 enable the housing 236 to be installed in at least two 180 degree-spaced orientations within a slot of the docking station and still enable recharging, the contacts therefore being position insensitive. In a preferred version and with reference to FIG. 22, the circuit board 240 further includes a short circuit/over current protection device 247 to prevent shorting and overcharging of the battery 242. According to this embodiment, a Model UCC3952PW-1 manufactured by Texas Instruments, Inc. is used, though other suitable devices can be substituted.

Figure 11:
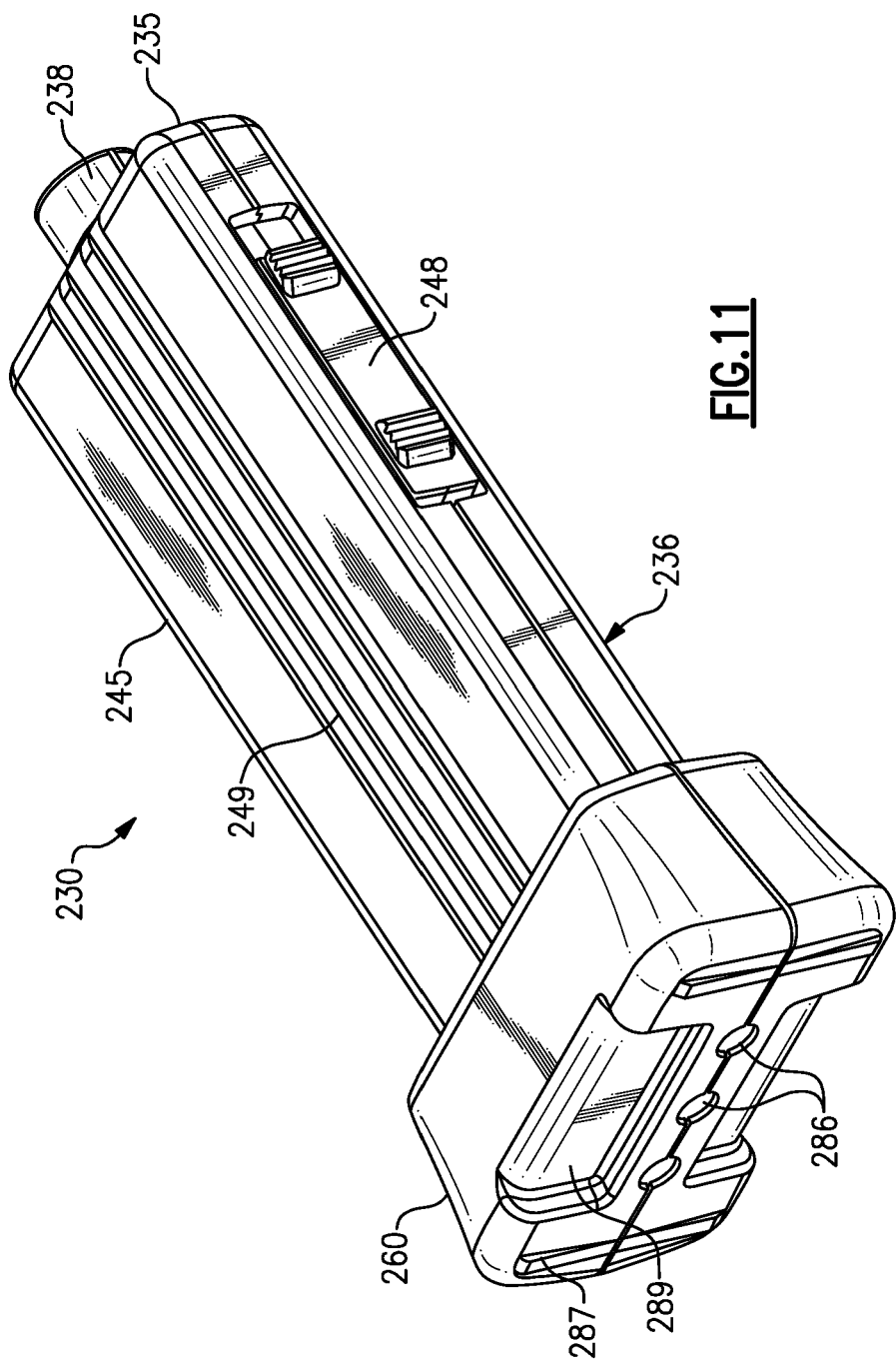
FIG. 11 is a bottom perspective view of the illumination assembly of FIG. 8.

According to the present embodiment, the base portion 260 further includes a pair of clamping recesses 289, FIG. 11, that are used in conjunction with the charging contacts 286 to allow a "clothespin" mechanism (not shown) to engage therewith for charging or for auxiliary power, as needed.

Figure 34:
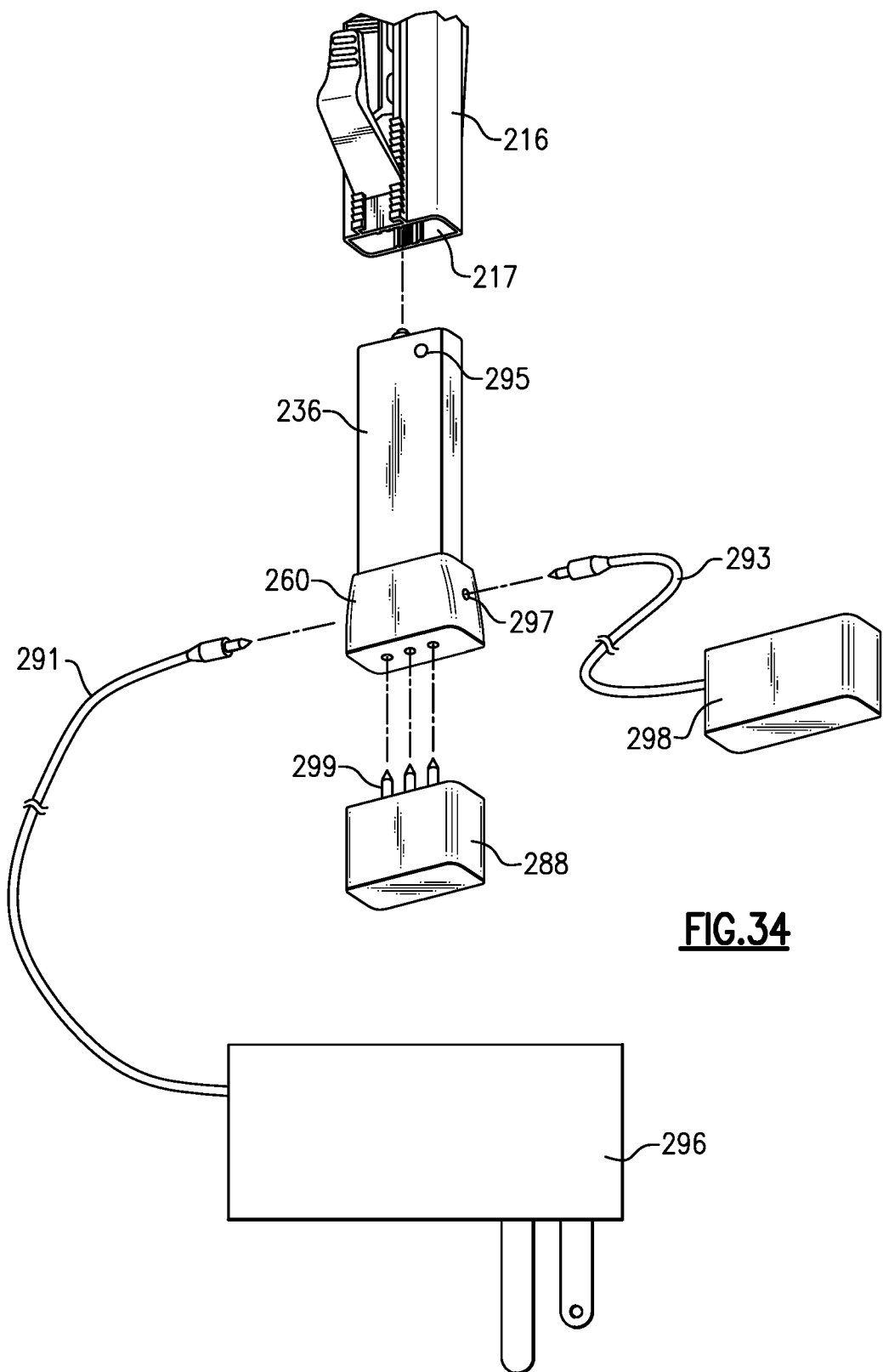
FIG. 34 is a diagrammatic view of alternative versions of power adapters used with the vaginal speculum apparatus of FIGS. 5-7.

It should be noted in passing that various other configurations could be used for auxiliary or for primary powering of the herein described illumination assembly 230. For example, and as shown in FIG. 34, the housing 236 can be configured alternatively to accommodate a plug-in cord 291 to a non-portable (e.g., AC) power supply by means of a transformer 296 in lieu of charging the battery 242, or when the battery is nearly or fully depleted as indicated by a low battery power indicator 295 provided on the exterior of the housing 236. According to this embodiment, the low-battery power indicator 295 is provided adjacent the top of the upper portion 245 of the housing 236, but could be otherwise disposed such as along the bottom surface 287, FIG. 12, for example, the indicator being connected in a conventional manner to the circuit board 240, as shown schematically in FIG. 22. Still further, it is not necessarily required that the battery 242, FIG. 12, be disposed within the housing 236 but could alternatively be disposed in a power adapter. As also shown in FIG. 34, the at least one battery 242 could be alternatively and separately contained within a power adapter 298 that is either tethered to the assembly housing 236, such as by means of a cable 293 that can plugged into a receptacle 297 in the base portion 260 or a power adapter 288 having a contained battery (not shown) that is mechanically engaged to the bottom surface 287, FIG. 12, of the base portion 260, such as using a set of pins 299 for engaging the charging contacts 286.

Figure 22:
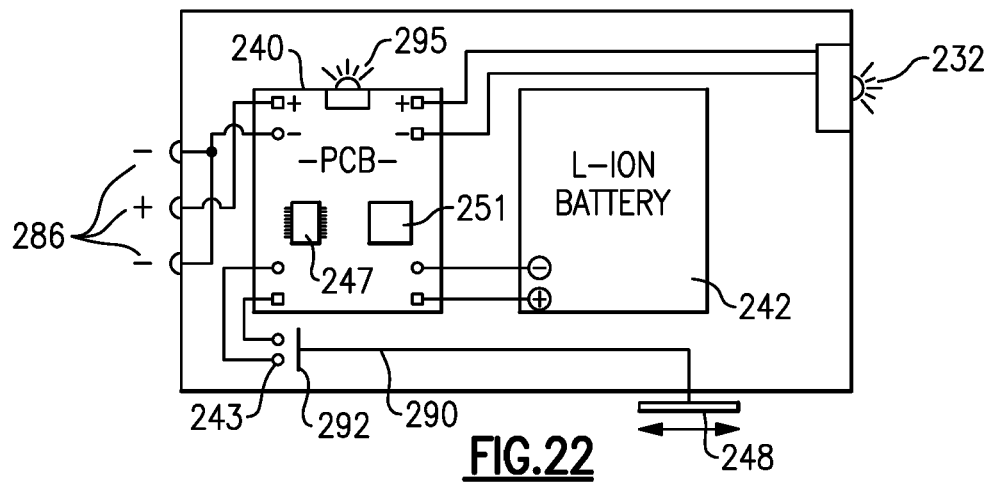
FIG. 22 is a functional electrical block diagram of the illumination assembly of FIGS. 11 and 12.

Referring to FIGS. 12 and 22 and according to the present embodiment, a conductive strip member 290 extends along an interior side wall of the housing 236, the strip member having a lower end 292 that is disposed adjacent to conductive contacts 243 of the circuit board 240. The conductive strip member 290 extends into the upper extending portion 245 to switch contacts 294 that are disposed on the interior side of a mechanical slider switch 248, the switch being disposed on the exterior of the housing 236, as shown most clearly in FIGS. 11 and 12. The switch 248 is configured, according to this embodiment, to permit automatic operation when the housing 236 is disposed at least a predetermined distance into the receiving cavity 217 of the handle portion 216, such as through engagement between an internal feature within the receiving cavity 217 and the exterior surface of the switch 248. In this instance, the spring-loaded plunger 284 is used in conjunction with the interior wall of the receiving cavity 217 to assist in engagement and in retaining the illumination assembly 230 in the receiving cavity 217.

According to this embodiment, the exterior surface of the slider switch 248 includes a pair of external projections 253, one on each of the upper and lower end of the slider switch to aid in manual operation of the assembly. According to this embodiment, engagement causes the switch 248 to move downwardly against the bias of a coil spring (not shown), biasing the switch in an Off position, and causes the lower end 292 of the conductive strip member 290 to electrically contact the conductive contacts 243 of the circuit board 240, thereby completing the circuit and causing the LED 232 to energize.

According to this embodiment, the illumination assembly 230 further permits the slider switch 248 to manually be preset to a locked position, in which the LED 232 can be energized prior to installing the assembly 230 into the receiving cavity 217, FIG. 5, of the speculum 204, FIG. 5. In this configuration, the slider switch 248 remains in the locked position based on the downward engagement of the switch 248 by finger pressure against one of the external projections 253 that locates a detent pin 261 attached to a leaf spring 263. Finger pressure of the switch 248 enables de-energization of the LED 232, but no automatic operation when the illumination assembly 230 is locked, irrespective of the position of the housing 236 within the receiving cavity 217, FIG. 5.

Otherwise and when not placed in the "locked" position, removal of the housing 236 from the receiving cavity 217 causes the switch 248 to be automatically de-energized (e.g., by sliding the switch 248 upward to the original position, moving the lower end 292 of the conductive strip member 290 out of contact with the circuit board 240) and thereby de-energizing the contained light source (e.g., LED) 232. It should be noted that other forms of switch assemblies, such as, but not limited to optical switches, magnetic/reed switches, and other mechanical switches (such as an ON/OFF throw switch that can be enabled with the speculum when engaged therewith to automatically or manually energize and de-energize the contained LED) can be utilized.

The cordless, self-contained and compact nature of the herein described illumination assembly 230 as well as the operation, including the locking feature of the exterior slider switch 248 further enable the herein described assembly to be useful independently as an examination light. The positioning of the LED 232 within the spacer tube 241 as well as the positioning of the collecting lens 259 permit illumination to be directly efficiently and uniformly emitted. The positioning of the contained LED 232 within the illumination assembly 230 and particularly within the heat sink 244 further provides a safety feature in that the exposed end of the tubular portion 238 can be brought into substantial contact with a patient without particular risk of injury. More specifically, because the coupled lens is interior to the tubular extending portion 238, the lens 259 cannot be readily contacted by a patient or user. The lens 259 is further isolated from shock loads if the illumination assembly 230 is dropped.

Figure 9:
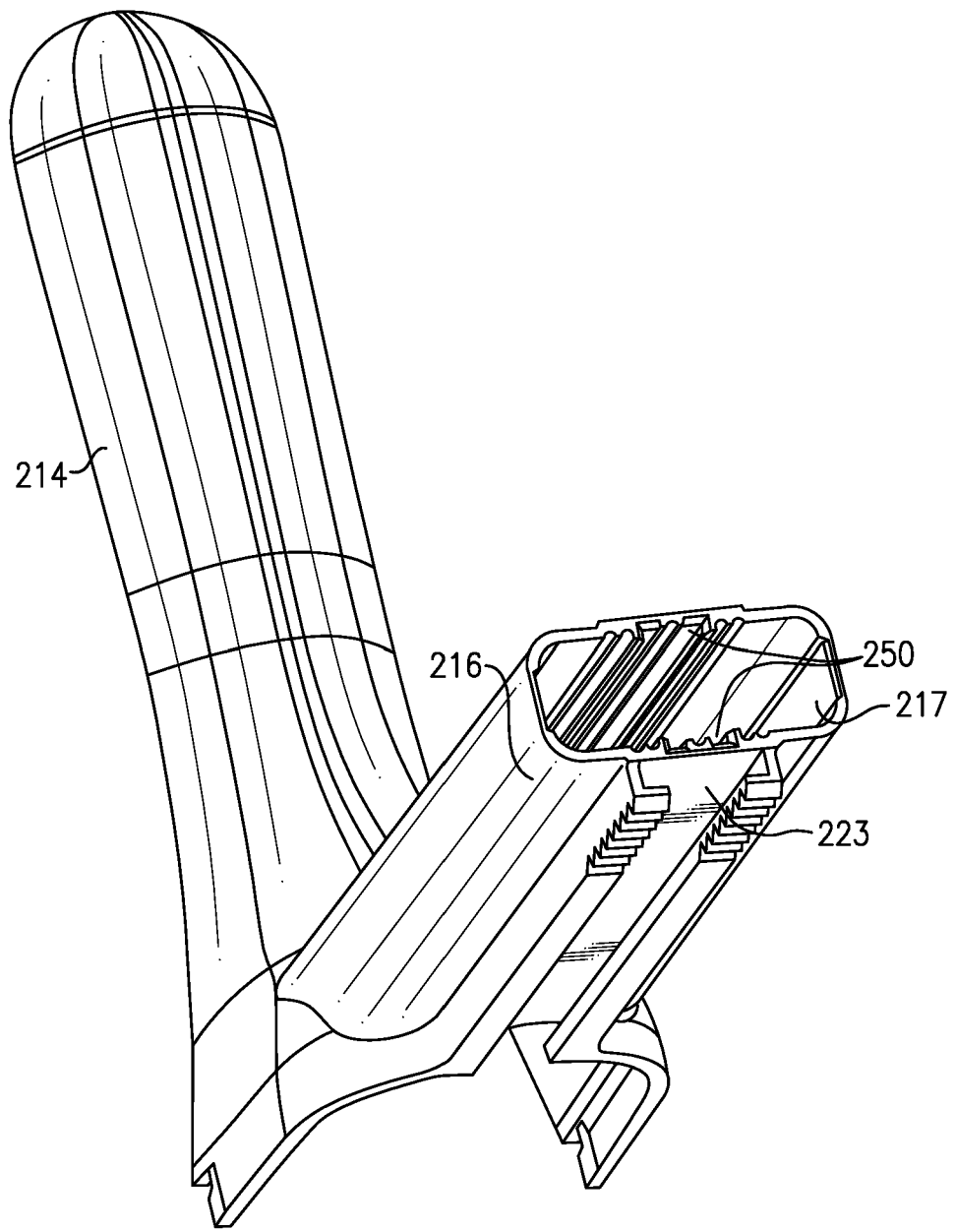
FIG. 9 is a bottom view, taken in perspective, of the vaginal speculum of the apparatus depicted in FIGS. 5-7.
Figure 13A:
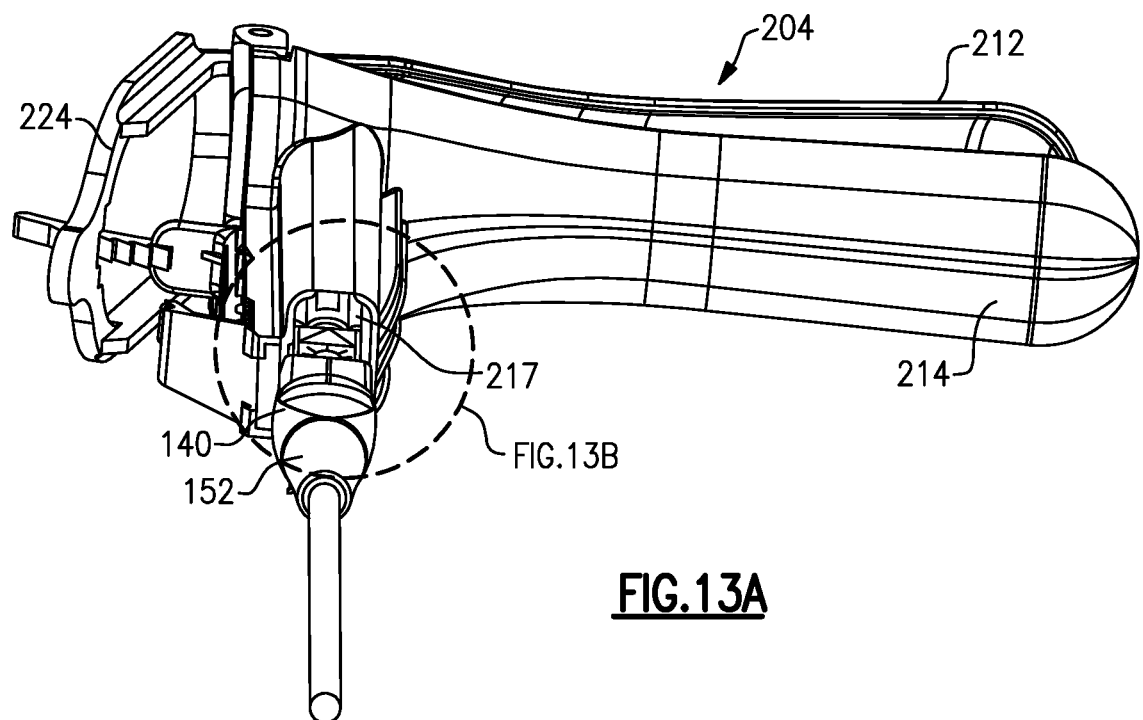
FIG. 13A depicts the interchangeability of a corded illumination assembly relative to the vaginal speculum of FIGS. 5-7.
Figure 13B:
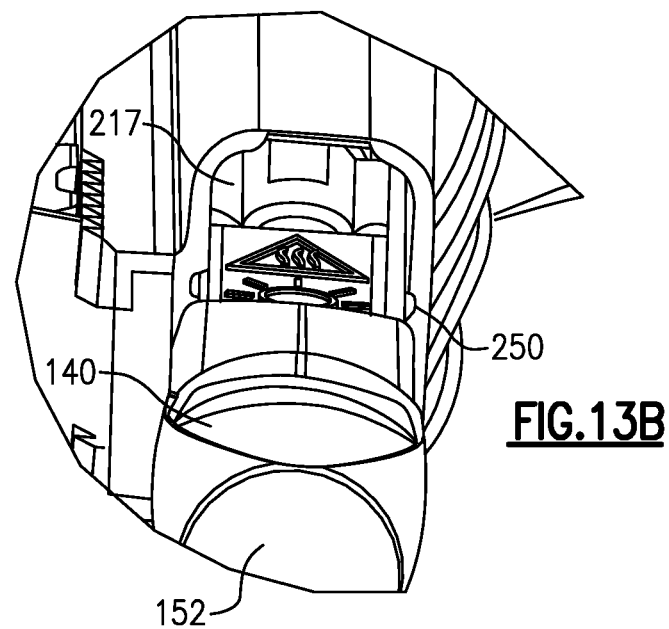
FIG. 13B depicts an enlarged view of a portion of the apparatus depicted in FIG. 13A.

Referring to FIGS. 13A and 13B and as noted, the receiving cavity 217 of the herein described vaginal speculum 204 further permits the releasable attachment of a corded illumination assembly 140, as previously depicted and shown with regard to FIG. 1. As shown in FIG. 9, the receiving cavity 217 includes a pair of opposed interior rail-like portions 250 that are formed between two substantially interior parallel sidewalls of the handle portion 216, the rail portions extending along substantially the length of the receiving cavity 217 that that are used to support and align the corded illumination assembly 140. The rail-like portions 250 are also used to align with the guide rails 249, FIG. 8, of the cordless illumination assembly 230, according to this embodiment in which the assembly can be mounted in at least two 180 degree spaced orientations.

The upper portion of either illumination assembly housing 236, 144, including the extending tubular open-ended portion 238 of the housing 236 or the distal portion 148, FIG. 1, of the illumination housing 144, FIG. 1 is received in the receiving cavity 217. A pair of oppositely disposed internal centering fingers 246 form a guide in order to center the distal portion 148, FIG. 1, of the corded illumination assembly 140, FIG. 1, within the receiving cavity 217 in either of the two 180 spaced orientations. Lateral spring-like protrusions 136, FIG. 1, disposed on the exterior of the illumination housing 144, FIG. 1, initially guide and orient the illumination assembly 140, FIG. 1, within the receiving cavity 133, FIG. 1. The protrusions 136, FIG. 1, also provide a securing function through a friction fit with the interior of the receiving cavity 133, FIG. 1.

In either instance, the corded illumination assembly 140 and the cordless or portable illumination assembly 230 can be installed into the receiving cavity 217 of the handle portion 216 in which the light source contained in each assembly is effectively coupled with the proximal end of a light pipe 254, FIG. 27, to uniformly illuminate the target. In the previously described cordless illumination assembly 230, the light is directed from the contained LED 232, in part using the reflective interior surface of the spacer tube 241 to the lens 259 that collects the light and then directs this light to a collecting lens 262, FIG. 27, as described below.

As previously noted, the upper portion 245 of the housing 236 is sized to fit entirely within the receiving cavity 217, wherein the handle portion 216 is defined by an aspect (width×depth) ratio of approximately 2:1 that substantially matches that of the upper portion 245, thereby defining a substantially close-contacting fit. A range of 1.25:1 to 3:1 is suitable to provide adequate stability and greater rigidity, while permitting effective hand held operation. The extending base portion 260 of the illumination assembly 230 further defines an effective length or working length, as measured from a point P, FIG. 6, to the bottom end of the base portion 260 of 5.50 inches, as shown in FIG. 6 by "A". For purposes of this discussion, point P is representative of the most proximal part of the speculum 204 typically in contact with a patient for purposes of examination and is located on the exterior underside of the lower blade member 214 along the elongate blade portion 215, FIG. 7, thereof, this point as noted being representative. More particularly, the point P is substantially located in the vicinity of the distal end of the light pipe 254, FIG. 27. A preferred range for "A" lies between approximately 3 inches to approximately 6 inches, according to this embodiment. In addition, the substantially rectangular end of the base portion 260 provides a stable base for the user as well as effective rigidity, wherein the apparatus 200, FIG. 5, can easily be hand-held.

Figure 26:
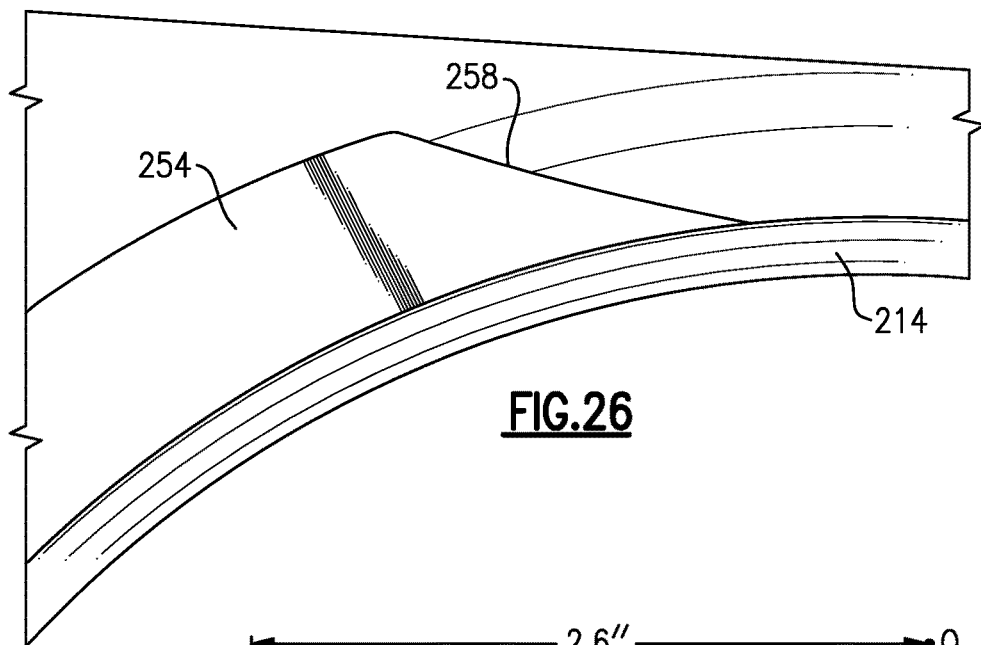
FIG. 26 is an enlarged view of a section of the bottom blade member of the vaginal speculum depicted in FIGS. 5-7.

Referring to FIGS. 25-27, the herein described speculum 204 includes a light pipe 254 having a proximal end 255, which is coupled to the light source of any of the interchangeably attached illumination assemblies 140 and 230. The proximal end 255 further includes a collecting lens 262. Rather than merely molding the lens into the proximal end, as done according to previous versions, the lens 262 according to this embodiment is molded as an inset in relation to the proximal end by means of a pedestal section 264 centered within an annular gap 265 formed between the set of internal centering fingers 246. The pedestal section 264 is reinforced within the annular gap 265 by at least one web (not shown) to prevent sagging. The collecting lens 262 by virtue of this construction provides improved optical coupling with the light source of either illumination assembly 140, FIG. 1, 230, FIG. 7. This improved optical coupling results from improved mechanical alignment of the illumination assembly with the lens 262, FIG. 27, and from more effective internal reflection at the cylindrical portion of the light pipe 254 in the annular gap 265.

Unlike that of the prior art, the distal end 258 of the light pipe 254 is also different than the version of FIG. 2. According to this embodiment, the distal end 258 is preferably molded into the lower blade member 214 and has a contoured configuration. By "contoured", it is meant that the surface of the distal end 258 has a defined shape that is not a 90 degree cut with respect to the axis of the light pipe 254. Therefore, it is intended that this term can cover both a range of angled surfaces as well as curvi-linear surfaces, such as spherical, parabolic and the like. The contour at the distal end 258 is preferably formed as a scallop, such as would be cut by means of an end mill or similar apparatus. Alternatively, the above modification can be placed into the molding process for the lower blade member 214 of the speculum 204, for example, if the speculum is being made from polystyrene, acrylic or similar materials. It will be readily apparent that the concept should not be restricted to these materials, but should also be applied to literally any light transmissive material.

The contour provided in the distal light emitting end 258 according to this particular embodiment is essentially a scalloped cut producing an inwardly (i.e., concave) curved portion having a radius of approximately 1.5 to 3.5 inches. The center of the radius is provided from a point Q, FIG. 27, that is approximately 2.6 inches as measured distally from the rear side of the handle portion 210 and approximately 2.4 inches, as measured vertically from the top of the trough 215, FIG. 7, of the lower blade member 214. These dimensions are shown in FIG. 27. It is noted that both dimensions locating point Q can be varied by approximately ±0.30 inches and still produce a desirable effect. The herein defined distal end 258 can alternatively be formed using an angled cut approximating that of the radiused scallop end described above. According to one version, a suitable angle of approximately 70 degrees, as measured clockwise from the proximal upper end of the cut with respect to the perpendicular is provided, thereby creating a downwardly extending face. The angle can vary from approximately 55 degrees to approximately 80 degrees for purposes of providing improved illumination spot quality while still reducing glare to the user. Illumination is passed through the entirety of the distal face such that fluid buildup will not significantly interfere with light transmission. This configuration further prevents glare from being reflected back to the user through the opening of the speculum and the contour itself further assists the user by being far less intrusive with regard to the field of view as seen through the opening. Alternatively and in lieu of providing a continuous contoured surface, the distal end 258 can be provided with a series of stepped surfaces (not shown).

In operation, the light emitted from the coupled illumination assembly 140, 230 is collected by the lens 262, FIG. 27, as positioned on the pedestal section 264, is reflected internally within the light pipe 254 and then is emitted from the distal end 258. The emission of the light is such that the light is directed towards the distal end of the elongate blade portion 215, FIG. 7, wherein significant light is not reflected back to the user viewing through the aperture or opening 221, FIG. 5.

In addition to the preceding, surfaces proximal to the light pipe 254 of the upper and lower blade members 212, 214 can be treated (e.g., as by frosting). Such treatment assists in reducing unwanted light (that is, light other than that received from the target) from being directed toward the user when the speculum 204 is used with an external light source. Similarly, the distal end 258 of the light pipe 254 can be provided with a variety of different optical surfaces through treatment thereof to smooth light output and control the distribution of illumination.

Figure 14:
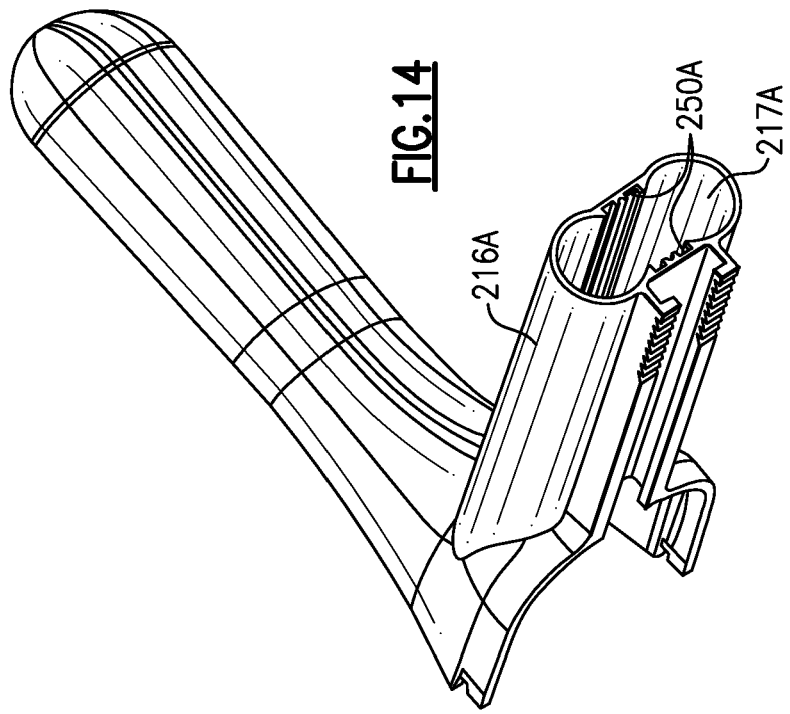
FIG. 14 is a bottom perspective view of an alternative vaginal speculum design.
Figure 10:
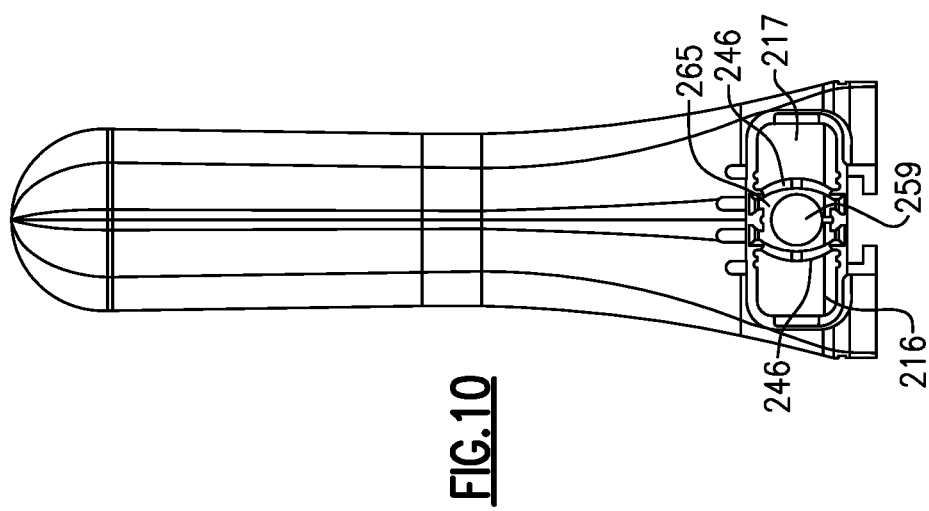
FIG. 10 depicts a partial bottom end view of the vaginal speculum of FIGS. 5-7.

FIG. 14 depicts an alternative design in which the receiving cavity 217A of a disposable speculum can be modified to accommodate a cordless illumination assembly (not shown) having a housing (not shown) that is configured to two AAAA batteries in side by side fashion. According to this version, a set of rails 250A are sized to separately accommodate the corded illumination housing, wherein the rails align the assembly as well as retain the assembly in the receiving cavity 217A. In this version as well as the preceding embodiment, the handle portion 216, FIG. 5, 216A, FIG. 14, can further include a series of parallel vertically arranged ribs 256, FIG. 7, disposed on a front facing side thereof, the ribs providing a means for dissipating heat developed by the retained illumination assembly, as well as providing a means for keeping a user's fingers away from "hot" surfaces. It has been determined that the provision of four (4) vertically extending exterior ribs 256, each having a depth of about 0.160 inches, a thickness of about 0.055 inches and having an equal spacing of about 0.150 inches provides additional protection. Other shapes can also be utilized.

At least one air gap is also developed, FIG. 13, in the receiving cavity 217 based on the size differential between the receiving cavity and the corded illumination assembly 140, the at least one air gap being used to channel heat away from the illumination assembly 140 or an alternative illumination assembly 140A, shown in FIG. 17 and described in greater detail below, that can include an LED as a light source in lieu of an incandescent lamp. Other means for dissipating heat can be utilized. For example, the housing 236 could at least partially contain a phase-change material (PCM), such as, for example, those manufactured by TEAP Energy in which residual heat developed or generated by the assembly is essentially stored during use and then later dissipated after use of the apparatus some later time after the illumination assembly has been deactivated.

In addition to the preceding and referring to FIGS. 32 and 33, a speculum adapter 281 can be used to facilitate attachment of a corded illumination assembly 140B, to the receiving cavity 217 of the speculum 204. The speculum adapter 281 according to the embodiment is a plastic-molded body that includes an external envelope 282 that is shaped essentially like that of housing 236. The speculum adapter 281 further includes an internal envelope 283 that is adapted in this instance to accommodate the housing 144B of a corded illumination assembly 140B containing a light source, such as an incandescent lamp or at least one LED (not shown). The speculum adapter 281 assumes a friction or snap fit or other substantial close contact with the interior of the receiving cavity 217. The internal envelope 283 of the adapter 281 retains the illumination assembly 140B without requiring predetermined alignment and enables optical coupling with the proximal end of the light pipe 254, FIG. 27. In operation, the speculum adapter 281 is disposed in one of two 180 degree orientations within the receiving cavity (not shown in this view) and the illumination assembly 140B is fitted into the internal envelope 283, either prior to placing the adapter 281 into the receiving cavity or afterward. The adapter 281 is sized such that the distal portion 148B of the assembly extends therethrough following assembly, allowing the contained light source to be optically coupled with the light pipe (not shown in this view). The adapter body provides a means for dissipating heat developed by the contained illumination assembly wherein at least a portion of the adapter 281 could also further be made from a phase change material (PCM), such as those previously noted.

Figure 23:
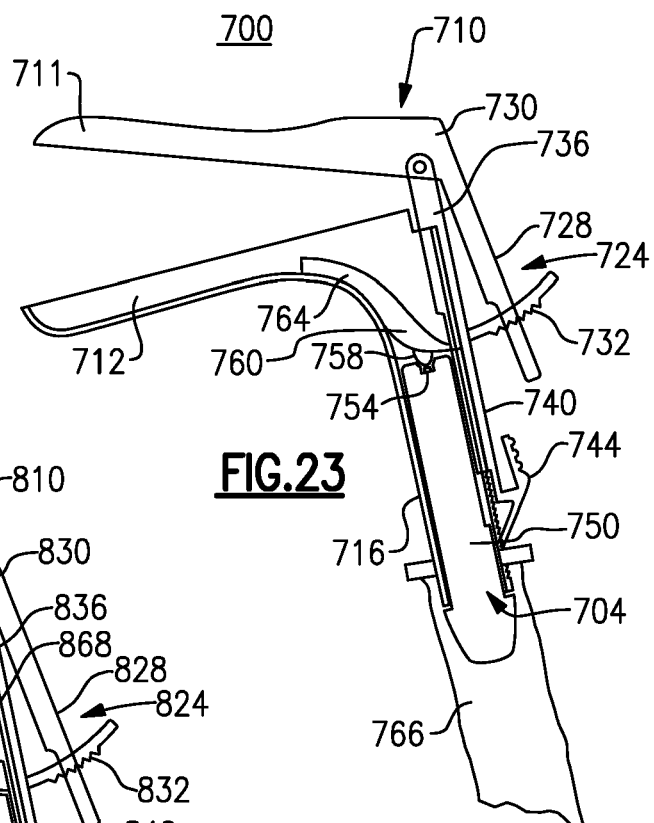
FIG. 23 is a side view of a vaginal speculum apparatus made in accordance with another embodiment, similar to that of FIGS. 16 and 17.

Due to the portable and non-tethered (cordless) nature of the illumination assembly 230, FIG. 7, according to this and other described embodiments that follow, the herein described speculum apparatus 200 is more versatile and can be used, for example, with bed-ridden patients based in part on the fact that there is no corded portion extending from the handle portion 216, 216A. As previously noted, the herein described illumination apparatus has an effective working distance A, FIG. 6, of approximately 3 to 6 inches that provides increased versatility and utility with regard to patients on a bed or examination table. As such, there are no issues such as those that are previously encountered with cabled or tethered assemblies. Either illumination assembly 140, 230 can be easily reused by removing same from the receiving cavity 217, 217A of the handle portion 216, 216A after an examination and discarding the speculum 204. Alternatively, the corded illumination assembly 140, FIG. 1, can be covered prior to use with a disposable sheath. An exemplary version of such a sheath is described in U.S. Patent Application Publication No. 2004/0186355 A1, entitled: PROTECTIVE SHEATH FOR ILLUMINATION ASSEMBLY OF A DISPOSABLE VAGINAL SPECULUM, the entire contents of which are herein incorporated by reference. A portion of an exemplary sheath assembly 1624 for this purpose is also depicted in FIG. 23 utilizing a prior art speculum 102 that includes a slot 134, FIG. 1, formed adjacent the receiving cavity 133 at the bottom end of the handle portion 120, the slot being sized to accommodate the disposable sheath assembly 1624. The sheath assembly 1624 includes a spool or ring member. This sheath assembly can be used in connection with the cordless illumination assembly or alternative sheath assembly designs can be used. As shown in FIGS. 7 and 7A, the extending base portion 260 of the illumination assembly 230, on the other hand, can be covered using a flexible sheath member 266 in substantial sealing relation. The sheath member 266 according to this embodiment need only conform to the base portion 260 since the remainder of the illumination assembly 230 is contained within the receiving cavity 217, wherein the sheath can be removed for disposal using a tab 268 that permits tearing of a disposed frangible tear strip 270.

Figure 15:
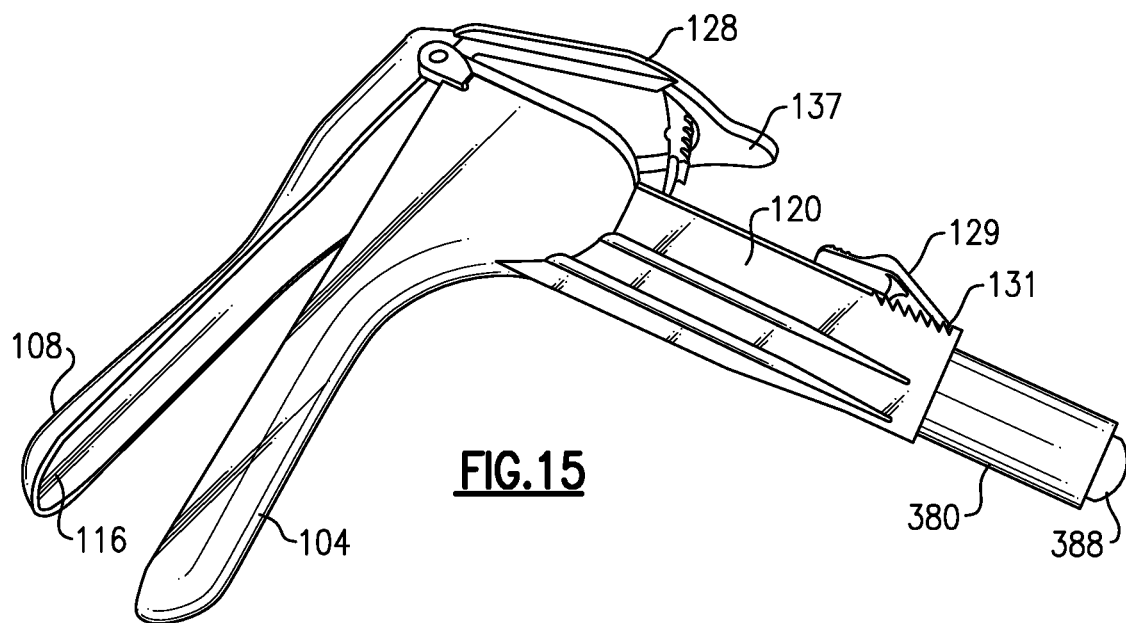
FIG. 15 is a perspective view of a vaginal speculum apparatus including a cordless illumination assembly made in accordance with another embodiment.
Figure 16:
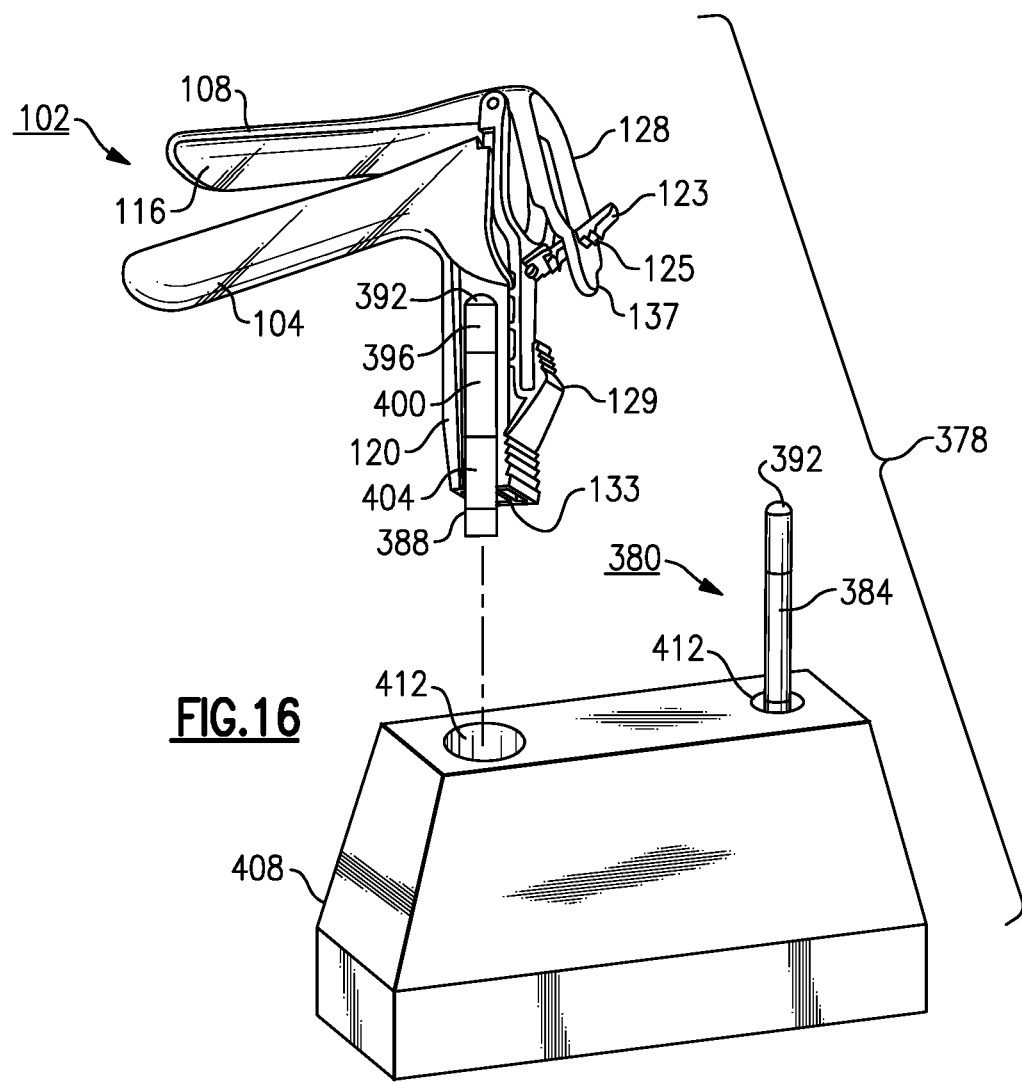
FIG. 16 depicts the vaginal speculum apparatus according to FIG. 15, including a docking station.

As noted, alternative embodiments of cordless (e.g., battery-powered) illumination assemblies are contemplated. Referring to FIGS. 15 and 16, there is shown a vaginal speculum apparatus 378 made in accordance with another embodiment. According to this embodiment, the disposable speculum 102 of the apparatus is literally identical in construction to that depicted according to FIG. 1. For this reason, the same reference numerals are used with similar parts for the sake of clarity. The disposable speculum 102 includes a lower blade member 104 having an integral handle portion 120 that includes a receiving cavity 133 formed therein. As previously noted, an illumination housing 144, as shown in FIGS. 1-4, but not shown in FIGS. 15 and 16, such as the 78810 model illuminator manufactured by Welch Allyn, Inc., can be releasably fitted into the receiving cavity of the handle portion 120 for coupling to the distal end of a contained light pipe.

A cordless illumination assembly in accordance with this embodiment can also be interchangeably attached into the receiving cavity 133 of the handle portion 120 of the speculum 102 without requiring modification to the speculum. Put another way, a corded illumination assembly housing and the cordless illumination assembly can be interchangeably fitted into the receiving cavity 133 defined by the handle portion 120 of the speculum 102 of FIGS. 15-16 according to this embodiment.

Still referring to FIGS. 15 and 16, the cordless illumination assembly 380 according to this embodiment is defined by a housing 384 wherein at least one extremely compact battery 404 is disposed in a lower or proximal end 388 of the housing. The at least one compact battery 404 may be a AAAA rechargeable battery, such as that available from Sanyo Corp (AAAA Size 1.2 Volt 300 mAh NiMH rechargeable battery). Other suitable miniature batteries can also be substituted. A miniature light source, in this case, a miniature LED (not shown but similar to that previously described as 232, FIG. 22), such as a Model LXHL-PW01 white LED manufactured by Lumileds, Inc. is disposed in a distal end of the illuminator housing 384 adjacent a collecting lens 392. If the at least one battery 404 is of the NiMH type, a circuit external to the battery may be needed in order to provide the correct current to the LED 232, FIG. 22. The circuit external to the battery 404 could be a constant current circuit set to deliver the current required by the LED 232, FIG. 22, similar to that previously depicted in FIG. 22. The NiMH battery described herein typically operates at 1.2 volts and the LED 232, FIG. 22, operates at 3.7 volts. Consequently, if fewer than three (3) NiMH batteries are used, the circuit to the battery 404 would be a voltage booster circuit.

The illumination assembly 380 further includes circuitry 400, enabling the voltage of the at least one contained battery 404 to be raised, if necessary, to that required by the LED 232, FIG. 22. Typically and as noted above, the voltage required to power the LED 232, FIG. 22, is about 3.7 volts. The LED described herein is rated at 1 Watt, has a light output of at least 20 lumens/watt and has a minimum service life of at least 1000 hours. An exemplary circuit for performing this function of permitting batteries to be electrically adapted is more fully described in U.S. Patent Application Publication No. 2004/0183482 A1, entitled: ELECTRICAL ADAPTER FOR MEDICAL DIAGNOSTIC INSTRUMENTS USING LEDS AS ILLUMINATION SOURCES, filed Mar. 20, 2003, the contents of which are herein incorporated by reference. A heat sink 396 provided in the illumination assembly housing 384 permits the heat generated by the LED 232, FIG. 22, and attendant circuitry 400 to be effectively dissipated. As noted above, the illumination assembly housing 384 is sized, owing to the size of the at least one battery 404 and the LED, to be fitted within the receiving cavity 133 of the handle portion 120 of the speculum 102 without any modification thereto and in which the components are arranged such that the proximal end 388 of the assembly housing 384 extends only marginally from the handle portion 120 when the illumination assembly housing 384 is inserted therein. The LED is optically coupled by means of lenses 392 (shown only in FIG. 16) and 262, FIG. 27, relative to the proximal end of a light pipe 254, such as previously described, or to an existing light pipe 146, FIG. 2.

The working life of the compact battery 404 described herein is relatively limited. Preferably, the apparatus is configured such that the battery is designed to operate over a life extending at least equivalent to that of a day of examinations. Referring to FIG. 16, a recharging or docking station 408 is provided, the station being connectable to an AC power supply (not shown) and including a number of receiving slots that define corresponding charging sockets 412. Each of the charging sockets 412 is sized for receiving the proximal end 388 of the illumination assembly housing 384. The lower extending or proximal end 388 of the illumination assembly housing 384 includes either sealed circuitry for charging a sealed inductive charge circuit (not shown) or contacts that are engaged by a pinned or other suitable connection with the recharging sockets 412, such as charging contacts 286, FIG. 12. Multiple recharging sockets 412 are provided, thereby permitting multiple illumination assemblies 380 to be stored and simultaneously charged for use in the herein described vaginal speculum apparatus 378. The docking station 408 can further include at least one charge level indicator to indicate when charging is complete. As previously noted, a similar docking station can be configured for use with any of the cordless or portable illumination assemblies described herein depending, for example, on the geometry thereof.

Figure 17:
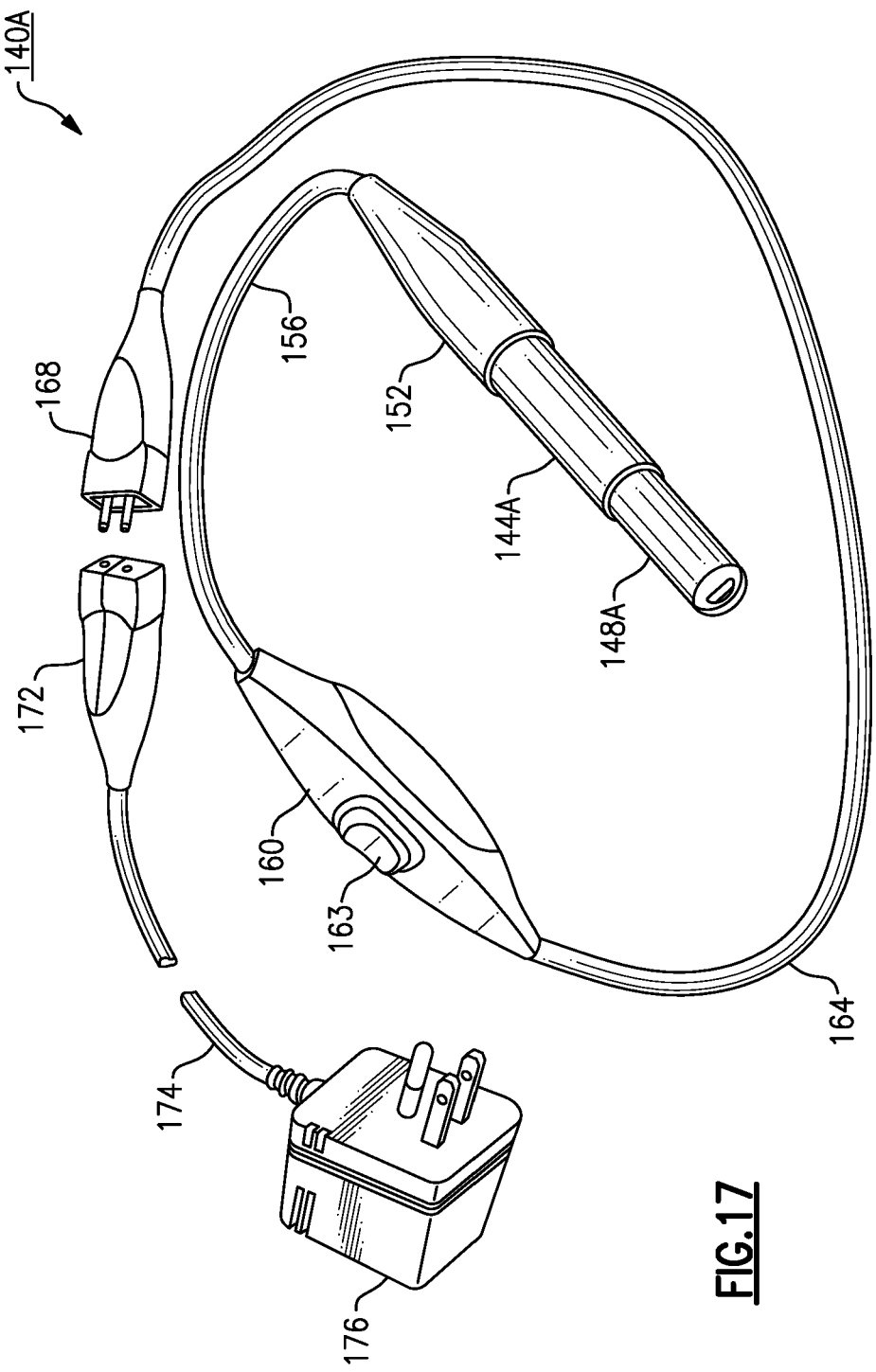
FIG. 17 is a perspective view of a corded illumination assembly made in accordance with another embodiment.

In addition and referring to FIG. 17, it will be understood that the corded illumination assembly 140 of FIG. 1 can also be reconfigured to provide an alternative LED light source in lieu of an incandescent lamp. According to this embodiment, the overall construction of a corded illuminator assembly 140A is similar and therefore the same reference numerals are used where applicable. An LED 232, FIG. 22, such as the Model LXHL-PW01 white LED manufactured by Lumileds, Inc. is disposed in a distal portion 148A of a housing 144A. The LED 232, FIG. 22, includes a domed transparent envelope (not shown) that extends from the distal portion 148A for optically coupling with the proximal end of a light pipe (not shown in this figure) disposed within the handle of a vaginal speculum, as previously described. The housing 144A is appropriately sized to be fitted within the receiving cavity 133, FIG. 1, defined by the handle portion 120, FIG. 1, of the speculum 102, FIG. 1, in a similar manner to that of the assembly shown in FIG. 1. The inclusion of the LED in lieu of a contained incandescent lamp provides a number of advantages; for example, increased working life, less heat generation, improved color rendering and less power consumption. As shown in FIG. 17 and similar to FIG. 1, a proximal portion of the illumination assembly housing 144A includes a strain relief 152 extending to an electrical cable 156 that further extends to a switch assembly 160. An electrical cable 164 extends from the switch assembly 160 to a pronged plug that engages a corresponding female plug 172, the latter being tethered by a corresponding cable 174 extending to a power supply 176. The switch assembly 160 is defined by an elastomeric housing, having a depressible button 163 that is used to selectively energize the contained LED 232, FIG. 22, within the distal portion 148A of the illumination assembly housing 144A.

In operation, each of the corded or tethered illumination assemblies 140, 140A or cordless illumination assembly 380 can be disposed interchangeably within the receiving cavity 133 of the disposable speculum 102 and coupled with the proximal end of the light pipe 146 wherein illumination is conducted through the light pipe by internal reflection to the distal end 147 towards the target. Though not shown, the housing 384 can be configured with a switch member to enable automatic energization of the contained light source when the housing is disposed at least a predetermined distance into the receiving cavity 133 through engagement with at least one feature on either the housing and/or the interior of the receiving cavity.

Referring to FIGS. 18-21, there is shown a vaginal speculum apparatus 1200 in accordance with another embodiment. The speculum apparatus 1200, like the preceding, includes a disposable speculum 1204 as well as an illumination assembly 1260 that is releasably attached to the speculum. In addition and also like the preceding, the speculum 1204 is configured to permit interchangeable attachment of either a corded illumination assembly such as 140, FIG. 1, or a cordless (portable) illumination assembly 1260. For purposes of this embodiment, only the cordless illumination assembly 1260 is herein discussed in detail.

The disposable speculum 1204 according to this embodiment is defined by an upper or top blade member 1212, a lower blade member 1214 that includes an integral handle portion 1216, and a slide member 1220. Each of the top blade member 1212 and lower blade member 1214 are similarly constructed as that shown in FIGS. 1-4 and are formed from a durable clear plastic material, such as an acrylic or polystyrene, wherein each blade is defined as a trough-shaped elongate member. The top blade member 1212 further includes a downwardly extending lever portion 1222 at the proximal end thereof. The slide member 1220, also made from a plastic material, further includes a forked upper portion or yoke 1226 that pivotally receives the lever portion 1222 of the top blade member 1212. The handle portion 1216, according to this embodiment and unlike the proceeding, does not include either a light collecting lens or a light pipe, as previously required. Rather, the upper portion of the interior of the handle portion 1216 is open.

Distally adjacent and part of the handle portion 1216 and disposed beneath the lower blade member 1214 and extending essentially vertically therebeneath, is a substantially cylindrical receptacle 1234 having an open end 1238 and a defined hollow interior that is sized for retaining the illumination assembly 1260 of the herein described apparatus 1200, as described in greater detail below. It should be readily understood, however, that other geometries can be substituted. The receptacle 1234 includes an upper portion 1242, shown only in FIG. 21, which according to this embodiment is opaque or black, and a lower portion 1246 which is made from a clear material, such as that of the lower blade member, the lower portion including the open end 1238. The receptacle 1234 is attached through an opening formed in the lower blade member 1214 through which the upper portion 1242 partially extends therethrough, or otherwise the receptacle can be integrally molded so as to form a portion of the lower blade member. According to another alternative version, the handle portion 1216 can be modified (e.g., widened—not shown) in order to accept the illumination assembly 1260.

Figure 18:
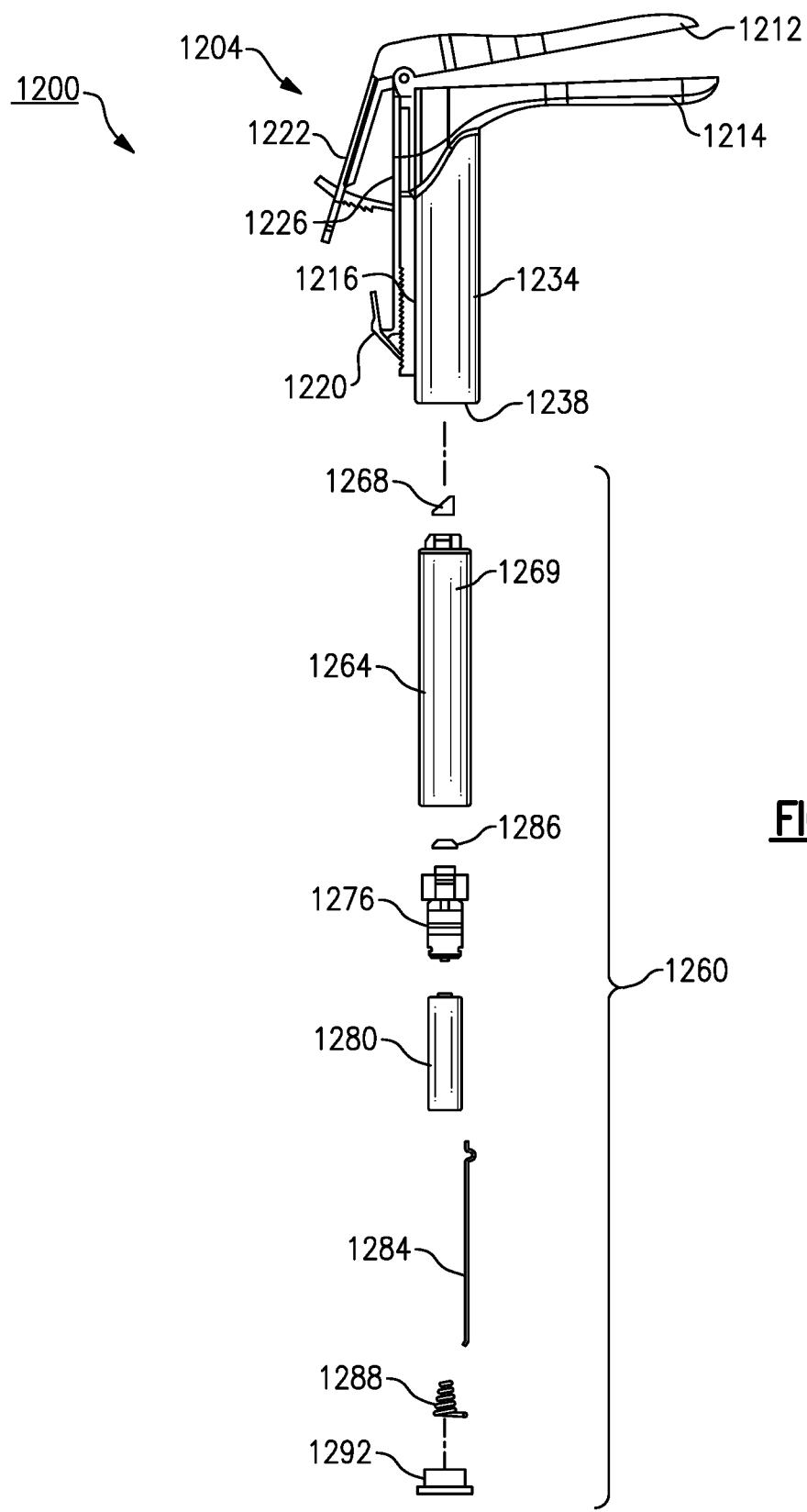
FIG. 18 is an exploded view of a vaginal speculum apparatus in accordance with another embodiment.

Referring to FIG. 18, an exploded view is provided of the illumination assembly 1260. According to this specific embodiment, the illumination assembly 1260 is defined by a hollow casing or housing 1264 sized to accommodate a number of components, including a prismatic member 1268 that is mounted to an upper portion 1269 thereof. The casing 1264 retains a miniature light source, which according to this embodiment is a miniature LED 1272, FIG. 19, such as a Model LXHL-PW01 white LED, manufactured by Lumileds, Inc. Alternatively, the light source can be a miniature incandescent lamp, such as a halogen bulb, an arc lamp, or other form of suitable light source. Still alternatively, different LEDs can be substituted, such as, for example, an array of different colored LEDs (e.g., blue, green) can be provided in the housing and configured in order to produce in combination a "red-free" filter.

Figure 19:
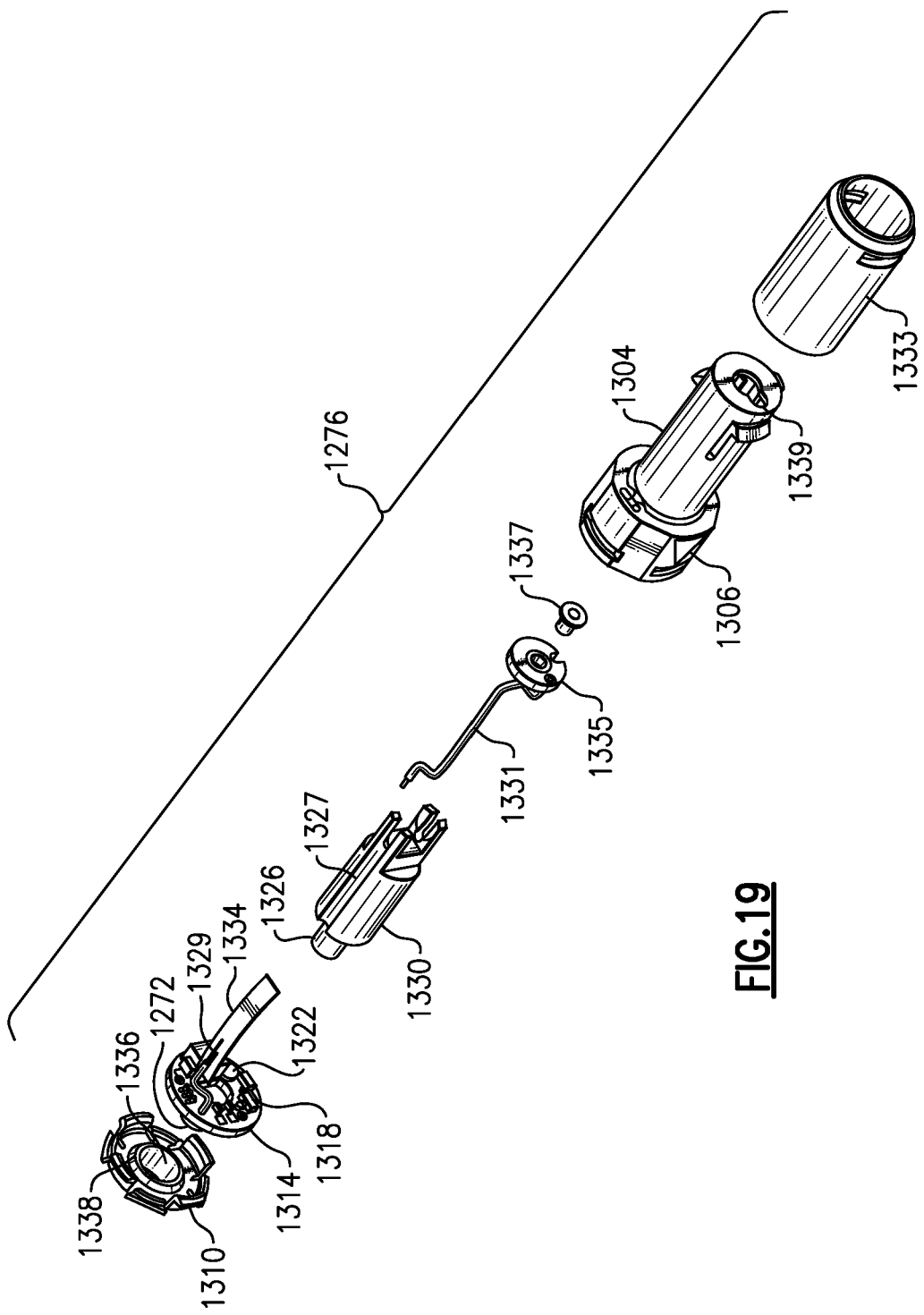
FIG. 19 is an exploded view of a light cartridge used in the illumination assembly of the vaginal speculum apparatus of FIG. 18.

Referring to FIGS. 18 and 19, the miniature LED 1272 is retained within a cartridge 1276. A rechargeable or other battery 1280 is disposed within the casing 1264 beneath the cartridge 1276, wherein a metallic conductive strip member 1284 is placed within the interior of the casing along the exterior of the battery and the cartridge to complete the circuit. The battery 1280 is retained by a spring 1288 disposed at the lower or negative end of the battery, the casing having an end cap 1292 for releasably retaining the above components. Between the prismatic member 1268 and the cartridge 1276, a condensing lens 1286 is provided according to this embodiment, for collecting and uniformly distributing light output of the miniature LED 1272 through the prismatic member, which includes a mirrored upper surface such that the light output is directed between the two blade members 1212, 1214. The lens 1286 according to this embodiment is piano-convex.

Details relating to the cartridge 1276 of the illumination assembly 1260 are now provided with reference to FIG. 19. The cartridge 1276 includes a cylindrical housing body 1304 which, according to this embodiment, is made from Radel R, polyphenylsulfone or other suitable polymer. Alternatively, the body 1304 can be fabricated from literally any electrical insulating material, wherein the miniature LED 1272 (only partially shown in FIG. 19) is disposed at a distal end 1306 adjacent a reflector cap portion 1310 that is attached in overlaying relation thereto. A printed circuit board (PCB) 1314 containing suitable electronics 1318 thereupon used for driving (e.g. powering) the miniature LED 1272 and for enabling the LED to be powered by the battery power source 1280, FIG. 18. A circuit for this purpose is described in commonly assigned and co-pending U.S. Patent Application Publication No. 2004/0183482 A1, previously incorporated by reference in its entirety. The PCB 1314 according to this embodiment, is disposed immediately below or proximal to the miniature LED 1272, and includes an opening 1322 for receiving the projecting portion 1326 of a heat sink 1330, retained by the housing body 1304 in order to dissipate heat that is generated by the miniature LED 1272, as well as heat also generated by the PCB 1314.

The heat sink 1330 includes an axial groove 1327 extending over the entire axial length thereof and is sized to retain one of a pair of electrical contacts. A first electrical contact 1329 extends from the proximal side of the printed circuit board 1314 and includes a lead wire and a strip member 1334. The strip member 1334 of this electrical contact 1329, when finally assembled, is sandwiched between a cartridge collar 1333 and the exterior of the cartridge body 1304. A second electrical contact 1331 is formed from a lead wire that extends axially from a battery contact board 1335, the board being retained within the bottom of the cartridge body 1304. According to this embodiment, the first electrical contact 1329 is a negative electrical contact while the second electrical contact 1331 is a positive electrical contact in which the positive terminal of the battery 1280, FIG. 18, is contacted by a rivet 1337 that is disposed within a chamfered hole 1339 at the bottom of the cartridge body 1304.

Still referring to FIG. 19, the reflector cap portion 1310 is defined by a through opening 1336 that is fitted about the lens envelope of the miniature LED 1272, the through opening according to one embodiment having an inwardly tapered surface 1338 that is used in order to effectively focus the light emitted from the miniature LED 1272 onto the condensing lens 1286, FIG. 18, which is fitted between the prismatic member 1268 and the LED 1272. The reflector cap portion 1310 according to this embodiment also recesses the LED lens and protects the lens from damage, such as from dropping the cartridge 1276, when removed from the illumination assembly casing 1264 for cleaning.

In passing, it should be noted that the cartridge 1276 is entirely portable and modular and therefore, for example, other LEDs or light sources could be substituted in the herein described illumination assembly by simple substitution of another cartridge having a different light source.

Referring to FIGS. 18 and 19, a negative electrical contact is created as the battery 1280 is pushed axially against the contact spring 1288 by means of a rotary switch assembly (not shown). As the switch is engaged, the strip 1334 of the electrical contact 1329 contacts the cartridge collar 1333 wherein the contact board 1335 within the cartridge body 1304 contacts the positive battery terminal, completing the circuit, and energizing the LED 1272.

It should be noted that other forms of switch assemblies, such as optical switches, magnetic/reed switches and/or other mechanical switches which automatically energize and de-energize the contained LED, and/or other forms of assembly can be utilized. It should be further note in passing that each of the preceding handle portions can include a feature, such as a groove or slot, which permits manual engagement by a user of an exterior switch member, such as 248, FIG. 12.

Figure 20:
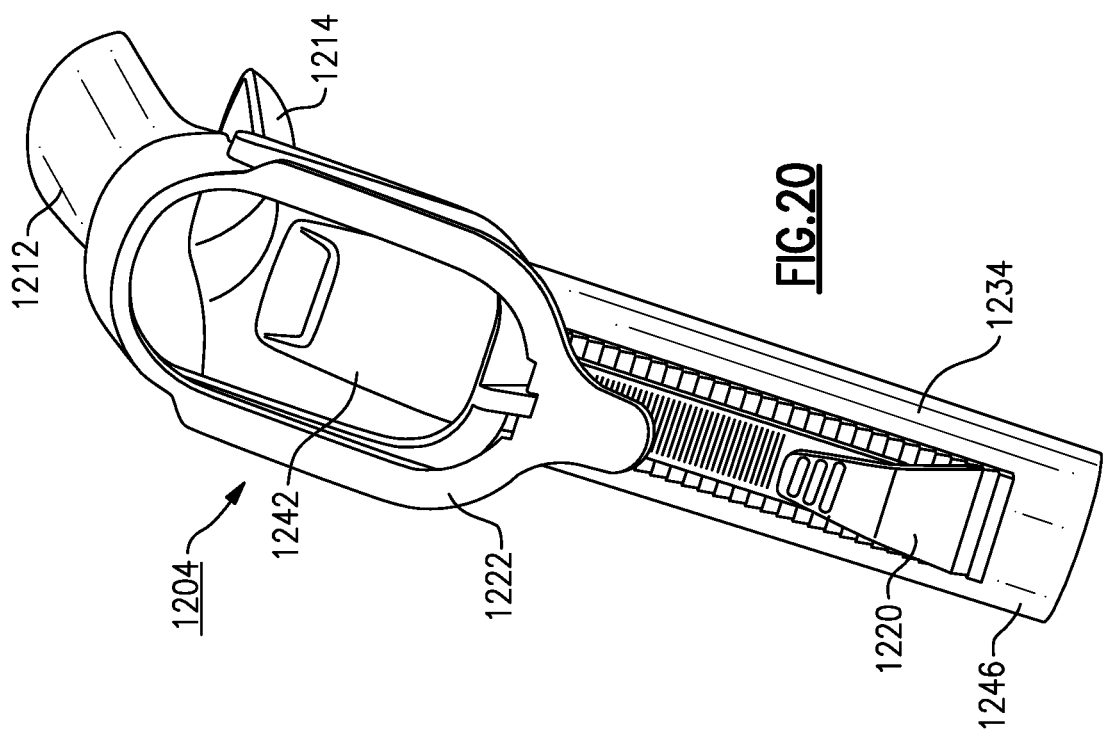
FIG. 20 is a rear perspective view of the vaginal speculum apparatus of FIG. 18 in an assembled condition.
Figure 21:
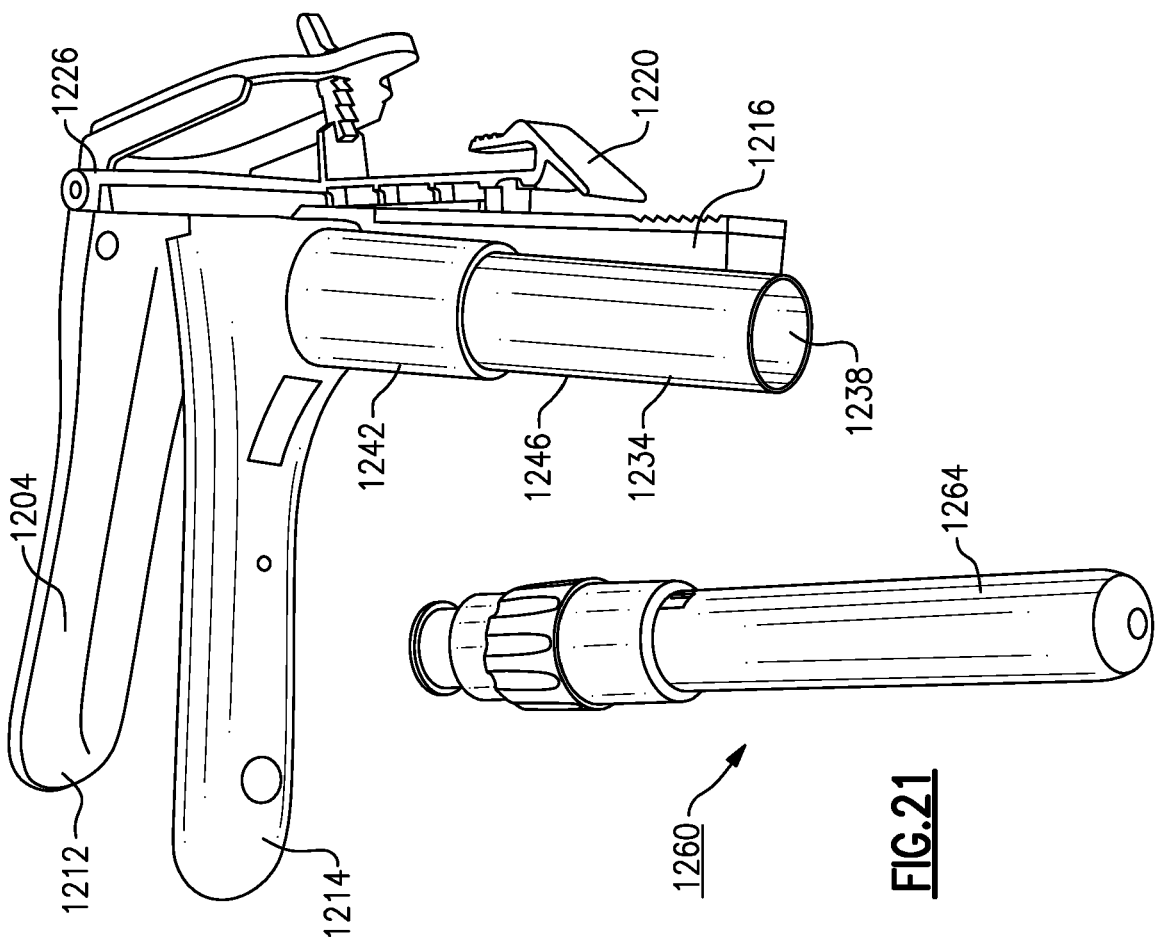
FIG. 21 is a side view of the disposable speculum and an illumination assembly of FIGS. 18-20 in an unassembled condition.

In operation, the illumination assembly 1260 is releasably attached to the cylindrical receptacle 1234 of the disposable speculum 1204 such that the prismatic member 1268 is placed into the upper portion 1242, FIGS. 20, 21, of the receptacle extending into the opening provided between the two blade members 1212, 1214, wherein the upper portion of the lower blade member 1214 has a distal facing opening (not shown). In this orientation, the light emitting surface of the prismatic member 1268 is directed axially towards the opening between the top and lower blade members 1212, 1214. The casing 1264 is accommodated by means of a friction or interference fit with the interior walls of the receptacle 1234, although other suitable releasable retention schemes, such as snap-fitting, can be used.

Figure 4:
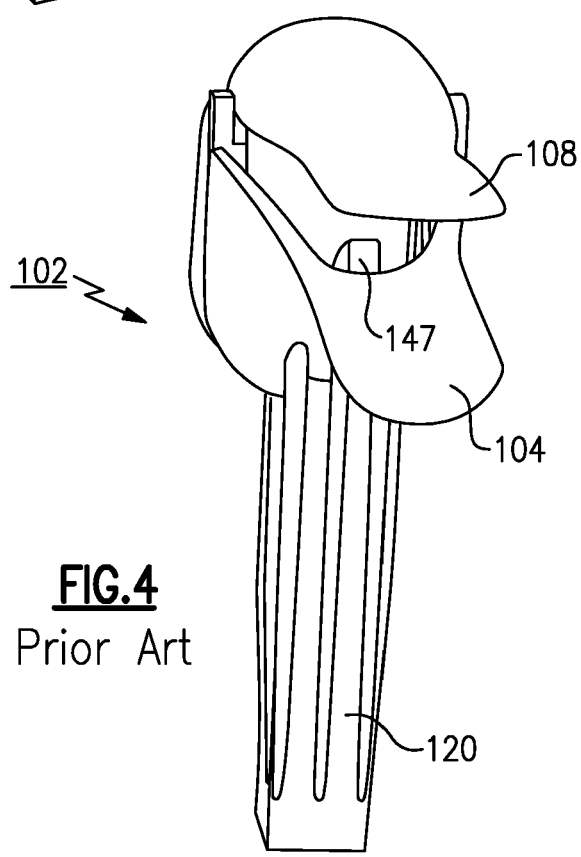
FIG. 4 is a front perspective view of the prior art disposable vaginal speculum of FIGS. 2-3.

Providing the present illumination assembly 1260 according to the present embodiment eliminates the need to mold or otherwise provide a light pipe or a similar light coupling means in the lower blade member 1214, such as provided in FIGS. 2-4. In addition, because the illumination assembly 1260 is battery powered, no cabling is required. Therefore, the herein described apparatus becomes more versatile, for example, permitting use for bed-ridden patients preventing entanglement with the clinician or patient, and preventing the risk of cross-contamination due to dirt collecting on cables. As in the preceding, the batteries are rechargeable and the illumination assembly can be placed within a docking station, such as depicted in FIG. 16, to enable recharging.

Another vaginal speculum apparatus 300 made in accordance with the present application is depicted in FIGS. 28-31. As in the preceding, the apparatus 300 includes a disposable speculum 304 and an illumination assembly 306 that is releasably attached to the speculum, the illumination assembly having a contained light source (not shown).

The disposable speculum 304 shown herein is similar to that described in FIGS. 1-4 in that the speculum includes an upper or top blade member 308 and a lower or bottom blade member 312, the latter including an integral handle portion 316 having a bottom end opening extending into a receiving cavity 317. A slide member 320 is attached to the rear side of the speculum 304, the slide member being fitted into a slot formed on the rear facing side of the handle portion 316 and including a yoke 332 at an upper end thereof that permits the pivotable attachment of the upper blade member 308 thereto. The upper blade member 308 further includes a lever portion 324 that extends downwardly from the proximal end of the upper blade member, the lever portion having an opening 336 defining an aperture that permits a user to view between the upper and lower blade members 308, 312 through the yoke 332 of the slide member 320. The bottom of the lever portion 324 includes a tab 340 having an interior slot 344 that engages with a curved member 348 rearwardly extending from the slide member 320, the rearwardly extending member being flexible and having a set of ratchet teeth 352 along a bottom surface thereof, permitting the selective articulation of the upper blade member 308 relative to the lower blade member 312.

The slide member 320 further includes a lower tongue 356 having a single tooth at its bottom end that engages with a set of ratchet teeth 358 provided on the rear facing side proximate the bottom of the handle portion 316. The tongue 356 can be retroflexed to release the tooth from the set of teeth 358 in order to permit vertical adjustment of the upper blade member 308 relative to the lower blade member 312. Further details concerning the design and the articulation of the disposable speculum 304 are provided in U.S. Pat. No. 3,716,047, previously incorporated herein by reference in its entirety.

Figure 30:
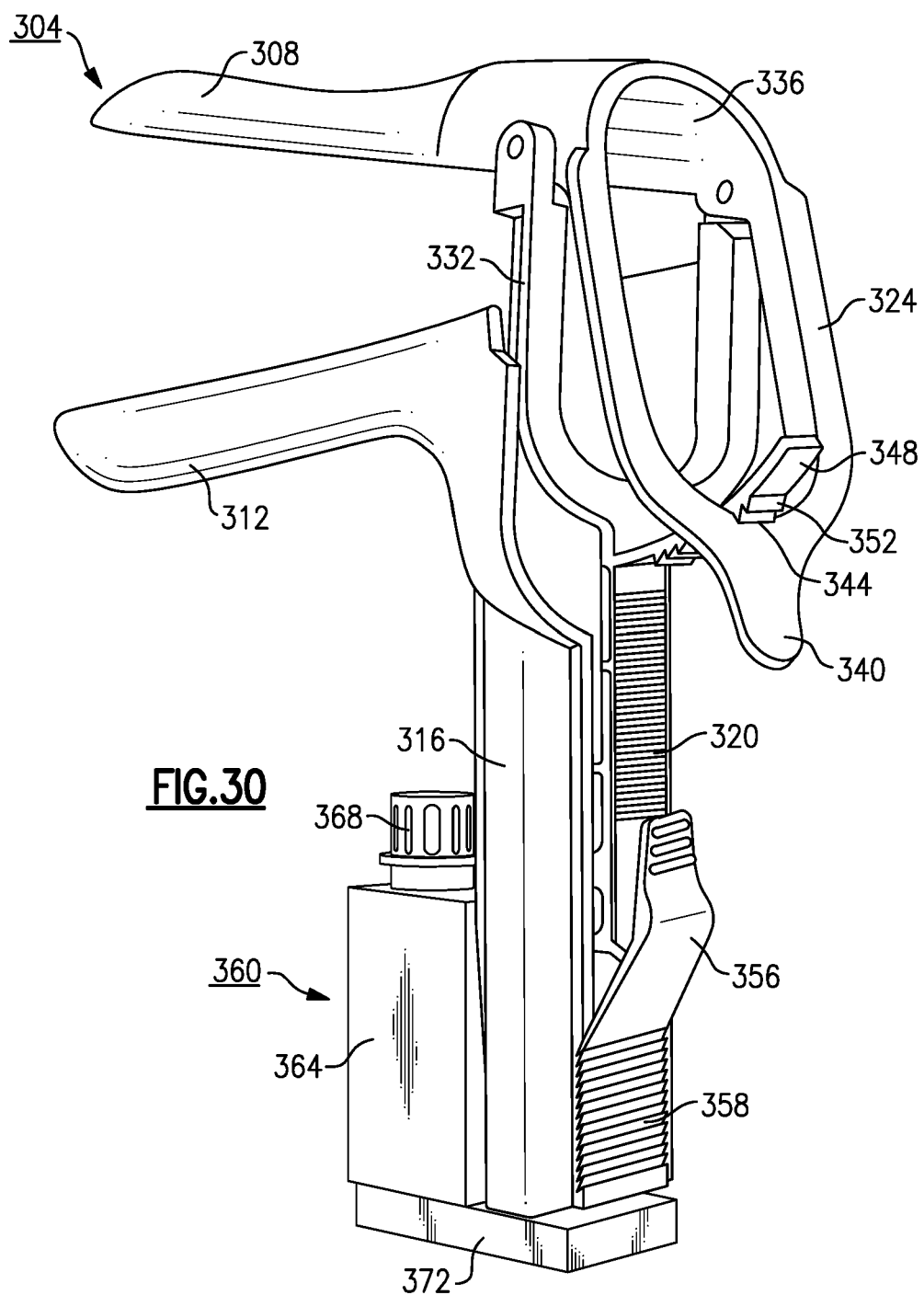
FIG. 30 is a side view of the vaginal speculum apparatus of FIGS. 28 and 29, shown in one assembled condition.
Figure 31:
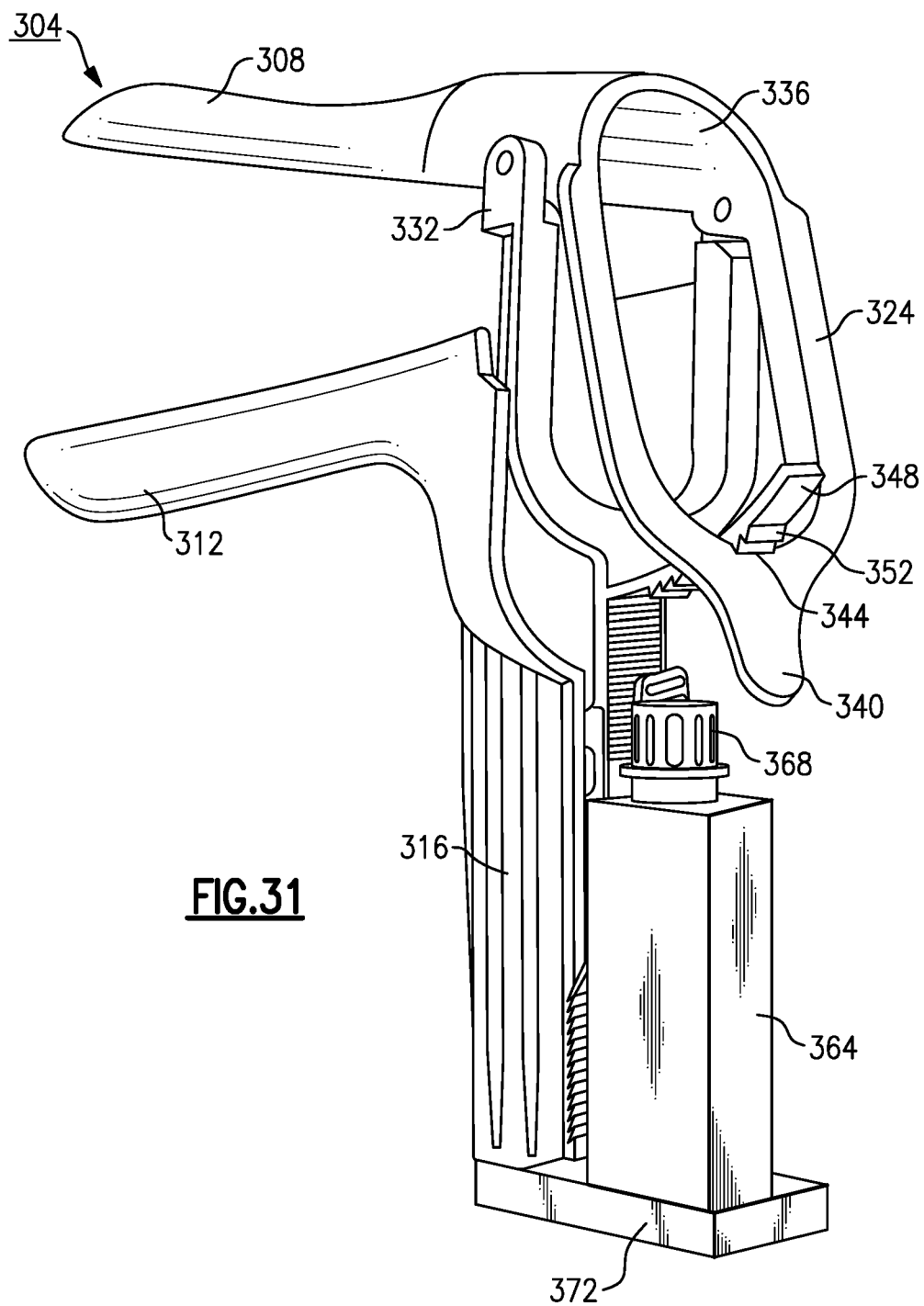
FIG. 31 is a rear perspective view of the vaginal speculum apparatus of FIGS. 28 and 29, shown in an alternative assembled position.

With this background, discussion is now made of the illumination assembly 306 in accordance with this particular embodiment. Still referring to FIGS. 28-31, the illumination assembly 306 includes an illumination source housing 360 that is disposed in side-by-side relation with a battery housing 364, each of the housings being supported by a base section 372. The illumination source housing 360 is sized to be fitted within the receiving cavity 317 of the handle portion 316 of the disposable speculum 304 while the battery housing 364 is contoured to be fitted in adjacent relation relative to the exterior of the handle portion 316, the battery housing assuming a parallel orientation thereto. As shown in FIGS. 30 and 31, the battery housing 364 can be provided either in front of or behind the handle portion 316 in terms of positioning.

The battery housing 364 is sized to retain at least one lithium ion or other form of battery (not shown), enabling the illumination assembly 306 to be used without tethering or connection to an exterior (e.g., AC) power supply. A rotatable switch 368 is located at the top of the battery housing 364, the switch being electrically connected to the contacts of the battery and the contained light source to enable energization of the contained light source (e.g., a white LED) within the illumination source housing 360. Electrical connection is effected by a metal tube that moves vertically when the switch 368 is rotated, the vertical motion causing the tube to touch a metal contact inside the housing 364. Alternatively, other switches can be used with this embodiment of the illumination assembly 360. For example, a switch of the type shown in FIGS. 11 and 12 can be used, that switch having the advantage of being enabled automatically (by sliding downward) when the illumination assembly 306 is inserted into the receiving cavity 317 of the handle portion 316 and disabled automatically (by sliding upward to the original position under the action of a spring internal to the housing 364) when removed from the receiving cavity 317.

The light source is preferably disposed in relation to the distal end of the illumination source housing 360, according to this embodiment, enabling the light source to be coupled with the light pipe 254, FIG. 27, at the distal end of the receiving cavity 317 of the handle portion 316 in the same manner as previously described, the light pipe preferably having a scalloped, curved or otherwise contoured distal light-emitting end 258, as previously described and shown in FIGS. 25-27.

Figure 35:
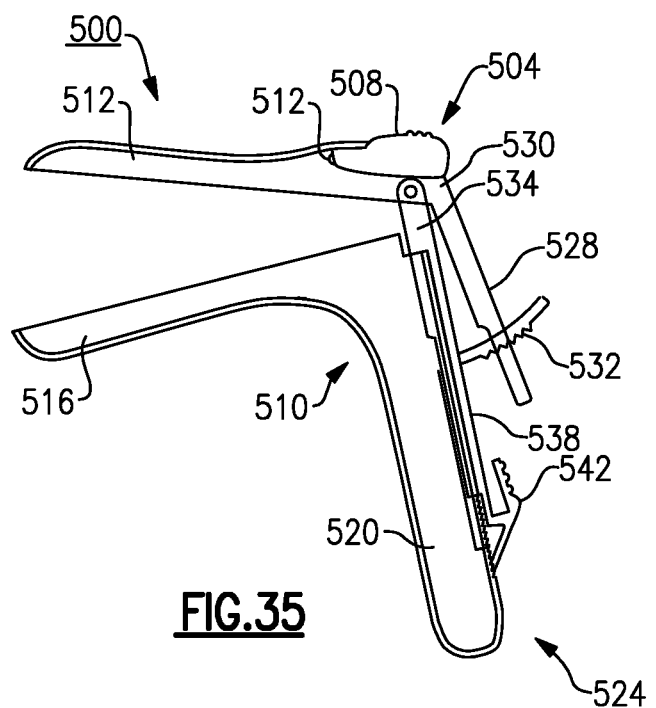
FIG. 35 is a side perspective view of a vaginal speculum apparatus made in accordance with another exemplary embodiment.

Alternatively, other exemplary embodiments of portable illumination assemblies for use with a disposable speculum are shown in FIGS. 35-39. Referring to FIG. 35, a vaginal speculum apparatus 500 includes an illumination assembly 504 comprising a compact housing 508 that can be disposed within the top blade 512 of a vaginal speculum 510 such that a contained white or other color LED or other miniature contained light source (not shown) is aligned along the longitudinal axis of the top blade. The speculum 510 is similar to those previously described including the top blade 512 and a lower blade 516 having a downwardly depending handle portion 520. An articulation mechanism 524 is also provided as previously described in which a lever portion 528 extending from a proximal end 530 of the top blade 512 is engageable with teeth provided on a flexible projection 532 extending outwardly from the lower portion of a yoke 534 of a slide member 538. A lower tongue 542 enables adjustable movement of the slide member 538 along the exterior of the handle portion 520 in which relative movement can be provided between the blades 512, 516 to dilate a patient. The housing 508, which can be reusable or expendable according to this embodiment, further contains at least one battery and resident circuitry for powering the LED. The housing 508 is releasably attached to the top blade 512 according to this embodiment although the housing can be alternatively positioned relative to either the top blade or the lower blade 516 of the speculum 510, as discussed herein. Clips, fasteners or other conventional means can be used to releasably attach the housing 508 to the blade 512, wherein the illumination assembly 504 can also be used separately as an examination light when detached. At least one optical element 526, such as a focusing lens, may be disposed in front of the contained LED, either within the housing 508 or otherwise within the blade 512, for distributing the emitted light. In addition, a clear, thin plastic sheath (not shown) can be disposed about the assembly prior to examination in order to prevent contamination in the event the portable illumination assembly 504 is intended for reuse.

Figure 36:
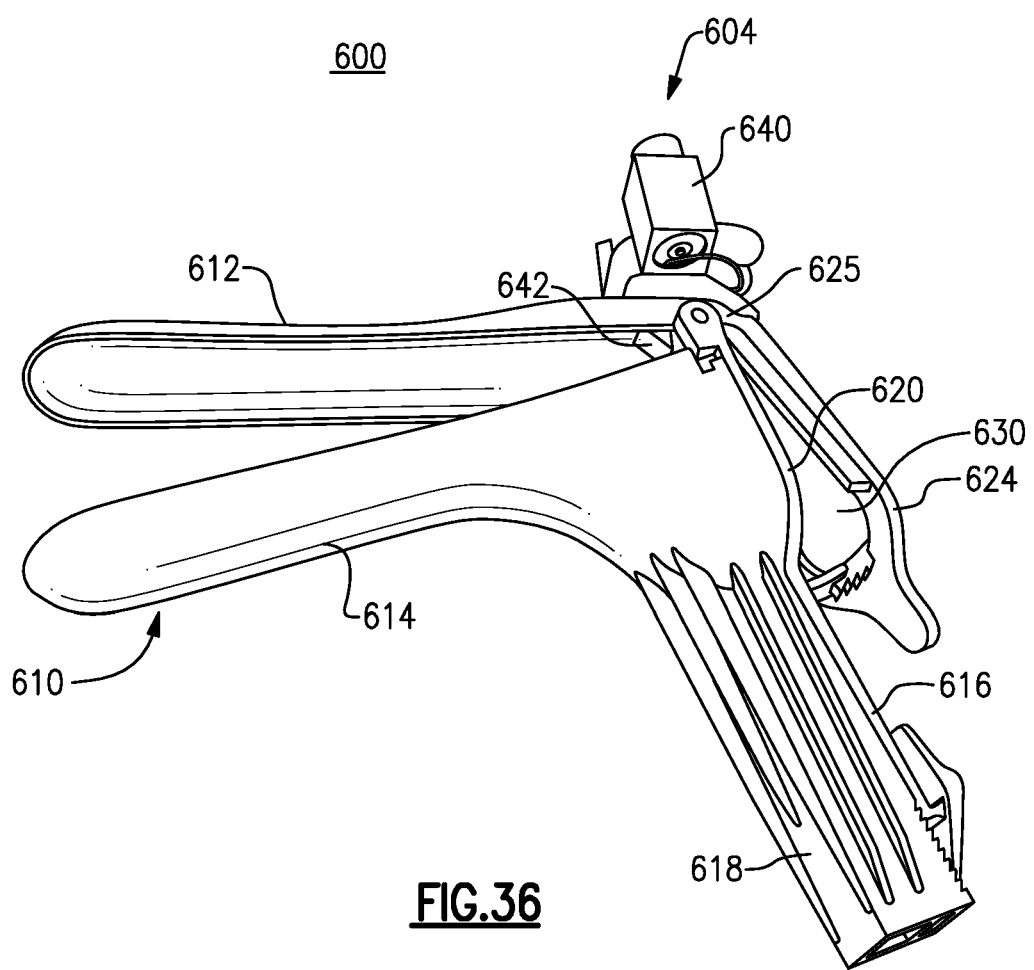
FIG. 36 is a side view representing a vaginal speculum apparatus made in accordance with another exemplary embodiment.
Figure 37:
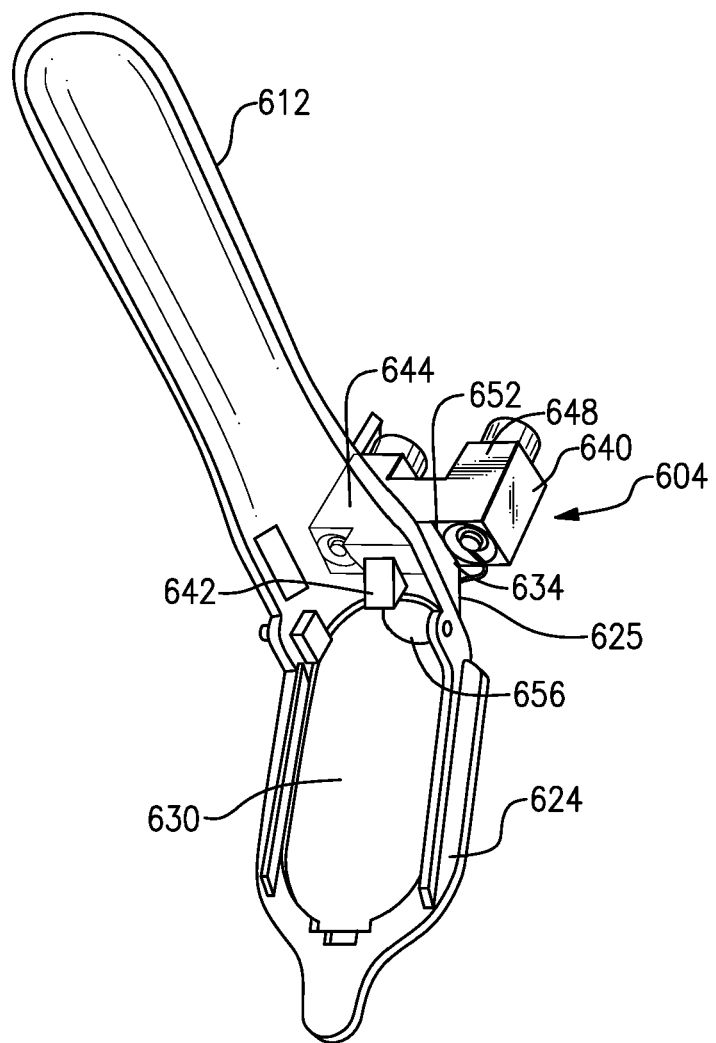
FIG. 37 is a bottom perspective view of a portion of the vaginal speculum apparatus of FIG. 36, in particular representing the top blade of a disposable speculum having an illuminator assembly releasably attached thereto

Referring to FIGS. 36 and 37 and according to another embodiment made in accordance with the present invention, a vaginal speculum apparatus 600 can be provided that includes an illuminator assembly 604 that can be releasably attached to the top blade 612 of a disposable speculum 610. The disposable speculum 610 is similarly designed in accordance to the prior embodiments discussed herein and including the top blade 612, as well as a lower blade 614, a slide member 616 and a hollow handle 618. As described in prior embodiments, the slide member 616 is part of an articulation mechanism including a yoke or upper section 620 that extends upwardly and permits pivotal connection of the top blade 612 by means of a lever portion 624 downwardly extending from a proximal end 625 of the blade. The top and lower blades 612, 614 define a proximal viewing aperture 630 therebetween for the user, as previously discussed.

In this particular embodiment, the portable illumination assembly 604 is attached to a top surface 634 at the proximal (rearward) end of the top blade 612. The assembly 604 is defined by a compact housing 640 sized to retain a miniature light source, such as at least one LED, as well as batteries separately provided in spaced depending leg portions 644, 648 of the housing. It should be readily apparent that the number and orientation of the batteries can be varied, for example, depending on sizing of the batteries themselves and should not be limited by this exemplary configuration. In addition, the batteries can be rechargeable, the housing according to one version including an inductive loop or similar recharging circuit, permitting the housing 640 to be hermetically sealed. Otherwise, the batteries can be releasably attached within the housing. The housing 640 further includes a prismatic member 642, which is optically coupled by means of at least one lens element (not shown in this view) to the contained light source (LED(s)). The housing 640, according to this embodiment, is substantially U-shaped, including the leg portions 644, 648 and a connective base portion 652 but it will be readily apparent that numerous other design configurations are possible. The base portion 652 is secured to the top blade 612 by conventional means, such as by at least one fastener. The base portion 652 further includes a proximal extending section 656 that retains the prismatic member 642, the proximal portion extending downwardly over the rear edge of the blade 612 wherein the prismatic member is aligned with the opening formed in the lever portion 624 such that the light emitting surface of the prismatic member is aligned with the viewing opening 430 between the top and lower blades 612, 614.

The contained LED is electrically connected to the batteries and to the resident circuitry to enable energization of the LED or other contained light source. A switch assembly (not shown) permits selective powering of the contained light source.

Still other alternative embodiments are possible. Referring to FIG. 23, a vaginal speculum apparatus 700 includes a self-contained portable illumination assembly 704 which is releasably attached in conjunction with the lower blade 712 of a disposable speculum 710. As in preceding embodiments, the speculum 710 is defined by a top blade 711 and the lower blade 712, the latter including a hollow handle portion 716. An articulation mechanism 724 includes a lever portion 728 extending downwardly from a proximal end 730 of the top blade 711 that is engageable with teeth provided on a flexible projection 732 extending outwardly from the lower end of a yoke 736 of a slide member 740. A flexible tongue 744 enables movement of the slide member 740 to permit the top and lower blades 711, 712 and enable dilation of a patient.

In this embodiment, the portable illumination assembly 704 comprises a compact housing 750 that retains a miniature light source 754, such as at least one white or other color LED, as previously described, as well as a portable power supply and resident circuitry for powering the contained LED. According to this design, the output of the contained light source 754 is optically and structurally coupled to a light collecting lens 758 formed or connected at a proximal end 760 of a light pipe 764, the latter extending within a trough-shaped portion of the lower blade 712. Because the illumination assembly 704 is cordless, according to this and the prior described embodiments, the apparatus 700 is quite versatile and can be used, for example, with bed-ridden patients. As such, there are no issues such as previously encountered with cabled assemblies. The illumination assembly 704 can be easily reused by removing same from the speculum 710 after examination and discarding the speculum. Alternatively, the speculum 710 and illumination assembly 704 can each be discarded following single or single patient use. In instances in which reusable use is intended, the illumination assembly 704 can be covered prior to use with a disposable sheath 766. An exemplary version of such a sheath is described in U.S. Ser. No. 10/393,848, the entire contents of which are herein incorporated by reference.

Figure 24:
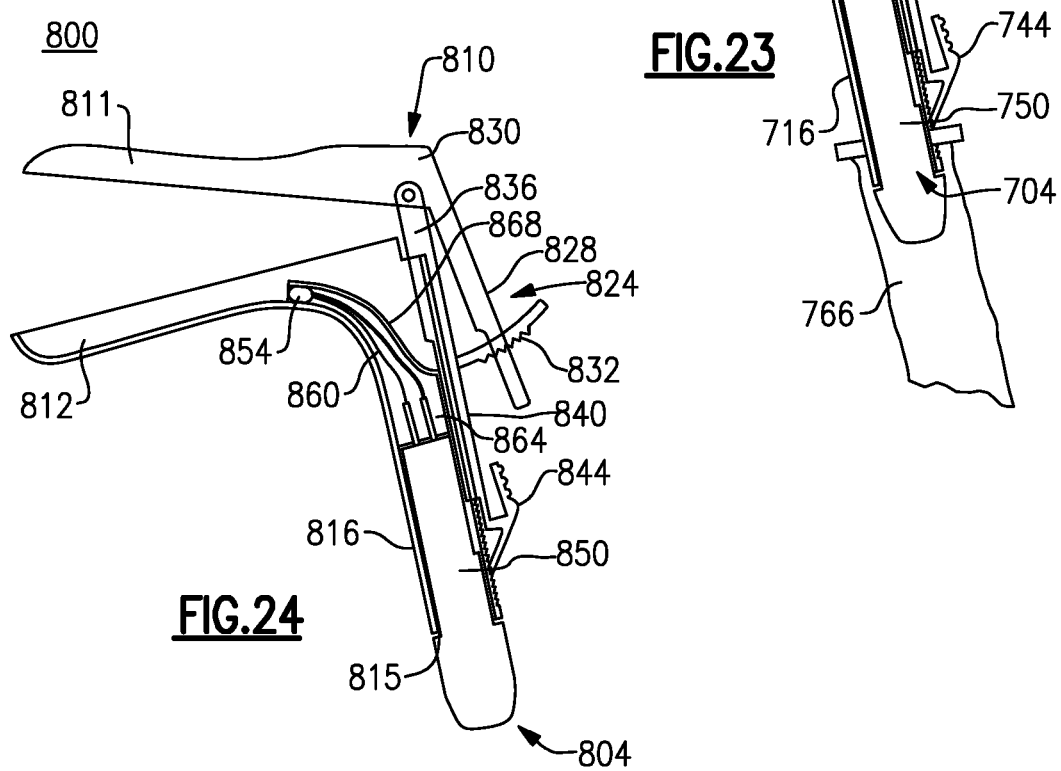
FIG. 24 is a side view of a vaginal speculum apparatus made in accordance with another embodiment.

Yet another embodiment of a vaginal speculum apparatus 800 is shown in FIG. 24. This apparatus 800 includes a portable illumination assembly 804 that is releasably or otherwise engaged with a vaginal speculum 810. As in preceding embodiments, the speculum 810 is defined by a top blade 811 and the lower blade 812, the latter including a downwardly extending and hollow handle portion 816. An articulation mechanism 824 includes a lever portion 828 extending downwardly from a proximal end 830 of the top blade 811 that is engageable with teeth provided on a flexible projection 832 extending outwardly from the lower end of a yoke 836 of a slide member 840. A flexible tongue 844 enables movement of the slide member 840 to permit the top and lower blades 811, 812 to permit patient dilation. The yoke member 836 and the lever portion 828 combine to form a viewing aperture at the rear of the speculum 810.

The illumination assembly 808 is defined by a compact housing 850 that is sized to be fitted into an open slot or cavity 815 of the hollow handle 816 or otherwise attached to the lower blade. The housing 850 retains a portable power supply (not shown), such as at least one battery, and resident circuitry (not shown) for powering a contained light source 854, such as a white LED. According to this embodiment, the light source 854 is disposed above the hollow handle portion 816 and more specifically at the proximal end of the trough-shaped lower blade 812 along a surface thereof, and in the position of the light emitting end of the light pipe of the prior embodiments. The light source 854 is coupled to the remainder of the housing 850 by a set of lead wires and electrical contacts 860, the latter being covered by an assembly enclosure 864 which is fluid-sealed. In one version, the enclosure 864 is formed, by a wall or barrier 868 forming a suitable compartment or can otherwise be alternatively provided as part of the housing itself as previously described in related embodiments.

PARTS LIST FOR FIGS. 1-37

100 vaginal speculum apparatus
102 disposable speculum
102 disposable speculum
104 lower or bottom blade member
108 upper or top blade member
112 slide member
116 trough-shaped distal blade
120 handle portion
123 rear flexible projection
124 forked upper end or yoke
125 ratchet teeth
128 lever portion
129 tongue
130 ratchet tooth
131 teeth
133 receiving cavity
134 slot
135 viewing aperture
136 lateral spring-like protrusions
137 tab
139 interior slot
140 illumination assembly, corded
140A illumination assembly, corded
140B illumination assembly, corded
144 housing, illumination assembly
144A housing, illumination assembly
144B housing, illumination assembly
146 light pipe
147 distal light-emitting end
148 distal portion
148A distal portion
148B distal portion
152 strain relief
156 electrical cable
160 switch assembly
163 depressible button
164 electrical cable
168 pronged plug
172 female plug
174 cable
176 power supply transformer
200 vaginal speculum apparatus
204 disposable speculum
212 upper or top blade member
214 lower or bottom blade member
215 elongate section or blade
216 handle portion
216A handle portion
217 receiving cavity
217A receiving cavity
220 slide member
221 opening
222 external teeth
223 guide slot
224 lever portion
225 flexible projection
226 ratchet teeth
227 bottom tab 228 yoke or upper portion
229 lower tongue
230 illumination assembly
232 LED
235 top surface
236 housing
238 tubular open-ended extending portion
240 circuit board
241 spacer tube
242 battery
243 conductive contacts
244 heat sink
245 upper portion
246 internal centering fingers
247 short circuit/over circuit protection device
248 slider switch
249 guide rails
250 rail like portions
250A rails
251 LED driver
253 projections
254 light pipe
255 proximal end
256 ribs, vertically extending
258 distal end
259 lens
260 base portion
261 pin, detent
262 collecting lens
263 leaf spring
264 pedestal section
265 annular gap
266 sheath member
268 tab
270 frangible tear strip
272 recessed portion
276 inner walled cavity
280 tabs
281 speculum adapter
282 external envelope
283 internal envelope
284 plunger, spring loaded
285 guide rails
286 charging contacts
287 bottom surface
288 power adapter
289 clamping recess
290 conductive strip member
291 plug-in cord
292 lower end
293 cable
294 switch contacts
295 low-power indicator
296 transformer
297 receptacle
298 power adapter
299 pins
300 vaginal speculum apparatus
304 disposable speculum
306 illumination assembly
308 upper or top blade member
312 lower or bottom blade member
316 handle portion
317 receiving cavity
320 slide member
324 lever portion
332 yoke
336 opening
340 tab
344 interior slot
348 curved member
352 ratchet teeth
356 tongue
358 teeth, ratchet
360 illumination source housing
364 battery housing
368 rotatable switch
372 base section
378 apparatus
380 illumination assembly
384 housing
388 lower or proximal end
392 lens
396 heat sink
400 circuitry
404 battery
408 docking station
412 charging sockets
500 vaginal speculum apparatus
504 illumination assembly
508 compact housing
510 speculum
512 top blade, speculum
516 lower blade, speculum
520 handle portion, lower blade
524 articulation mechanism
526 optical element
528 lever portion
530 proximal end, top blade
532 flexible projection
534 yoke or upper section
538 slide member
542 flexible tongue
600 vaginal speculum apparatus
604 illumination assembly
610 disposable speculum
612 top blade, speculum
614 lower blade, speculum
616 slide member
618 hollow handle
620 yoke or upper section
625 proximal portion, blade
630 viewing aperture
634 top surface
640 housing
642 prismatic member
644 leg portion
648 leg portion
652 base portion
656 proximal extending portion
700 vaginal speculum apparatus
704 illumination assembly
710 disposable speculum
711 top blade, speculum
712 lower blade, speculum
716 handle portion
724 articulation mechanism
728 lever portion
730 proximal end, top blade
732 flexible projection
736 yoke
740 slide member
744 flexible tongue
750 housing 754 light source
758 lens
760 proximal end, light pipe
764 light pipe
766 disposable sheath
800 vaginal speculum apparatus
804 illumination assembly
810 vaginal speculum
811 top blade, speculum
812 lower blade, speculum
815 open slot or cavity
816 handle portion
824 articulation mechanism
828 lever portion
830 proximal end, top blade
832 flexible projection
836 yoke
840 slide member
844 flexible tongue
850 housing
854 light source
860 lead wires and electrical contacts
864 enclosure
868 wall or barrier
1200 vaginal speculum apparatus
1204 disposable speculum
1212 upper or top blade member
1214 lower blade member
1216 integral handle portion
1220 slide member
1222 lever portion
1226 yoke or upper portion
1234 receptacle
1238 open end
1242 upper portion
1246 lower portion
1260 illumination assembly
1264 casing or housing, hollow
1268 prismatic member
1269 upper portion
1272 miniature LED
1276 cartridge
1280 battery
1284 electrically conductive strip member
1286 condensing lens
1288 spring
1292 end cap
1304 housing, cartridge
1306 distal end
1310 reflector cap portion
1314 circuit board
1318 circuitry
1322 opening
1326 projecting end
1327 axial groove
1329 electrical contact
1330 heat sink
1331 electrical contact
1333 cartridge collar
1334 strip member
1335 battery contact board
1336 opening
1337 rivet
1338 tapered portion
1339 chamfered hole
1600 vaginal speculum apparatus
1608 illumination assembly
1612 housing
1614 light source
1616 light collecting lens
1620 light pipe
1624 disposable sheath assembly
1628 spool member
1632 sheath
1700 vaginal speculum apparatus
1708 illumination assembly
1712 housing
1716 light source
1720 lead wires
1724 enclosure
1725 barrier/wall It should be readily apparent that other variations and modifications will be possible to those of sufficient skill in the field, these variations and modifications being considered within the inventive ambits described herein. For example, though each of the preceding embodiments depict a specific battery relation, other configurations and orientations capable of electrical interconnection can be used within the intended scope and breadth according to the following claims. In addition and though each of the embodiments related directly to a speculum with an enclosed receiving cavity, it is conceivable that the embodiments described herein can also be used, for example, with speculums having open-walled handle portions. Still further, the illumination assembly discussed with regard to each of the embodiments can be either a disposable version or, as described by a number of embodiments herein, a reusable assembly that can be attached to a disposable speculum.

We claim:

1. A vaginal speculum apparatus comprising:
   a speculum having an upper blade, a lower blade and a handle portion, the handle portion having an enclosed receiving cavity with the exception of an open lower end; and
   an illuminator including an illuminator housing retaining a light source and at least one battery, the illuminator being sized to fit within the receiving cavity through the open lower end, wherein the illuminator includes at least one exterior feature on the illuminator housing that is configured to automatically energize the retained light source when the illuminator is slidingly advanced through the open lower end to a predetermined distance within the enclosed receiving cavity.

2. The vaginal speculum apparatus according to claim 1, wherein the handle portion is further defined by a closed upper end opposite the open lower end, the speculum further comprising a curved light pipe having a proximal end adjacent the closed upper end.

3. The vaginal speculum apparatus according to claim 2, wherein the curved light pipe has a distal end extending along the lower blade.

4. The vaginal speculum apparatus according to claim 3, wherein the distal end of the curved light pipe is angled.

5. The vaginal speculum apparatus according to claim 2, wherein the illuminator housing includes a light emitting end optically coupled to the proximal end of the curved light pipe when the illuminator is positioned the predetermined distance within the receiving cavity.

6. The vaginal speculum apparatus according to claim 1, wherein the at least one exterior feature on the illuminator housing engages an interior feature within the enclosed receiving cavity when the illuminator is slidingly advanced to the predetermined distance to cause automatic energization of the retained light source.

7. The vaginal speculum apparatus according to claim 6, wherein the at least one exterior feature on the illuminator housing comprises a slider switch movable between a first position and a second position when the illuminator engages the interior feature within the enclosed receiving cavity.

8. The vaginal speculum apparatus according to claim 7, further comprising a spring-loaded plunger disposed on the illuminator housing opposite the slider switch to bias the slider switch into one of the first and second positions.

9. The vaginal speculum apparatus according to claim 7, wherein the handle portion includes a slot enabling manual access to the slider switch.

10. The vaginal speculum apparatus according to claim 7, wherein the illuminator is configured to function as an examination light separate from the speculum.

11. The vaginal speculum apparatus according to claim 1, further including an articulation mechanism for moving the upper blade relative to the lower blade.

12. The speculum apparatus according to claim 11, wherein the articulation mechanism includes a yoke provided on the proximal end of the lower blade that engages a lever portion extending from a proximal end of the upper blade.

13. A speculum assembly comprising:
 a vaginal speculum having a lower blade, an upper blade and a handle portion, the handle portion including an enclosed retaining cavity with the exception of an open lower end; and
 an illuminator including a light source, at least one battery for powering the light source, and at least one feature for energizing the light source automatically only when the illuminator is slidingly advanced to a predetermined distance within the enclosed receiving cavity through the open lower end.

14. The speculum assembly according to claim 13, wherein the illuminator further includes an illuminator housing wherein the least one feature is at least one exterior feature on the illuminator housing that engages an interior feature within the enclosed receiving cavity when the illuminator is slidingly advanced to the predetermined distance to cause automatic energization of the retained light source.

15. The speculum assembly according to claim 14, wherein the at least one exterior feature comprises a slider switch which is biasedly movable between a first position and a second position when the illuminator engages the interior feature within the receiving cavity.

16. The speculum assembly according to claim 15, further comprising a spring loaded plunger disposed on the illuminator housing opposite the slider switch for biasing the slider switch in one of the first and second positions.

17. The speculum assembly according to claim 15, wherein the handle portion includes a slot enabling manual access to the slider switch.

18. The speculum assembly according to claim 15, wherein the enclosed receiving cavity includes a set of rails on opposing sides, each set of rails having the at least one internal feature, thereby enabling the illuminator to assume two mounting orientations that permit automatic energization of the retained light source.

19. The speculum assembly according to claim 13, including a curved light pipe having a proximal end that is optically coupled to the light source of the illuminator when the illuminator is positioned at the predetermined distance within the receiving cavity.

20. The speculum assembly according to claim 19, wherein the handle portion is defined by a closed upper end, the proximal end of the light pipe being adjacent the closed upper end.

* * * * *